United States Patent
Emalfarb et al.

(10) Patent No.: US 11,981,889 B2
(45) Date of Patent: May 14, 2024

(54) NICOTINAMIDE RIBOSIDE PRODUCTION IN FILAMENTOUS FUNGI

(71) Applicant: DYADIC INTERNATIONAL (USA), INC., Jupiter, FL (US)

(72) Inventors: Mark Aaron Emalfarb, Jupiter, FL (US); Ronen Tchelet, Budapest (HU); Kari Tapio Koivuranta, Espoo (FI); Marja Hannele Ilmén, Espoo (FI); Sandra Castillo, Espoo (FI); Paula Jouhten, Espoo (FI)

(73) Assignee: Dyadic International (USA), Inc., Jupiter, FL (US)

( * ) Notice: Subject to any disclaimer, the term of this patent is extended or adjusted under 35 U.S.C. 154(b) by 0 days.

(21) Appl. No.: 18/049,495

(22) Filed: Oct. 25, 2022

(65) Prior Publication Data
US 2023/0183638 A1    Jun. 15, 2023

Related U.S. Application Data

(63) Continuation of application No. PCT/IB2021/053565, filed on Apr. 29, 2021.

(60) Provisional application No. 63/017,668, filed on Apr. 30, 2020.

(51) Int. Cl.
C12N 1/14    (2006.01)
C12P 19/38    (2006.01)

(52) U.S. Cl.
CPC ............. C12N 1/145 (2021.05); C12P 19/38 (2013.01)

(58) Field of Classification Search
None
See application file for complete search history.

(56) References Cited

U.S. PATENT DOCUMENTS

| | | |
|---|---|---|
| 8,114,626 B2 | 2/2012 | Brenner |
| 8,268,585 B2 | 9/2012 | Emalfarb |
| 8,871,493 B2 | 10/2014 | Emalfarb |
| 2009/0202680 A1 | 8/2009 | Brenner |
| 2010/0129880 A1* | 5/2010 | Gudynaite-Savitch ...................... C12N 9/2437 435/99 |
| 2012/0164270 A1 | 6/2012 | Brenner |
| 2017/0296564 A1* | 10/2017 | Dellinger ................ A23L 33/40 |
| 2018/0343812 A1 | 12/2018 | Leo |
| 2022/0056458 A1* | 2/2022 | Shoji ......................... C12N 9/92 |

FOREIGN PATENT DOCUMENTS

| | | |
|---|---|---|
| CN | 105463007 B | 7/2018 |
| WO | 2010111111 A1 | 9/2010 |
| WO | 2013085555 A2 | 6/2013 |

(Continued)

OTHER PUBLICATIONS

YeastGenome ("BNA6", Saccharomyces Genome Database, Stanford University, Stanford, Ca, USA, available at https://www.yeastgenome.org/locus/S000001943 accessed on Aug. 16, 2023) (Year: 2023).*

(Continued)

*Primary Examiner* — Robert J Yamasaki
*Assistant Examiner* — Charles Zoltan Constantine
(74) *Attorney, Agent, or Firm* — Rodney J. Fuller; BOOTH UDALL FULLER, PLC

(57) ABSTRACT

The present invention relates to genetically modified ascomycetous filamentous fungi, particularly of the species *Thermothelomyces heterothallica*, capable of producing elevated amounts of nicotinamide riboside.

14 Claims, 19 Drawing Sheets

Specification includes a Sequence Listing.

(56) References Cited

FOREIGN PATENT DOCUMENTS

| WO | 2017144777 A1 | 8/2017 |
|---|---|---|
| WO | 2018211028 A1 | 11/2018 |
| WO | 2018211051 A1 | 11/2018 |
| WO | 2020161682 A1 | 8/2020 |

OTHER PUBLICATIONS

Kegg ("Enzyme: 2.4.2.19", Kegg database, Genome, Japan, available at https://www.genome.jp/entry/2.4.2.19, accessed on Aug. 15, 2023 (Year: 2023).*

NCBI Blast (NCBI Reference Sequence: XP_003659889.1, available at https://www.ncbi.nlm.nih.gov/protein/XP_003659889.1?report=genbank&log$=protalign&blast_rank=1&RID=DRFP8E4D016, most recent update 2019) (Year: 2019).*

Visser ("Development of a mature fungal technology and production platform for industrial enzymes based on a Myceliophthora thermophila isolate, previously known as Chrysosporium lucknowense C1"Industrial Biotechnology, 2011, 214-223). (Year: 2011).*

Altschul et al., (1990) Basic local alignment search tool. J Mol Biol 215(3): 403-410.

Archer (2000) Filamentous fungi as microbial cell factories for food use. Curr Opin Biotechnol 11(5): 478-483.

Boutet et al., (2016) UniProtKB/Swiss-Prot, the Manually Annotated Section of the UniProt KnowledgeBase: How to Use the Entry View. In: Edwards, D. (eds) Plant Bioinformatics. Methods in Molecular Biology, vol. 1374. Humana Press, New York, NY. pp. 23-54.

Castillo et al., (2016) Whole-genome metabolic model of Trichoderma reesei built by comparative reconstruction. Biotechnol Biofuels 9: 252; 20 pages.

Evans et al., (2010) NAD+ metabolite levels as a function of vitamins and calorie restriction: evidence for different mechanisms of longevity. BMC Chem Biol 10: 2; 10 pages.

Heger et al., (2007) The global trace graph, a novel paradigm for searching protein sequence databases. Bioinformatics 23(18): 2361-2367.

Hucka et al., (2003) The systems biology markup language (SBML): a medium for representation and exchange of biochemical network models. Bioinformatics 19(4): 524-531.

Itoh et al., (2003) The yeast ISN1 (YOR155c) gene encodes a new type of IMP-specific 5'-nucleotidase. BMC Biochem 4: 4; 7 pages.

Jones et al., (2014) InterProScan 5: genome-scale protein function classification. Bioinformatics 30(9): 1236-1240.

Magnúsdóttir et al., (2017) Generation of genome-scale metabolic reconstructions for 773 members of the human gut microbiota. Nat Biotechnol 35(1): 81-89.

Marin-Felix et al., (2015) A re-evaluation of the genus Myceliophthora (Sordariales, Ascomycota): its segregation into four genera and description of *Corynascus fumimontanus* sp. nov. Mycologia 107(3): 619-632.

Pitkänen et al., (2014) Comparative genome-scale reconstruction of gapless metabolic networks for present and ancestral species. PLOS Comput Biol 10(2): e1003465; 12 pages.

Van den Brink et al., (2012) Phylogeny of the industrial relevant, thermophilic genera Myceliophthora and Corynascus. Fungal Diversity 52: 197-207.

Van Oorschot (1977) The genus Myceliophthora. Persoonia—Molecular Phylogeny and Evolution of Fungi 9(3): 401-408.

Varma and Palsson (1994) Metabolic Flux Balancing: Basic Concepts, Scientific and Practical Use. Bio/Technology 12: 994-998.

Wilson et al., (2019) Genetic evidence for Magnaporthe oryzae vitamin B3 acquisition from rice cells. Microbiology (Reading) 165(11): 1198-1202.

* cited by examiner

SEQUENCE LISTING

```
Sequence total quantity: 20
SEQ ID NO: 1            moltype = AA   length = 297
FEATURE                 Location/Qualifiers
source                  1..297
                        mol_type = protein
                        organism = Thermothelomyces thermophilus
SEQUENCE: 1
MIEIPLDHGS LEHLLPASWK SQVTAWLAED TPSFDVGGFV VGDHPRTATL WGKSSGILAG   60
VPFFNEVFAQ CGCTVEWHAR EGSHIESHGD KTALATVKGP ARGILEGERV ALNILARCSG  120
IATMSRRLLV NLRSAGWQGT LAGTRKTTPG FRLVEKYGML VGGADTHRMD LSTMTMLKDN  180
HVWSRGSITQ AVKAAKAAGG FSLKVEVEVQ SEEEADEAIA AGADIVMLDN FTGEGVKATS  240
RSLKEKWKGK KQFLLEVSGG LSEDNAELYI CNDVDILSTS SIHQGVRHID FSLKINV     297

SEQ ID NO: 2            moltype = DNA   length = 968
FEATURE                 Location/Qualifiers
source                  1..968
                        mol_type = genomic DNA
                        organism = Thermothelomyces thermophilus
SEQUENCE: 2
atgattgaaa ttcctctgga tcacggctcg ttagagcacc tcctcccagc ctcgtggaag   60
tcccaggtca ccgcctggct cgccgaggac acgccctcct tcgacgtggg gggcttcgtc  120
gttggcgatc acccacgcac ggcgacgctc tggggcaagt catccggcat cctcgccggc  180
gtcccctttt tcaacgaggt gttcgcccaa tgcgggtgca cggtcgaatg gcacgcccgc  240
gagggctcgc acatcgagtc gcacggtgac aagacggcgc tggcgaccgt caagggcccc  300
gcgcgaggca tcctggaggg cgagcgggtg gccctcaaca tcttggcgcg gtgctctggc  360
attgcgacga tgagccgcag gctgctggtc aacctgcgta gcgccggctg gcagggcact  420
ctggcaggca cgcggaagac gacgcccggc ttccggctcg tggagaagta cggcatgctg  480
gtcggcggcg ccgatactca tcggatggat ctgagcacaa tgaccatgct caaagataac  540
cacgtgtgga gccgcgggag catcacccag gcagtcaagg ctgccaaggc cgcgggggga  600
ttcagcttga aggtcgaggt cgaggtacaa agcgaggagg aggctgacga ggccattgcc  660
gccggcgccg atatcgtcat gctcgacaat ttcaccggag aaggcgtcaa ggccacgtcg  720
```

```
cggagcctca aggagaagtg aaggggaaa aagcagttcc tgctcgaggt ctcgggggg    780
ctgagcgagg ataatgctga actctacatc tgcaacggta agctctcgcc accaaccgtt   840
cccgtacgag gggaattttt ggcggcgtgg attggctgac gatgctgcca gatgtcgaca   900
ttctctcgac aagctccatt caccagggtg tacgccacat cgacttctct ctcaagatca   960
atgtgtga                                                              968

SEQ ID NO: 3              moltype = AA   length = 297
FEATURE                   Location/Qualifiers
source                    1..297
                          mol_type = protein
                          organism = Thermothelomyces thermophilus
SEQUENCE: 3
MSTGSSDSGT QTPSATVEQP NLNGAQQSYT FPTEKLKRRQ TQPGKTPLVL VACGSFSPIT   60
FLHLRMFEMA SDFVRFNTDF EVCGGYLSPV SDAYKKVGLA PGVHRVNMCA RAVEQSSWLM  120
VDPYETVNCD EKGEPRYVPT AKVLRHFDYE INEVLGGIEG TDGQRKKARI ALLAGADLVM  180
SMGEPGLWAP KDLDTILGQY GAFIIERSGT DIDEALASLR QYEHNIWVIS QVIQNDISST  240
KVRLFLKKDL SVRYLIPDPV VEYIEEHGLF SEPSANKSRS RTPDVASGPS DNKPTKG     297

SEQ ID NO: 4              moltype = DNA   length = 1194
FEATURE                   Location/Qualifiers
source                    1..1194
                          mol_type = genomic DNA
                          organism = Thermothelomyces thermophilus
SEQUENCE: 4
atgtcgactg gatctagcga ttccggcact caaacgccct cggcgaccgt ggagcaaccg    60
aacctgaatg gcgctcagca gtcctacact tttccaaccg aaaagctgaa gcgccgccaa   120
acacagcctg gaagacacc cctcgtgctg gtggcctgcg gtcgttctc tcgtacgttt    180
ctcagttgct acttgctgtc ccattccac tgctgacgga tactatgcaa gcaataacct   240
tcctccacct ccgcatgttc gagatggcaa gcgactttgt ccggttcaac accgacttcg   300
aagtgtgcgg cggatatctg tcaccggtac gactcggaga acccctccc cagagcaggc   360
gagaagcagg gctgacagag gtatcatcac gtgtgcaggt cagccgacgt tacaagaagg   420
tggggctagc gcccggcgtc caccgggtca atatgtgcgc gagagccgtc gagcagtcgt   480
cctggctcat ggtcgacccg tacgagacgt caattgtgca cgaaaagggg gagccgcgat   540
acgtgccgac gccaaggtc ttgcgccact ttgattacga aatcaatgaa gtgctcggag   600
gtatcgaggg cacagtgggg cagagaaaga aggctcggat tgcgcttctg gctggtgcgt   660
caagcttcgc caacaggccg tcgaaggttt gctgacctca atgttgtttc aggcgccgac   720
ttggtcatgt ctatgggtag gttttgctgtc cagtcatgct cacacgacgc cgactaactt   780
ggtttcttag gtgagcctgg gctttgggca ccaaaggatc tcgatacgat cctcggccag   840
tacggcgctt tcatcatcga gcgctccggg acggatatcg acgaggctct cgcctccctc   900
aggcagtatg agcacaacat ttgggtgatc agccaggtca tccagaacga catcagctct   960
actaaggttc ggctgttctt gaagaaggac cttagtgtca ggtacctgat tccggatccc  1020
gtcgtcgagg tttgttctcg tgccccaaat cttagatcgt cgaacagtac gctcacgacg  1080
ccacagtaca tcgaggaaca cggcctgttt tcggaaccca gcgcgaacaa gtctaggagc  1140
cggacaccgg atgttgcttc tgggccttca gacaacaagc ctaccaaggg ctga        1194

SEQ ID NO: 5              moltype = AA   length = 678
FEATURE                   Location/Qualifiers
source                    1..678
                          mol_type = protein
                          organism = Thermothelomyces thermophilus
SEQUENCE: 5
MGHLVTVATC SLNQWVLDWE GNLARIIESI HQAKAAGARL RVGPELEICG YSSLDHFHEL    60
DVYTHSLEML RQLLLDKSTH GILLDIGMPI LHRNLRYNCR VICLDGKILL IRPKMWLAND   120
GNYREMRHFT PWMRPRETEF FHLPKMLAEL QGETHVLFGD AVISTPETAF GAETCEELFT   180
PKAPHIDMAL DGVEIITNSS GSHFTLRKLD TRLQLITEAT RKSGGVYLYA NQQGCDGERL   240
YFDGCAMIIV NGDVVAQGSQ FSLNDVEVVT ATVDLEEVRS YRAAISRAMQ AAASTAKYQR   300
IQTPFELSSE ADDSDVSKAP TLPIQPRFHS VEEEIALCGG CYLWDYLRRS GAAGYLVPLS   360
GGIDSCATAV VVYSMCRIVM QAVEQGNQQV IDDVKRIARY GGEGVLPKTA QELCNQVFTT   420
IYMGMRKQSS RETRQRAKDL SEAIGSYHVN LDIDDEFGQI LPTARGRPGG GSLLILGSAN   480
VGEVSLRGYL TKYDCSSADI NPIGSIDKAD LKRFIAWAEK SFDLPCLHDF LTAVPTAELE   540
PITQDVQSD EADMGMTYQE LTIFGRLRKL NKLGPFGMFQ RLVHDWSIDR ERKPDDDAPY   600
YTPAQVAEKV KKFFHYYAIN RHKMTTLTPA LHCNDYSPDD NRFDLRPFLY PPFWKSWSFK   660
RIDMELEKIE KKRASKKQ                                                  678

SEQ ID NO: 6              moltype = DNA   length = 3029
FEATURE                   Location/Qualifiers
source                    1..3029
                          mol_type = genomic DNA
                          organism = Thermothelomyces thermophilus
SEQUENCE: 6
atgggtcatc tcgtgacggt tgcgacatgt agcttgaacc aatgggttct cgatgtgagt    60
caccaacggc cgtcgctcgg ttcgctctcg tctgttcgta tctgattaac acctttttgg   120
tttcagtggg aagggaacct tgcccgtatc atcgagagca tccaccaggc aaaggcggcc   180
ggtgcacgac tcctcgtctg gcctgtaggt tcccatgagc tcggtggaca atgcgtccat   240
gaagtgtgta tatgtacacg ctgacgggat caaggaactc gaaatctgcg ggtactcgag   300
cctggatcac tttcacgagc tcgatgttta cacgcacagc ctggagatgc tccgccagct   360
tctgctggac aagagcactc atggcatcct cctcgacatc ggcatgccca tccttcaccg   420
gaacctcagg tacaactgcc gcgtcatctg cctcgacggc aagatcctcc tgatcaggcc   480
caagatgtgg ctcgccaacg acggtaacta ccgcgagatg aggcatttca ccccctggat   540
```

```
gcgcccgcgg gagacggagt tcttccacct gcccaagatg ctggccgagc tgcaggagag    600
gactcacgtc ctctttggcg atgctgtcat ctccaccccc gagaccgcct ttggcgccga    660
gacgtgcgag gagctcttca cgcccaaagc tccacatatc gacatggcgc tagacggtgt    720
tgagatcatc accaactcga gcggcagcca cttcaccctg cggaaactcg acacccgcct    780
gcaattgatc accgaggcta cccgtaagtc tggtggcgtc tacctgtacg cgaaccagca    840
aggctgcgac ggcgagcgcc tgtactttga cggttgtgcc atgatcattg tgaacggcga    900
tgttgtcgcc caggggtctc agttcagcct caatgacgtc gaggtcgtga ccgccacggt    960
cgatctcgag gaagtgcggt cctaccgcgc tgccatctct cgtgccatgc aagcggccgc   1020
gtccacggcc aagtatcaga ggatccagac cccgttcgag ctcagctccg aagccgacga   1080
ctccgatgtc agcaaggcgc caactctgcc catccagcca cggttccact cggttgagga   1140
ggagattgcc ctctgcggcg gctgctatct ttgggatgtg agtagtacca cctaggtagg   1200
cactagaggg atgagctctg accttcctgt tccaactcta cagtacctcc gccggtccgg   1260
cgccgcaggt tatctggtgc ccctgagcgg ggggatcgac tcgtgtgcga ctgcaggtac   1320
gcccaacccc gctcccgccc acgccatgcc atgactggct attcgtgctc accgacctcc   1380
cagtggtcgt ctactccatg tgccgcatcg tgatgcaagc cgtcgagcaa ggaaaccaac   1440
aggtcatcga cgacgtcaag cgcatcgcca gatacgcgg cgagggcgtc ctgcccaaga   1500
cggcccagga actctgcaac caggtcttca ccaccatcta catgggcatg aggaagcaga   1560
gctcgcgcga gacccgccag cgcgccaagg acctctccga ggccatcgcc agctaccacg   1620
tcaacctcga catcgatgac gtctacgagg cccagaagaa gctcgtcgtc agcgccctcg   1680
gcttcgatcc caagttcaag gtcgagggcg gcacggtgca ggagaacctg acgctgcagt   1740
gcctgcaagc tagaatcagg atggtcacgg cctatgtgag ttcggccggc acgcgatcca   1800
gccttgttcg tgtgcgcacg cgctgactgg cggtgcagga gttcggtcag attctgccca   1860
cggcgagggg gaggcccgga ggtggaagtc tgctgattct tggcagtgcg aatgtcggca   1920
aggtgagtac cgttcgcgta gttggtggcg agtccatgaa ctgacaaaaa agagaacaga   1980
gtatgttgct acgtcttcga gagagcaagt ccgtagtgag cgggcaaggc tgatacagtc   2040
tggatctcta ggcctcaggg gctacttgac caagtacgac tgctcggtag gtttcacaat   2100
agctgttgct agcttgatgg atgcggcggg gacagcaaag ctaaccctt tcctagagcg   2160
ctgatatcgt acgtcggctc cgccatgcgg tgtagcggca ggaacaaacg acaggacgga   2220
tactgactct cgccagaacc ccatcggctc tatagacaag gccgatcgta agcgcttcat   2280
cgcatgggcc gagaagagct ttgatctgcc atgcctccat gacttcctga cggctgtgcc   2340
caccgccgag ctcgtatgtc cgccctaact cctcccgccc gtaaggagcg tcgtatgcgt   2400
gaacttacgc ctcttgcagg agccatcac gcaagactac gtgcagagcg acgaagcagg   2460
tacggtacct gcactctgag cagtattgat cgtcgatac tgatccgaga tagacatggg   2520
catgacatac caggaactga ccatctttgg tcgactgcgc aagctcaaca agctcggtcc   2580
ttttggcatg ttccagccgc ttgtgcacga ctgagcatc gaccgcgagc gcaagccgga   2640
cgacgacgca ccgtactata cgccggcaca ggtcgccgag aaggtcaaga agttcttcca   2700
ctattatgcc atcaacagtg cgtatccgac tgacttgtgc taaacccact ttaaaaacca   2760
gaggcagctg ctaacgggtg gactagggca taagatgacc acactgacgc ccgccctgca   2820
ttgcaacgac tactgtgggt gttcttctga gcaaagtcta gcaaagaaacg gaaaaaaaca   2880
agagactgac gatggacaca gcgcccgacg acaaccgctt tgatctgcgc cccttcctgt   2940
atccgccctt ctgaagagc tggagcttca agcggatcga catggagctt gaaaagattg   3000
agaagaagcg ggccagcaag aaacagtga                                    3029

SEQ ID NO: 7          moltype = AA  length = 435
FEATURE               Location/Qualifiers
source                1..435
                      mol_type = protein
                      organism = Thermothelomyces thermophilus
SEQUENCE: 7
MTTRYRVEYA LKTHRRDQFI EWIKGLLAVP FVLYSQPHGA IDRQGTVNLS QTREEAHRRY    60
SEILRDVEGM IDDHIAHQND PENPFPSKLK LLVPSIGPFF TRLPLEAAFK YQDSKRYISS   120
RRFVSPSFND VRLILNSAQM MAVTTYGTLQ LATFDGDVTL YEDGQSLEPT SPIVPRLIDL   180
LRKNVKIGIV TAAGYTTADK YYARLHGLLD ALASTTELNP SQKQSLIVMG GEANYLFEFS   240
PSSPHLLAPV PREKWLTPEM AAWDDRDIAQ VLDVAEAALR DCVRTLNLPA VLMRKDRAVG   300
IVPNPPETRI PRESLEETVL VVQKTLELSA AGRARRVPFC AFNGGRDVFV DIGDKSWGVT   360
VCQRWFGSSS EPSRGQGEGG AIKGQNTLHV GDQFLSAGAN DFRARSVGTT AWIASPAETV   420
DLLDELAELM EKRAS                                                   435

SEQ ID NO: 8          moltype = DNA  length = 1626
FEATURE               Location/Qualifiers
source                1..1626
                      mol_type = genomic DNA
                      organism = Thermothelomyces thermophilus
SEQUENCE: 8
atgaccaccc gttatcgcgt tgaatgtatg tgttataacg cccgacgtac cggatctcga     60
ctgacgggtg gatagatgct ctcaaaactc accgccgtga tcaattcata ggtacgttct    120
cctgtagctc cgccttcatc ctcggtgtgg tcggctctta gtggcagttc ccacgggttc    180
gcagtggtat agtgatgctc gcatcaccat gacgcttccc gccaatgtgg aattccgctg    240
accggaaaaa tcagaatgga tcaaggggct gctggcagtg ccattcgtgc tgtattcgca    300
gcctcacgga gccatcgacc ggcagggcac ggtaaaccta tctcagacac gcgaggaagc    360
acatcggaga tacagcgaaa ttctgcgcga tgtcgagggc atgatcgacg accacagtaa    420
gatctggtct gctgtccatt ctggcttct agcggtgatt cacagtcttc cagttgccca    480
ccagaacgac cccgagaatc cattcccgtc gaaactcaag ctcctggtcc ccagcatcgg    540
gccccttctt actcgactac cctagagggc gccttcaaa tcaggaca gcaagcgtta    600
catctcctcc cgccgcttcg tctcccctc cttcaatgac gtccgcctca tcctcaactc    660
ggcccaaatg atgccgtgaa acacatacgg caccctccag ctagccacct tcgatgtgaa    720
cgtgacccctc tacgaagacg ggcaaagcct cgaaccaacc agcccatcg tcccgcggct    780
gatcggtatg cccctcctcg cctgcaagcg ggacaacttt tcagttactg accggaacct    840
gaacctgcca aagacctcct ccgcaaaaaac gtaaagattg catcgtcac cgcggcaggc    900
```

-continued

```
tacacaaccg ccgacaaata ctacgcccgc ctgcacggac tcctcgacgc gctggccagc    960
acgaccgagc taaaccccte ccaaaagcaa tccctcatcg tcatgggcgg agaagcgaac   1020
tacctcttcg agttctcgcc ttcgtccccg cacctcttgg cccccgtccc gcgcgagaag   1080
tggctgaccc cggaaatggc cgcctgggat gaccgcgaca tcgcccaagt gctcgacgtc   1140
gccgaggcgg ccctgcgcga ctgcgtccgg accctcgaacc gccgcccgt gctgatgcgc   1200
aaggaccgcg ccgtcggcat cgtcccgaac ccgcccgaga cgcgcatccc gcgcgagtcg   1260
ctcgaggaga cggtcctggt ggtgcagaag acgccggagc tcagcgcgg agggcgggcc   1320
cgccgcgtgc ccttctgcgc cttcaacggg gggcgcgacg tctttgtcga tatcggcgac   1380
aagagctggg gcgtgacggt gtgccagcgc tggttcggat cttcgtccga gccgagcaga   1440
ggccaaggcg aaggcggcgc aatcaagggg cagaacacgc tgcacgtagg cgaccagttc   1500
ctgagcgcag gggcgaatga tttccggggc aggagcgtcg gcacgacggc gtggatcgcg   1560
agcccggcag agacggtcga cctgctcgac gagttggccg agttgatgga gaagagggcg   1620
tcttag                                                              1626

SEQ ID NO: 9         moltype = AA   length = 238
FEATURE              Location/Qualifiers
source               1..238
                     mol_type = protein
                     organism = Thermothelomyces thermophilus
SEQUENCE: 9
MGCATNGVSP RKVFFFDIDN CLYPRSTKVH DLMADLIDKY FATHLSLPWE DAVRLHKEYY    60
QNYGLAIEGL VRHHQIDPLD YNAKVDDALP LDDVIKPRPE LKKLLGDIDQ SKVKLWLFTN   120
AYINHAKRVV RLLEVEEFFE GVTYCDYSSV PFTCKPQPAM YQKAMREAGV ERYEDCFFVD   180
DSYQNCKKAQ ELGWTVAHLV EDGVKPPKTP ACKFQIRHLD DLRTVFPQCF KGSASEGS    238

SEQ ID NO: 10        moltype = DNA   length = 1137
FEATURE              Location/Qualifiers
source               1..1137
                     mol_type = genomic DNA
                     organism = Thermothelomyces thermophilus
SEQUENCE: 10
atgaagttgc tgtgccgcct acgccttcag acacctctgt ttcagacacg catcacgaca    60
acacagaacc tccatggact aagcgtctgg tcccagttgg cgcagtcgaa gagtcagtca   120
ctttatctta gcaagcggga gatatcgggt cgaaatcaag gagtcgcttc ttgcatgccg   180
agccttagac acgccattgt tgggaatatg ggttgcgcta ccaacggggt ttcccccgc   240
aaagtcttct ttttgtgagt gtgagaaagg acgaggaaca gtcgaccggg ggaggggggg   300
gaagattcta acatgaagca gcgacattga caattgtctc tatccgagga gtgagttacc   360
acgatattca tgggacagtg ccaacactgg atccgggaat agcatgctga tataggaccag  420
gcaccaaggt acacgaccta atggccgatc tcatcgacaa atactttgcc acgcaccctct   480
cactgccctg ggaggatgca gtgcggttac acaaggaata ctaccagaac tacggtctcg   540
ccattgaggg cctggtacgg caccatcaga tcgaccccct agactacaac gccaaggtcg   600
acgacgccct cccgctggac gacgtcatca aaccccggcc agagctcaag aagctgcttg   660
gcgacattga ccagagcaag gtcaagctgt ggctcttcac caatgcctac atcaaccacg   720
ccaagcgagt tgttcgctta ctcgaagtcg aggagttctt cgagggggtc acatactgcg   780
actacagctc cgtgcccttc acctgcaagc cccagcccgc catgtaccag aaggcgatgc   840
gtgaggccgg ggtggagaga tatgaagact gcttcttgt cggtaagtag ccccggttcc   900
tgaggactga gcaaatctat cgtagatccc gatcgttgac agccaaacaa aaaaacagat   960
gattcgtacc aaaattgcaa aaaggcgcag gaactcgggt ggaccgtcgc ccacctcgtc  1020
gaggacggtg tcaaaccacc aaagactcca gcctgcaaat tccagatcag gcatctggac  1080
gacctacgca cagtcttccc gcagtgtttc aagggaagcg cctcggaagg tagctga     1137

SEQ ID NO: 11        moltype = DNA   length = 3353
FEATURE              Location/Qualifiers
source               1..3353
                     mol_type = genomic DNA
                     organism = Thermothelomyces thermophilus
SEQUENCE: 11
agcagcactc cgcggtattt cccttgtatc aatacagctc tgagacggcc gacaacaact    60
tggcaacaaa gatcgacaac actgtgtaaa aagcgaagat gccccgaggc tacttctccc   120
cgtacgcacc gcgcagacgc cgttcgccca ggctcgtctt gatctgggtc tccatcttcc   180
tcttccttct ctggattacc tggtacatta caacccgcca aaggaggag gcagcaccct   240
acgtcgagga gttcattcac ccgggaagga tgccgaggag ggcaaggag gctgccggca   300
acgcagaatg agcttggtgt gagaggaagg gtggcgccaa catgacctgc atggccgcat   360
ctttttgtg ctcgacgac atcgtttcgg actttgttg teccctcgcat                420
tccaacttcc tggtgaacac ggtggccgag gaccccgcca agaactgcga tgtgaaacgc   480
gtcaaggcga agcagcaggc aatcccgatt tggacggatg gcgttggaag aaaaggaggg   540
aaaggaaaac atacaatggg cagggagctc tcatttggat aaacagtaat aaatgtaaca   600
tcactcgcgt ttgattgttg cttttgtggt ttgaggtgac caagcaaagt ccctctgttt   660
ctcttcgtat ctcacactct tatccgtac atgcttcgga cgcactcgga caattgtggat   720
gagcgcgagg aactctaacg gtgcaaaatc ttgattaggc atactgtaca ggctaaaaac   780
acgcccttagc ccacagcgct gcacactgta tggtttccag accatctcac ccacccccct  840
cacttcgctc ttccttcctt cctcaacctc aacaaacgac cccgaggcat cgatagggc    900
aaaaattcct tctgcgatgg atccatgacc taagtcact tacctaggta tcttcggtcc    960
agatatctgc gccctgatga actcttcaat acaaaaactg tagtgttcct ttcagacatg  1020
gacccccgc gcaccatcac tatcggcatc agcggctgct cctcgtctgg gaaaaccacc  1080
ctcgcgaggc tgctgcgtga tatgtttccc gagactttta tccttcacga ggacgacttt  1140
tacaaagccg agtctgagta ggttccgcgc gtcttggccc gtcgccgcc tcgcatcagg   1200
cacattcatg ctgactcgcc caacaaagac ttccgataaa ggacgggttc gccgactggg  1260
actgtcccga atccatatcc attcccgact tggaagccgc tcttgcccac gtccgcgcaa  1320
```

```
cgggcacgtt cccagtcagt agcaatctgc ccactaactc ccctcaccac ctccccccgcc   1380
gcagcagtca cggctgtacc attgcccat  cccttcccc  tgccactgcc actgccactg   1440
ccactgcccc tgcatcaccg cccgtcaatc cctcgtcccc ctcatcatca tctcccgcaa   1500
cgacaagtcc agctcggctc accagacccg ccaaccctca tcgaccacag cccaacgtca   1560
actccctgga ggatctcaac accgtcggcc cctgcccggc gaccccggac cagatcgccg   1620
cctgcgccgc caaggtccgc gcctggctct cccccaaccg cccgggcgcc ctcatctttc   1680
ccccccaagcc gccgtcgtcg tcatcatccc caccaccacc accatcatca tcatcatcac   1740
tactaccatc atcatcttca tcatcggatg ctaccaggcc gcccaagaca cgcgtctgca   1800
tcctcgacgg cttcctcctc tactcccccgc caccgtccac cccacgcgcc acatccacgt   1860
cgaccgccgc cgccgccgcc gccgccgccg gtagcccgct ccgcggggtc atggcccagc   1920
tggacgtcaa gctcttcctg aaggcgagca aggccaaggc gctggagcgg cgcggggcgc   1980
gcgacgggta cgtgcacgtg gatggcttct ggaaggaccc gccggggtac gtggagcgag   2040
tcgtgtggcc caactacgtc gaggcgcacc ggtggctgtt tgagcgcggc gacgtcgagg   2100
gcggccggct ggaccgcgcc gtcctcgaga gggagggcat cttgaccccg gggctcgacc   2160
ccgaccccga cggcggggag gcaggggtg  agagtggagg tggaggagga gaagaaggag   2220
gagtcggggt cggggtcggg gggaaccagg atattgagtt tggtaagatt ctggagtggg   2280
cggttgaagt cgtcatgagg gagttggaga ggctttgcct gggggagaaa gacggcgtgg   2340
ggaaggagta gaggggggcgc agaagaagga gctaactaga ataaaggagg tgggggaaag   2400
gggggggcaag agatagagtg aagaaaggaa ggaatggggg tttatacgga tccgtattag   2460
aactgagggg tttacttggt atcagagaca aatagagatc aatctatcgt cacgcggcga   2520
agctgagctt ctgagtagat atctacacaa cgacagcctc gagtctttgc gaatgccctt   2580
ttattctggg ctaatcaatg catctaaaaa acataattat cgacaggaaa aagaaaatga   2640
agcgctcaag tttcgacact ccgatgacaa aattactaac aaataaactg catcggcctg   2700
ccttttttt  tctttttttt cccaaacgct catgatcatc ctattacctc ccctcttttc   2760
cacccccccc cccaccaag  agccaccgaa ggctccgaat gaggcttttg ctccagtact   2820
cccatatcta ccgccaggtc gcctctgatgg tctgccaggc acagccgctg gccgtggagg   2880
aagagctgac cgtgaactgg cggttcgggt ccgactccca ctggatcgac ccgtcccccgt   2940
tgaccttgac gaacttgtac tgcaccgact ggccggcctt catgggcacc gtgatggccc   3000
agagcgggtc cgacgccgtg taggccgacg cggacaggcg cggggccttg gagacgtccc   3060
agttgccgag ctcggacgag ctgccgacga ccttgaccga ccgccccac tgggtggtca   3120
cctcggcgcg gaaggtgacg aagacctggg tggagtcggc gcaggccgtg gggaacgggg   3180
ccggggtgtc gctggtcggg ttgggcgtct ggccggggcgg gaaggaggtg gcggtggcct   3240
gggtgtaggt gccggcgacc tggacggccg agcacgagcc gggcagcgtc ttgccgtgct   3300
cggcggacca gccggccggg acgatgcccg cgcggcggtc ggcggccgag agg          3353

SEQ ID NO: 12            moltype = DNA   length = 3722
FEATURE                  Location/Qualifiers
source                   1..3722
                         mol_type = genomic DNA
                         organism = Thermothelomyces thermophilus
SEQUENCE: 12
caaggatcaa tcggaggcca agacggcagc agagatgccc ccgccgccca agcctgaggc     60
tcccgcggcg agaaactact tcaaggactc caagacggca ctcacgtcgg agaaaaaata    120
taaggccccg tcgctcgacg acccggcctt cttggcggcc ctcaagaagg ccaaggcggc    180
tagtgccatg gaaaaatcag aagaggagag aaaggcagcg gagcgagaag agcggctcaa    240
gaagaagctc gaagaattgc accgcgacga cgaagatatg gacatgggct ttggctccag    300
ccggggtggaa gacgaaggcg gatctggacga aaccaaggtc aaattgtcgg cctgggatga    360
tgatgacgac gatggcagag ctggcggcgg aggcggcgga ggaggaggaa agtcgcagcg    420
gaagcggggg aagaagaaga aaagggggga caagaatagc tttgcggatg tcatgaaggt    480
gattcagaga cagaagggag gtggcgggta gggccaatgc tttgggagtg cacggcagca    540
attaattact tgttgggca  ctgtactagt gtgccggcct caaactacgg attacaagcg    600
tcaactgagg acacggcaaa cattgccgga aaactgtgaa gctaaaaaag aacgggaaag    660
aacccgcgac gactcttttg ttggggggggg ggggggggttg tgctgactga cccaacttcc    720
tgattaggca actgcgccag cttctgttac tcatgagatc aggcccagtg gatccagaac    780
ggaaacccac ggtctcccgc tccagcgcat cccaagaaga catcctggct tttggcctct    840
taagttcagg ggcaggttcc tgttcacccg cgtctcgtaa aagctttctt gaatcaatcg    900
tcatcaccgg cctcaacgga tagaactcaa tttaacctac ttgatcatcc tcggtaattt    960
ttttctgctt atcaattgtt cctgatccgt acccatattg tcgagctcct cgacatggag   1020
gacacacgaa tcccggtctg gctgactgt  gacccgggtc acgacgtaag tagttttagt   1080
cctggtcgaa gctgatttgt cctccgattg cagcgactct gtttacttcc gggacccggg   1140
cccgtgatca agcgaggcac gacccaggga gcccgatggg atgcggaaac ggaggagggg   1200
gagggggcaaa cagttagctg ggggtggagg gaggttccgt acaccaggtc gctaggcatc   1260
ccatcacaac cacctttcaa tatacacacc cctcctacct cacctcaact tcttggacac   1320
tcacactctc tctcacgtac acgatcacac acttgctcac actctcgtca ggacacttct   1380
gccatcctcc tggccgccta ccacccggca atccgcgtcc tcggcgtctc aaccgtcttc   1440
ggcaatgctt cactcgagta agatctcctt cttttccctc tcgttgacgc ccctagctcc   1500
ctacctgtcc cctgcatttt ttccacttt  tcaacccttt tttctacccc atttaaacgt   1560
gtcaatacta attaatacat gccctcgcca gaaaaacaaac gcgcaatgcc acctccatcc   1620
tcactgccat aggcaaggca tccagcatcc ctgtctacgt cggcgcctcg cacgcgctgt   1680
atcgcccgcc gatgcacgcg cccaccgaca tccacggcga gtcggggtta gacgggaccg   1740
atttgcttcc gccgcagcc  gtggaggcgc gcaccaaccc gccggccatc gatgccgcct   1800
atgccgccct gaaggccacg ccgccgccgca ccgcctgggt cgtcgccacg ggcgccttca   1860
ccaacgctgc cgccctcttc ctcaagtacc cggacctggt cggccacatc cgtgggctct   1920
cgctcatggg ccggcgcctc ggcggcgggct tcaccctgtc gctcctcggc gaggtcgcag   1980
gcgtgccccg cgtcggcaac tggaccagcc tcgccgagtt caacgtcctc gccgaccgag   2040
aggccgcagc cgccatcttt gccaacgcg  agctcgcccg taagaccacc ctgatccctc   2100
tcgacgtgac ccacctggtc ctgaccacgg agagcgtgcg cgacctgctg ctctacggcc   2160
gcgaggaggt ggagaggggc acagacggag aggctcggag gaacggcaag ccaggaaaga   2220
cgaagcttag ggtttatgctg gtggagctgc tgatgttcct tgcaaagacc tacaagtaag   2280
```

```
tttcgttctt ttggggagag tgcgtgagca caacgacggc tgacatgcga gggatagaga  2340
cgtcttcggt atcaccgagg gcccgccgct gcacgacccg ctcgctgtgg ccgcggtcct  2400
gacgggcgtc ggggaccagc acgagatccc cttcgctgac tgtgatcctg cgggggagcc  2460
gggactggcg cagcgggagc gttacgaggt gtcggttgtg accgagggca cctacgaaga  2520
cgcccgcgcc ggagccaagga cgggccagat cacggccaag ctgctccccc cgggcgaaga  2580
gggcgtcagg ataccgcgca gcctggatat cccgctattt tggaaggtcc tggaagagtg  2640
cgtccagagg gcagacgatg ccattgccgc tgccgaggcc gctgctgccg gacagcgtc   2700
aaattgatgc tcttttctcc cccgggagac gaatcatatt ttcggcatgt ggcaaccggg  2760
ggtattcgga agccttttag atctgatacc tcttaaacta gaccggggtc tcttgctgtt  2820
tggatagaag acatgaaacc attcatcgcg ccgcgtggtg gagttagaag tacacccttg  2880
gaaacgcgtt ccctgtgcga tttcacgggg ttcagacgag taccgagatg cttgcccact  2940
atctctcgag actggagaaa gttgatctat tcgtctcaga tggcgtagac aagtaacatg  3000
caagtccgtc accgcgccga gtaggacgac cttactcacg caatcatcag aagaagacat  3060
cgtgatacgg gatgaagctt gttttggcca tcccaactcc aaccgagttg gcacccaacg  3120
ccgaaccaga tgaaccccta atgaaacct  acacaagcgc cacacatacc acctagacac  3180
aaccgaaacac acatccacac acccacacga cagatagaca gagccacaca cacacagaga  3240
gagagaaaga gagatagcaa aagaatcctt tggcctcaag ttgagtcgtc ctcgggcaac  3300
tcctccacca cccgctccac catctcaatc aactcgtcaa tatccggcct ctcgctcggc  3360
tccaccttca gacacctccg gacaacctcg cggatgggct cgctggtggg cgtgtcgttc  3420
cccccggacg tccgttggaa aggcccggcg gccgtgcctt tgcccttgcc cttgcccttc  3480
cctccgggtc cctcatcggg aaaccgccag tctcccgaga aacgcagat gctcagcgac   3540
ccgcccgtct cgtcgctgcg catctcaaaa ggcgacttgc ccaccaggca ggcgtacagg  3600
gtacagccga gcgaccagat gtcgactttc gtgtcaatga cggagccgt cttgacgtcg   3660
aacagctcgg gcgcgcggta cggcatggtg ctgtgctcgg cggccgtgtc ctgggtagcg  3720
at                                                                3722

SEQ ID NO: 13          moltype = DNA   length = 3153
FEATURE                Location/Qualifiers
source                 1..3153
                       mol_type = genomic DNA
                       organism = Thermothelomyces thermophilus
SEQUENCE: 13
tttgagccac ccttcaaagc agctcatggc agacgtgaaa catagctcct cgatggtcaa   60
aggacgccca gtctccttca ctcctgaggc agccatttcg gccggcaatg ctgaagatgc  120
catcgcgcga gctttctcgg accaaccact ccactttcgc cgccgaagcc gaagacttct  180
tctctccgcc cgaccacaaa cttcttatta cactcccctc cctggcgttg atgcaatgaa  240
gcacagagtg gcagtaatat gtgtaaagcg ttatttggcg gctccagaac cgaccgagaa  300
gagctactgg attggattgt ggtctcttgg gtcgggttcg attttgaaag aacagcggtg  360
gttgatccta gggttctctc gttttagaaa attttagacc tacttgtcg ttccttccgc   420
ttgtgagaaa gaggcagtta ataaaactgt taaccctatg cgaagtaaat agtctgaacg  480
tgcggtcttg ccggatcggg ggggttgggg aacgggttc tcgaaagttt acaaatgggt   540
ttgtatgtac ggagtagtat tcagtattcg gactccgtgt aacccgtaat tatccttatca 600
actttgtaga ggcagctctg cacaaacccc gaggtctacg ctaaccactt ccagcactag  660
cgttctcaac agccctgccg acaggggtaa gccctcctg tatcaccgac gtcctcgcaa   720
cggcggggta gagggcgac ccctccgtaa gaccctccaa aaattgcgcc agcggaacag    780
gcaagtaccc aactttatca accgcgtata ttacacacca ggcaacaagg gaggccaata  840
atcagggcgg gtgcagata aaaaaaaaca aaaaaaaaa aaaaaaccaa caccactcgc    900
actccctccg tccgaactct tcctcattcg taacgtcgca agaagctcag tagccccct   960
tcccatctct ctcttccact ctcttccgac cgcgcgccgc gccagaatg actgtcgacg  1020
tccaatccct ccccaccgtc ttcgaccgta agttcgcccc ttcctacccg tttctttccg  1080
tctgggtctt cctcccctgc ctaaagcgac cgaccctcct gtgttgagcg gcggaatgga  1140
aaactaacag agcaattcac tcactcactc tttctctctc tcactctctc tcactctctc  1200
tcgtgcgcag ggccggtcca cattgccgtg atcggcggca ccggtctgtc ctcgctcccg  1260
ggctaccacg ccgtcgcggc cctctcgccg agcacgccgt ggggcaaccc gtcgtcgccg  1320
atcctgatcc tcgagcacgc gggcgtgccg gtggccttcc tggcccgcca cggcctgcac  1380
caccagctcg cgccgcacga ggtgccctcg cgcgccaaca tcgcggcgct ccgctccatc  1440
ggcgtgcgca ccgtcatcgc cttcctccgcc gtcggctcgc tgcaggagca catcaagccc  1500
atggacttg tcgtcccgga ccagatcatc gaccgcacca agggcgtccg ccccttcacc  1560
ttcttcgagg gccgcgttggt cggccacgtc ggcttcgccg accccttcga cgcccgctg   1620
gccgccgtcg tgcggcgctg cgccgccagc atgcgcgaggcg acggcgtcgt cctgcacagc  1680
ggcggcaccg tcgtctgcat ggagggggccc cagttcagca cgcgcgccga gagccacatg  1740
taccgcgcct ggggcggctc cgtcatcaac atgagcgccc tgcccgaggc gaagctggcc  1800
cgcgaggccg agctggcgta ccagatgatc tgcatggcca ccgactacga ctgctggcac  1860
tcgaccgagg acgtcgacgt cgccatggtg atgaaataca cggccgccaa cagcgagaac  1920
gccaagcacc tggtcgggcgc cgtgctggac gagttatgca agcaggagaa cagcgatctg  1980
gtgctcgcca agcactggga aggcagcgct caggggcgg tcaagttcat gaccaagccc   2040
gccggacggg accccgaggc gatgaagagg gtcgagtttc tgtttcctgg attctggaat  2100
gaataaaaaa cggcgcggtc ggcttcttt ggggacgagt tctccggttg ggcgtcttgg   2160
gaagggtggc agcacggatt gattgataga ccaagtccga gagatagatt ttgtcgctag   2220
gaacatagat atatatctat agaccagttg cctgacaggc catggtacga cgcgaggcgg  2280
taacttctcc ggccagcgct gtccgagaca tgcattccca agtatgttaa tgtgtatttg  2340
tataggaaat cttctccggg tatcccaatt gcatccgcac catccatcct ccagccatca  2400
tcacacaaac acgcaccaaa caaacaaac aaaatttaac acgccccgac aacaccaaga   2460
agagcgcgt gtgcaaaaca atcacaaaca aaataaaaaa aaaggaaccg                2520
tacaccacac ttctcctccc cgtctttcca cagtccatca catcaataga tacaacgccc  2580
ttacagcctt ctccacaaca gccacatgcc agggcctcac atctacatcg cgctccgtca  2640
cgcccctcgc ccgagccaac gtgcctaggc ccctgaaata cgtcaacatc tcccttagca  2700
agacatcata catggccctc gcgttgtcgc tgtagaccac gttcacctcc atcgcaaccg  2760
gagcatcgtc ctgtctcggg ccggaccgct tcaccaggta cccgctcgcg agggccgggt  2820
```

```
tgaggtccgt gagggacgcc gagttgttga gtctgtgcga gacaaccacg ccccaggtgg   2880
tctccgtcac gtcgacgagc gtggtgtcgc cgtccgcatc ggactggctt gtctgggatg   2940
ccggttgttg ctgttgttgt tgttgttgct gggaggagtc gccgccgggg gtcgtggcac   3000
cggctggggt gcctgtgttg ccaactggcg tggacgggtt tccggattgg tccggggaga   3060
ggacggatgg tggctgcggg gtggagactg gcgtcgtgta aagacgagg ggagcggata   3120
gtggaatcgt agcggcggga gggataagtt gga                                3153
```

SEQ ID NO: 14        moltype = DNA  length = 4153
FEATURE              Location/Qualifiers
source               1..4153
                      mol_type = genomic DNA
                      organism = Thermothelomyces thermophilus
SEQUENCE: 14

```
ccactgcccg tcttggcagc accaagaatg tcgttgccct tgagggcgag ggggatggcg     60
gctcgttgga tgtcggtcag gacctcgaag tgggaggcgc gcaggccggt cgcggtagct    120
tcgcagaggg ggaggtcggt gaagttgttg aggtcggctg atttgggtc ctgcggtcga    180
atgctttggt tagataactg aaagtcgaca gcgacaaaaa aagaagaaa aagacaaaaa    240
gaaaaaggag cagcaatggg cattattagc tcgaagggtg cgttgtactg accaactgct    300
caatcgccgc tttcagctta ttcaggtcct cctctcctcg cttcctcttg agtgacttca    360
cttctttctt aagaatcggc ttttttgcgat gtgggagacc gtcttttgtg ctaccggccg    420
ccatcttgtt gtccgggctg aaattggcag aatggtgcta actccaggcg tcagttcccc    480
gttccaaagc ctatcgagaa gcaccttcac ggggaaattt ttggcggaga ggaattctgc    540
cgcctgcccc accactgcag attcgctcca ctccgaccct actatgtagc aattaaaagc    600
acccagtaca tacataacta gctggataaa cagtgcagta cagatcacat gcagtagcgt    660
acccagccgg ttgaaaatcg ccctgtcgcc ggacgaaagg gcatgaacga caggactacg    720
gagtactttg gacagttacc gaattgcagc cgggtttttg aggattttgg cgtgaattgt    780
gttcacaacg ttgtcgtgag agagaggggg gaaatacgca gcgacatggg cgatgtcgta    840
ttcatgtgcc catacatcat catcatcata catagagaga gagcacacag tcccaggtat    900
tccaaccgat ggcctgtcta tagaacacgg cggaaaataa taaaacggga aaaaaatatc    960
gataaaacca aaaaaaaaac actcggataa acaagaacaa tgtcatcgtc ctctataccg   1020
ccttccccgc gtccttggcc gcgctcccgc tctccacttc ctcctcctcg accccgacca   1080
ggctgctgct cctccgatcg tggtaggcga cgcgcaggtc gccgatctcg tcgccgacct   1140
ccatccagcg gtcgctggtg gcggggacgg gccagatgcg gcagagcagc cagtagacgg   1200
cggcggagac gccgaagccg cagaagaagt tgaggttgta caggtatgtg gcaccgatgg   1260
ggacggggt gccgacggcg ccggcgaagc cgacgacgtt gatgaggatg ccggcgatgt   1320
aggcggcgta ggcgcgccag tggatgccgg ccgtgtagaa gtaggccccc gtccggcggg   1380
cgtcgtacag ctccttgacc tcgaggaagc cgcggcggac gaggtagtag tcggcgatca   1440
tgacgccggc gatggaggac aggaagacgc tgtaggcgga caggtaggtg gtgaacatgt   1500
tgcttgaggt cagcaggttg taggggcaca tggcgaggcc caggatgtagc   1560
cgccgcggcg gatgttgatg tagcgcggca gcagggccgt catgtcggtg ccggccgaga   1620
ccgagttggc ggcgatgttg gtgccgagct gggcgagggc gaaggcggcg gcgatgacga   1680
agacaccgaa gcgctgggcc gagccgccgt cgtcgaggaa gtgctcgagc aggtcgagcg   1740
ggtcccagat gggcttgccg ccgtagatga cggctgacga cggcgagacg atgatgccga   1800
tgaaggaggt gagggcgaag ccgatgggga tggtgaagag ctgcgaccac agcgcgtcgc   1860
gcggcttgcc cgcgaaacgc gagaagtcgg gcgagttgac aatgagggtc gcaaagttgg   1920
cgatggagct catgacgccc ttgatgaact cccaggccag ctcgccgccc tcttggtgcg   1980
ccggctgccg gacgatgggg ccgacgccgc cggcgcggac gacggaccag atgagaaagg   2040
caatgcccgc gcagggaaca acatagggcct tgacgtgaa gaggtgccgg atcttgtgga   2100
ccgggaacca gatggccgga agcgagcaga accagaagag gaagaaggag acgtaatcgg   2160
ccgtcgaggt gcccgagtcc tgggagaacg tgttgggat ggtttcgcgg tcctatagga   2220
aagagttaat taggacactc tctagacgac aggagagat atgaaaggag tgtgggctt   2280
gatagggtcc tcttcttttt ggcacgaagt catgcagaca acaagggtgt gcgtttctta   2340
cccagctctt ccagatagac cgtatcatta gatacacgca gtgtcctcca atgtacgact   2400
gcacgccata ccagatacac gctgctcatc cgttagtccg cacagccgac gaatccgtgg   2460
gggaattgtt tgtgggtttg ggggagaga cacgcaccca tggccgctcg gttgaagacg   2520
ggccacagac taccccagat gccaaacgac gaacggctcg cgacgggaa gccgatgtgg   2580
taggtggcgc cgatccgggc ggtcatgcag atgaaggagc ccgagatgga atagccgatc   2640
cagacgcaga gccacgactg ccaccacgac aggccgccca caatcatgga cgacgagatc   2700
atccaggtgt tgatgttgaa cgagtcggca acccagaagc cgacaaagtt ccagggtccc   2760
cattggcggc gttccggctc gacggcttg aggtcatggt ttgtcaactg ggcagagggg   2820
ggtttgcagg tcagcgggcg gccatgcaaa attatgaaaa aagagatcga ggtgcacttg   2880
aacacggaca gcaaggggag gggaaggcg aagagggaag agaacaggag agagaggggg   2940
gggatcagtc agacaaaatt tgattttatc cctttcccct ctctctccct ctttcccttt   3000
ctaccctctc ttccgtcccc tccgtccgcg caggtgtctg ttcaggtggg cttccgcacc   3060
atcatctggg cgctggtgag gcccggttcg gagtcgacgg ccaccttgtt ggccaagcgc   3120
cgtaagacgc ccggtctttc cgccatggtt gctttgtttt gctcaaggta tgcaagcacc   3180
gaaaggatat tctttgtcg caattgcgac ttggaataga gagaattggc gtctttgtcg   3240
actgcttgct tccagggctc ttgcgtttct ctcgcagacc acgtcgtttc aactgcagag   3300
atgtgttatc ttcagtaggt ggtctcgaag tcaaccctg cggatgacg taggaggtg   3360
caagagaggt aaaaaaaggc ctgatctcgg ggaggagagg acagggcact taggagccct   3420
tggagggaa gtcgagaaca ggcaacggat ggagggctgt cgctgtcgct ttggatggga   3480
caggcgcaaa gaaggttctt tcgaaccagc ccttaatta tttcaaccac actcccagc   3540
tttccgacgc gatggtatcg gccctccatt ggacatggga gcgggcgttt ggcggacgac   3600
gaggggcgtc cttatcagtt tccctcagt ttgccgggc ttgttttgca agatggggtc   3660
catctttccc ccacgctatg ccagggcatc atcccagtcg tgtgccctct gcaacggat   3720
ccccgccaaa atttttccttt ctggagggcc ggacttccc ggcagcagg cacggaaggc   3780
tagtttagag tcggcatgct cattggcctt cgagtccgag catggcccgc gggaccggga   3840
ttcacagctc ggttgaagga tgagcatgtg gtgtgcgaac caagtcgtgt tgctgatgat   3900
cccgtcgaa ttgtgtggtt ggttttcgtc ggcaaagggt tgctccgggg gcggctcttg   3960
```

```
gccgacgtga ggctgctacg gatacagtac atagtaggtt gttatctgcc ccagtgcttt   4020
cccgccccac ccagcatgcc tggaaatttc gtcatataca tacgagtacg gattacatac   4080
atacaaattc catccgaaga accctccatc tcatacttgt gtacacgtgc aatatcaatc   4140
gccccgagtc tcc                                                      4153

SEQ ID NO: 15          moltype = DNA   length = 8017
FEATURE                Location/Qualifiers
source                 1..8017
                       mol_type = genomic DNA
                       organism = Thermothelomyces heterothallicus
                       strain = C1
SEQUENCE: 15
agggtaggtg ggatgggcgg ggtgtagggt aggtcggtgt agggtaggtc ggctgggcgg     60
ggtgtagggt aggtcggttg ggcgggggtgt agggtaggtc ggttgggatg ggtgtagggt    120
aggtcggccg ggtgtagggt aggtcggctg ggcggggtgt agggtaggtc ggtgtagggt    180
aggtgggatg gggcgctatg tgcggccgcg agctcgcgag cccattttta gcgaaggcca    240
tacaaacgag ttttgcggaa cccgggattc accccccgaa gccgccggcg cgtgcgccc     300
gctgcgcatc ggtcggtggg tatatgagaa gggggcgggc aagccggaag ccagaggcaa    360
ctgctactgt tagctgccgc tggcctccgc ggcccagggc gcggcacggc tgcgttgaag    420
tctcccagtc tcccacccgt tggctgcgcg gatccgcccg tcttggtggt tgcgagctcg    480
cgagcccatt tttagcgaag gccatacaaa cgagttttgc ggggcccggg attccacccc    540
ggaaccccgcc ggcgcgtgcg ccccgctgcg catcggtcgg tgggtatgtg agggaggaag    600
aagaaaaaaa aaaaagctc ctgcgggggg gctgtcgggc acgcctactt tcggcgacc     660
cggcacctct ccgcggcagc cttcgcaggc cgctgttggt cccatttcat acgtcgccgc    720
cttcgcgtgg tgcctacgg tctgccgggg taccgacgat tgcggcgagc accgcctcag    780
caccgctgct gccaccggcg cgacctcgcc cgggggtgcg cggcatct gggaagactc     840
tgcaggcgta agggaatacc ccatgtgcgc cgagggggtgg gctatgtggg tgcttggcgg    900
ttcgccagac ctttctaaag ccaccgggg tacctaccgg ttgggacgc ctacagggct     960
gaacctcccg gtcgggcctc ctcttgggc gcttaggcgg cgacttcggg gcgcgatcgc   1020
tccccgctct cgcccgccga cggcgctctg gggaattcaa gagggggaaag cagatgtgac   1080
ccgcggctcg accggcgcat tgccggacga gctgcgcggc cacgcgggcc cccgcgcccc   1140
ccgacccagt aacttagtga actcttccgc cctgaaacac gggcggttgg ccctaaccgg   1200
ctcacgatag ttacctggtt gattctgcca gtagtcatat gcttgtctca aagattaagc   1260
catgcatgtc taagtataag caattataca gcgaaactgc gaatggctca ttaaatcagt   1320
tatcgtttat ttgatagtac cttactacat ggataaccgt ggtaattcta gagctaaatac   1380
atgctaaaaa tcccgacttc ggaagggatg tatttattag attaaaaacc aatgccctcc   1440
ggggctctct ggtgattcat gataaacttct cgaatcgcac ggccttgcgc cggcgatggt   1500
tcattcaaat ttctgcccta tcaactttcg acggctgggt cttggccagc cgtggtgaca   1560
acgggtaacg gagggttagg gctcgacccc ggagaaggag cctgagaaac ggctactaca   1620
tccaaggaag gcagcaggcg cgcaaattac ccaatcccga cacggggagg tagtgacaat   1680
aaatactgat acagggctct tttgggtctt gtaattggaa tgagtacaat ttaaatccct   1740
taacgaggaa caattggagg gcaagtctgg tgccagcagc cgcggtaatt ccagctccaa    1800
tagcgtatat taaagttgtt gaggttaaaa agctcgtagt tgaaccttgg gcctagccgg    1860
ccggtccgcc tcaccgcgtg cactggctcg gctgggtctt tccttctgga gaaccgcatg    1920
cccttcactg ggtgtgccgg ggaaccagga cttttactct gaacaaatta gatcgcttaa    1980
agaaggccta tgctcgaata cattagcatg gaataataga ataggacgtg tggttctatt    2040
ttgttggttt ctaggaccgc cgtaatgatt aatagggaca gtcggggggca tcagtattca    2100
attgtcagag gtgaaattct tggatttatt gaagactaac tactgcgaaa gcatttgcca    2160
aggatgtttt cattaatcag gaacgaaagt taggggatcg aagacgatca gataccgtcg    2220
tagtcttaac cataaactat gccgattagg gatcggacgg cgttatttt tgacccgttc    2280
ggcaccttac gataaatcaa aatgtttggg ctcctgggga agtatggtcg caaggctgaa    2340
acttaaagaa attgacgaaa gggcaccacc aggggtggag cctgcggctt aatttgactc    2400
aacacgggga aactcaccag gtccagacac gatgaggatt gacagattga gagctctttc    2460
ttgatttcgt gggtggtggt gcatggccgt tcttagttgg tggagtgatt tgtctgctta    2520
attgcgataa cgaacgagac cttaacctgc taaatagccc gtattgcttt ggcagtacgc    2580
cggcttcctta gagggactat cggctcaagc cgatggaagt ttgaggcaat aacaggtctg    2640
tgatgccctt agatgttctg ggccgcacgc gcgctacact gacagagcca gcgagtactc    2700
ccttggccga aaggcccggg taatcttgtt aaactctgtc gtgctgggga tagagcattg    2760
caattattgc tcttcaacga ggaatcccta gtaagcgcaa gtcatcagct tgcgttgatt    2820
acgtccctgc cctttgtaca caccgcccgt cgctactacc gattgaatgg ctcagtgagg    2880
ctttcggact ggcccagaga ggtcggcaac gaccactcag gccgaaaag ttatccaaac    2940
tcggtcattt agaggaagta aaagtcgtaa caaggtctcc gttggtgaac cagcggaggg    3000
atcattacag agctgcaaaa ctccctaaac catcgtgaac gctacctaga ccgttgcttc    3060
ggcggggcgg gccctcgcgc gccccccctg gggccgcac cgcgggccgc cgccggaggt    3120
acaccaaact cttgatatgt tatggccact ctgagtctcc tgtactgaat aagtcaaaac    3180
tttcaacaac ggatctcttg gttctggcat cgatgaagaa cgcagcgaaa tgcgataagt    3240
aatgtgaatt gcagaattca gtgaatcatc gaatctttga acgcacattg cgcccgccag    3300
catcctggcg gcatgcctg ttcgagcgtc atttcaacgc atcaagccca cggcttgtgt    3360
tggggacctg ccggtgcccg caggccctga aaaccagtgg cgctcgct agtcacacgg    3420
ggcgtagtag catacgacct cgctcagggc gtgctgcggg ttccagccgt aaaacgacct    3480
tcacaaccca aggttgacct cggatcaggt aggaggaccc gctgaactta agcatatcaa    3540
taagcggagg aaaagaaacc aacagggatt gccctagtaa cggcgagtga agcggcaaca    3600
gctcaaattt gaaatctggc ttcggcccga gttgtaattt gcagaggaag ctttaggcgc    3660
ggcaccttct gagtcccctg gaacggggcg ccatagaggg tgaagccc gtatagttgg    3720
atgcctagcc tgtgtaaagc tccttcgacg agtcgagtag tttgggaatg ctgctcaaaa    3780
tgggaggtaa atttcttcta aagctaaata ccggccagag accgatacg cacaagtaga    3840
gtgatcgaaa gatgaaaagc actttgaaaa gagggttaaa tagcacgtga aattgttgaa    3900
agggaagcgc ttgtgaccag acttgcgccg ggctgatcat ccgtgttct caccggtgca    3960
ctctgcccgg ctcaggccag catcggttct cgcgggggga taaaggcccg gggaatgtag    4020
```

```
ctcctccggg agtgttatag ccccgggtgt aatacccctcg cggggaccga ggttcgcgca    4080
tctgcaagga tgctggcgta atggtcatca gcgaccgcgtc ttgaaacacg gaccaaggag    4140
tcaaggtttt gcgcgagtgt ttgggtgtaa aacccgcacg cgtaatgaaa gtgaactag    4200
gtgagagctt cggcgcatca tcgaccgatc ctgatgtttt cggatggatt tgagtaggag    4260
cgttaagcct tggacccgaa agatgtgaa tatgcgtga atagggtgaa gccagaggaa      4320
actctggtgg aggctcgcag cggttctgac gtgcaaatcg atcgtcaaat ctgagcatgg    4380
gggcgaaaga ctaatcgaac catctagtag ctggttaccg ccgaagtttc cctcaggata    4440
gcagtgttgt cttcagtttt atgaggtaaa gcgaatgatt agggactcgg gggcgctttt    4500
tagccttcat ccattctcaa actttaaata tgtaagaagc ccttgttact tagttgaacg    4560
tgggccttcg aatgtatcaa cactagtggg ccattttttgg taagcagaac tggcgatgcg    4620
ggatgaaccg aacgcggggt taaggtgccg gagtggacgc tcatcagaca ccacaaagg    4680
cgttagtaca tcttgacagc aggacggtgg ccatggaagt cggaatccgc taaggactgt    4740
gtaacaactc acctgccgaa tgtactagcc ctgaaaatga tggcgctca agcgtccac     4800
ccatacccg ccctcagggt agaaacgacg ccctgaggag taggcggccg tggaggtcga   4860
tgacaagcc tagggcgtga gcccgggtcg aacggcctct agtgcagatc ttggtggtag    4920
tagcaaatac ttcaatgaga acttgaagga ccgaagtggg gaaaggttcc atgtgaacag    4980
cggttggaca tgggttagtc gatcctaagc catagggaag ttccgtttca aaggggcact    5040
cgtgccccgt gtggcgaaag ggaagccggt taacattccg gcacctggat gtgggttttg    5100
cgcggtaacg caactgaacg cggagacgac ggcggggggcc ccgggcagag ttctcttttc    5160
ttcttaacgg tctatcaccc tggaaacagt ttgtctggag atagggttta acggccggaa    5220
gagcccgaca cttctgtcgg gtccggtgcg ctctcgacgt cccttgaaaa tccgcgggag    5280
ggaataattc tcacgccagg tcgtactcat aaccgcagga ggtccccaag gtgaacagcc    5340
tctggttgat agaacaatgt agataaggga agtcggcaaa atagatccgt aacttcggga    5400
taaggattgg ctctaagggt tgggcacgtt gggctttggg cggacgccct gggagcaggt    5460
cgcctctagc cgggcaaccg gcgggggct tccagcatcc gggtgcagat gcccttagca    5520
ggcttcggcc gtccggcgcg cggttaacaa ccaacttaga actggtacgg acaggggaa    5580
tctgactgtc taattaaaac atagcattgc gatggccaga aagtggtgtt gacgcaatgt    5640
gatttctgcc cagtgctctg aatgtcaaag tgaagaaatt caaccaagcg cgggtaaacg    5700
gcgggagtaa ctatgactct cttaaggtag ccaaatgcct cgtcatctaa ttagtgacgc    5760
gcatgaatgg attaacgaga ttcccactgt ccctatctac tatctagcga aaccacagcc    5820
aagggaacgg gcttggcaga atcagcgggg aaagaagacc ctgttgagct tgactctagt    5880
ttgacattgt gaaagacat aggaggtgta gaataggtgg gagcttcggc gccggtgaaa     5940
taccactact cctattgttt ttttacttat tcaatgaagc ggggctggat tttcgtccaa    6000
cttctggttt taaggtcctt cgcggaccga cccgggttga agacattgtc aggtggggag    6060
tttggctggg gcggcacatc tgttaaacca taacgcaggt gtcctaaggg gggctcatgg    6120
agaacagaaa tctccagtag aacaaaaggg taaaagtccc cttgattttg attttcagtg    6180
tgaatacaaa ccatgaaagt gtggcctatc gatcctttag tccctcgaaa tttgaggcta    6240
gaggtgccag aaaagttacc acagggataa ctggcttgtg cggcaagc gttcatagcg     6300
acgtcgcttt ttgatccttc gatgtcggct cttcctatca taccgaagca gaattcggta    6360
agcgttggat tgttcaccca ctaataggga acgtgagctg ggtttagacc gtcgtgagac    6420
aggttagttt taccctactg atgaactcat cgcaatggta attcagctta gtacgagagg    6480
aaccgctgat tcagataatt ggttttttgcg gttgtccgac cgggcagtgc cgcgaagcta    6540
ccatctgctg gataatggct gaacgcctct aagtcagaat ccatgccaga acgcgatgat    6600
actacccgca cgttgtagac gtataagaat aggctccggc ctcgtatcct agcaggcgat    6660
tcctccgccg gcctcgaagt tggccggcgg taattcgcgt attgcaattt cgacacgcgc    6720
gggatcaaat ccttttgcaga cgactagat gtgcaaagg gtcctgtaag cagtagagta     6780
gccttgttgt tacgatctgc tgagggtaag ccctccttcg cctagatttc ccagcgagag    6840
cccgccggcg gaacagccgg gcgagcctta cggggaagc cttaagggga ttgagaagtg    6900
gtgccgtgcg ttcgcgcgcc cctaggtcct ttagccggcc gcaggtgtag ggtaggtcgg    6960
ttgggaggat ggggtgtagg gtaggtcggt gtagggtagg ttggttggga ggatggggtg    7020
tagggtaggt cggccgggtg tagggtaggt cggtgtaggg taggtgggg gggcgctat      7080
atgcggccgc gagctcgcga gcctattttt agtgaaggct atataaataa gctttacgtt    7140
accgggcctt gctaccctcg agtggcgtgg gccgtgctgc ctactgggca ttgctcgccg    7200
ggctgtataa gggaggggtc ggggtcgcgg tctaggtag gtcgggtggg atggggtgta    7260
gggtaggaga agcgctctag tcgtgtgtct ttttctctag gtcttattatt agtactggct    7320
gtagggcgac gtgccctgcc ttgttataat attatattgt atgtttaggc ctatactagc    7380
ttgtaatcta tttgtatctg gcttattagg tacggcttcc ttttgtatata actagagagg    7440
ctctggtatg cttcttagta tagcggtata ggattcataa tcatagtaat gataatcata    7500
atagtaataa taataataat agtaatgata ataataataa tctatttata tcttatttaa    7560
aatgcttgta cggctgcctg ctcttaagga gtagctagat atgagatggt agggtagcta    7620
gctaacctag gctagacgtt ctcgtccctt agctatataa gtgctatata ttatagttag    7680
ttatctaacc taccttctta cttgagcaga agaggtaggg ttctagtata gctagtaggg    7740
cttctaggcc taagggcctg ttattcgagt tattataggt agtatttaa tatagttata    7800
gggataggcc tcgattacgg gtataggata ggtaggata gtataggtta ggtcggttaa    7860
gaggataggg tgtaaggtag gtcggccggg tataggtag gtagtaggtt aggcgggtg     7920
tagggtaggt cggtgtaggg taggtgggat gggcggggtg tagggtaggt cggttgggag    7980
gatgggtgt agggtaggtc ggtgtagggt aggtcgg                              8017

SEQ ID NO: 16       moltype = RNA   length = 894
FEATURE             Location/Qualifiers
source              1..894
                    mol_type = genomic RNA
                    organism = Thermothelomyces thermophilus
SEQUENCE: 16
atgattgaaa ttcctctgga tcacggctcg ttagagcacc tcctcccagc ctcgtggaag     60
tcccaggtca ccgcctggct cgccgaggac acgcccctcct tcgacgtggg gggcttcgtc   120
gttgcgcgatc acccacgcac ggcgacgctc tgggcaagt catccggcat cctcgccggc   180
gtccccttct tcaacgaggt gttcgcccaa tgcgggtgca cggtcgaatg gcacgcccgc   240
gagggggtcgc acatcgagtc gcacggtgac aagacgcgcg tggcgaccgt caagggcccc   300
```

```
gcgcgaggca tcctggaggg cgagcgggtg gccctcaaca tcttggcgcg gtgctctggc  360
attgcgacga tgagccgcag gctgctggtc aacctgcgta gcgccggctg cagggcact   420
ctggcaggca cgcggaagac gacgcccggc ttccggctcg tggagaagta cggcatgctg  480
gtcggcggcg ccgatactca tcggatggat ctgagcacaa tgaccatgct caaagataac  540
cacgtgtgga gccgcgggag catcacccag gcagtcaagc ctgccaaggc cgcgggggga  600
ttcagcttga aggtcgaggt cgaggtacaa agcgaggagg aggctgacga ggcattgcc   660
gccggcgccg atatcgtcat gctcgacaat ttcaccggag aaggcgtcaa ggccacgtcg  720
cggagcctca aggagaagtg gaaggggaaa agcagttcc tgctcgaggt ctcggggggg   780
ctgagcgagg ataatgctga actctacatc tgcaacgatg tcgacattct ctcgacaagc  840
tccattcacc agggtgtacg ccacatcgac ttctctctca agatcaatgt gtga         894
```

```
SEQ ID NO: 17              moltype = RNA    length = 894
FEATURE                    Location/Qualifiers
source                     1..894
                           mol_type = genomic RNA
                           organism = Thermothelomyces thermophilus
SEQUENCE: 17
atgtcgactg gatctagcga ttccggcact caaacgccct cggcgaccgt ggagcaaccg   60
aacctcaatg gcgctcagca gtcctacact tttccaaccg aaaagctgaa gcgccgccaa  120
acacagcctg ggaagacacc cctcgtgctg gtggcctgcg ggtcgttctc tccaataacc  180
ttcctccacc tccgcatgtt cgagatggca agcgactttg tccggttcaa caccgacttc  240
gaagtgtgcg gcggatatct gtcaccggtc agcgacgctt acaagaaggt ggggctagcg  300
cccggcgtcc accgggtcaa tatgtgcgcg agagccgtcg agcagtcgtc ctggctcatg  360
gtcgacccgt acgagacggt caattgtgac gaaaaggggg agccgcgata cgtgccgacc  420
gccaaggtct tgcgccactt tgattacgaa atcaatgaag tgctcggagg tatcgagggc  480
acagatgggc agagaaagaa ggctcggatt gcgcttctgg ctggcgccga cttggtcatg  540
tctatgggtg agcctgggct ttgggcacca aaggatctcg atacgatcct cggccagtac  600
ggcgctttca tcatcgagcg ctccgggacg gatatcgacg aggctctcgc ctccctcagg  660
cagtatgagc acaacatttg ggtgatcagc caggtcatcc agaacgacat cagctctact  720
aaggttcggc tgttcttgaa gaaggaccttt agtgtcaggt acctgattcc ggatcccgtc  780
gtcgagtaca tcgaggaaca cggcctgttt tcggaaccca gcgcgaacaa gtcctaggagc  840
cggacaccgg atgttgcttc tgggccttca gacaacaagc ctaccaaggg ctga         894
```

```
SEQ ID NO: 18              moltype = RNA    length = 2037
FEATURE                    Location/Qualifiers
source                     1..2037
                           mol_type = genomic RNA
                           organism = Thermothelomyces thermophilus
SEQUENCE: 18
atgggtcatc tcgtgacggt tgcgacatgt agcttgaacc aatggggttct cgattgggaa   60
gggaaccttg cccgtatcat cgagagcatc caccaggcaa aggcggccgg tgcacgactc  120
cgcgttgggc ctgaactcga aatctgcggg tactcgagcc tggatcactt tcacgagctc  180
gatgtttaca cgcacagcct ggagatgctc cgccagctcc tgctggacaa gagcactcat  240
ggcatcctcc tcgacatcgg catgcccatc cttcaccgga acctcaggta caactgccga  300
gtcatctgcc tcgacggcaa gatcctcctg atcaggccca agatgtggct cgccaacgac  360
ggtaactacc gcgagatgag gcatttcacc ccctggatgc gcccgcggga gacggagttc  420
ttccacctgc ccaagatgct ggccgagctgc caggagaga ctcacgtcct ctttggcgat   480
gctgtcatct ccaccccgca gaccgccttt ggcgccgaga cgtgcgagga gctcttcacg  540
cccaaagctc cacatatcga catggcgcta gacggtgttg agatcatcac caactcgagc  600
ggcagccact tcacctgcg gaaactcgac acccgcctgc aattgatcac cgaggctacc  660
cgtaagtctg gtggcgtcta cctgtacgcg aaccagcaag gctcgacgg cgggctgcag   720
tactttgacg gttgtgccat gatcattgtg aacggcgatg ttgtcgccca ggggtctcag  780
ttcagcctca atgacgtcga ggtcgtgacc gccacggtcg atctcgagga agtgcggtcc  840
taccgcgctg ccatctctcg tgccatgcaa gcggccgcgt ccacggccaa gtatcagagg  900
atccagaccc cgttcgagct cagctccgaa gccgacgact ccgatgtcag caaggcgcca  960
actctgccca tccagccacg gttccactcg gttgaggagg agattgccct ctgcggcggc 1020
tgctatcttt gggattacct ccgccggtcc ggccgccgcag gttatctggt gccctgagc  1080
gggggatc actcgtgtgc gactgcagtg gtcgtctact ccatgtgccg catcgtgatg  1140
caagccgtcg agcaaggaaa ccaacaggtc atcgacgacg tcaagcgcat cgccagatac 1200
ggcgcgagg gcgtcctgcc caagacggcc caggaactct gcaaccaggt cttccaccacc 1260
atctacatgg gcatgaggaa gcagagctcg cgcgagaccc gccagcgcgc caaggacctc 1320
tccgaggcca tcggcagcta ccacgtcaac ctcgacatcg atgacgagtt cggtcagatt 1380
ctgcccacgg cgagggggag gcccggaggt ggaagtctgc tgattcttgg cagtgcgaat 1440
gtcggcgagg tgagcctcag gggctacttg accaagtacg actgctcgag cgctgatatc 1500
aaccccatcg gctctatcag caaggccgat ctgaagcgct tcatcgcatg gccgagaag  1560
agctttgatc tgccatgcct ccatgactt ctgacggctg tccccaccgc cgagctcgag  1620
cccatcacgc aagactacgt gcagagcgac gaagcagaca tggcatgac ataccaggaa  1680
ctgaccatct ttggtcgact gcgcaagctc aacaagctgg tcctttttgg catgttccag  1740
cgccttgtgc acgactggag catcgaccgc gagcgcaagc cggacgacga cgcaccgtac  1800
tatacgccgg cacaggtcgc cgagaaggtc aagaagttct tccactatta tgccatcaac  1860
aggcataaga tgaccacact gacgcccgcc ctgcattgca acgactactc gcccgacgac  1920
aaccgctttg atctgcgccc cttcctgtat ccgcccttct ggaagagctg gagcttcaag  1980
cggatcgaca tggagcttga aaagattgag aagaagcggg ccagcaagaa acagtga     2037
```

```
SEQ ID NO: 19              moltype = RNA    length = 1308
FEATURE                    Location/Qualifiers
source                     1..1308
                           mol_type = genomic RNA
                           organism = Thermothelomyces thermophilus
```

```
SEQUENCE: 19
atgaccaccc gttatcgcgt tgaatatgct ctcaaaactc accgccgtga tcaattcata   60
gaatggatca agggcctgct ggcagtgcca ttcgtgctgt attcgcagcc tcacggagcc  120
atcgaccggc agggcacggt aaacctatct cagacacgcg aggaagcaca tcggagatac  180
agcgaaattc tgcgcgatgt cgagggcatg atcgacgacc acattgccca ccagaacgac  240
cccgagaatc cattcccgtc gaaactcaag ctcctggtcc ccagcatcgg gcccttcttc  300
actcgactac ccctagaggc cgccttcaaa tatcaggaca gcaagcgtta catctcctcc  360
cgccgcttcg tctcccccctc cttcaatgac gtccgcctca tcctcaactc ggcccaaatg  420
atggccgtga caacatacgg caccctccag ctagccacct tcgatggtga cgtgaccctc  480
tacgaagacg ggcaaagcct cgaaccaacc agcccatcg tcccgcggct gatcgacctc  540
ctccgcaaaa acgtaaagat tggcatcgtc accgcggcag gctacacaac cgccgacaaa  600
tactacgccc gcctgcacgg actcctcgac gcgctggcca gcacgaccga gctaaacccc  660
tcccaaaagc aatccctcat cgtcatgggc ggagaagcga actacctctt cgagttctcg  720
ccttcgtccc cgcacctctt ggccccccgtc ccgcgcgaga agtggctgac cccggaaatg  780
gccgcctggg atgaccgcga catcgcccaa gtgctcgacg tcgccgaggc ggccctgcgc  840
gactgcgtcc ggaccctcaa cctgccggcc gtgctgatgc gcaaggaccg cgccgtcggc  900
atcgtcccga acccgcccga gacgcgcatc ccgcgcgagt cgctcgagga cgggtcctg   960
gtggtgcaga agacgctgga gctcagcgcg gcagggcggg cccgccgcgt gcccttctgc 1020
gccttcaacg gcgggcgcga cgtctttgtc gatatcggcg acaagagctg gggcgtgacg 1080
gtgtgccagc gctggttcgg atcttcgtcc gagccgagca gaggcaaggg cgaaggcggc 1140
gcaatcaagg ggcagaacac gctgcacgta ggcgaccagt tcctgagcgc aggggcgaat 1200
gatttccggg cgaggagcgt cggcacgacg gcgtggatcg cgagcccggc agagacggtc 1260
gacctgctcg acgagttggc cgagttgatg gagaagaggg cgtcttag               1308

SEQ ID NO: 20           moltype = RNA   length = 717
FEATURE                 Location/Qualifiers
source                  1..717
                        mol_type = genomic RNA
                        organism = Thermothelomyces thermophilus
SEQUENCE: 20
atgggttgcg ctaccaacgg ggtttccccc cgcaaagtct tcttttttcga cattgacaat   60
tgtctctatc cgaggagcac caaggtacac gacctaatgg ccgatctcat cgacaaatac  120
tttgccacgc acctctcact gccctgggag gatgcagtgc ggttacacaa ggaatactac  180
cagaactacg gtctcgccat tgagggcctg gtacggcacc atcagatcga cccccctagac 240
tacaacgcca aggtcgacga cgccctcccg ctggacgacg tcatcaaacc ccggccagag  300
ctcaagaagc tgcttggcga cattgaccag agcaaggtca agctgtggct cttcaccaat  360
gcctacatca accacgccaa gcgagttgtt cgcttactcg aagtcgagga gttcttcgag  420
ggggtcacat actgcgacta cagctccgtg cccttcacct gcaagcccca gcccgccatg  480
taccagaagg cgatgcgtga ggccggggtg gagagatatg aagactgctt ctttgtcgat  540
gattcgtacc aaaattgcaa aaaggcgcag gaactcgggt ggaccgtcgc ccacctcgtc  600
gaggacggtg tcaaaccacc aaagactcca gcctgcaaat tccagatcag gcatctggac  660
gacctacgca cagtcttccc gcagtgtttc aagggaagcg cctcggaagg tagctga     717
```

NICOTINAMIDE RIBOSIDE PRODUCTION IN FILAMENTOUS FUNGI

CROSS-REFERENCE TO RELATED APPLICATIONS

This application is the U.S. Continuation of International Patent Application No. PCT/IB2021/053565, filed on Apr. 29, 2021, which claims the benefit of and priority to U.S. Provisional Patent Application No. 63/017,668, filed on Apr. 30, 2020, the contents of each of which are hereby incorporated by reference in their entireties.

INCORPORATION-BY-REFERENCE OF MATERIAL ELECTRONICALLY FILED

The official copy of the sequence listing is submitted electronically in ST.26 XML format having the file name "15872-594USCON_SeqList" submitted on Feb. 28, 2023, and having a size of 56,378 bytes, and is filed concurrently with the specification. The Sequence Listing ST.26 XML file is part of the specification and is herein incorporated by reference in its entirety.

FIELD OF THE INVENTION

The present invention relates to genetically modified ascomycetous filamentous fungi, in particular of the species *Thermothelomyces heterothallica* (formerly *Myceliophthora thermophila*), in which at least one of the enzymes involved in the nicotinamide riboside biosynthesis pathway has been engineered to increase the production of nicotinamide riboside and/or its precursors.

BACKGROUND OF THE INVENTION

Nicotinamide riboside (NR) is a new form of vitamin $B_3$ that functions as a precursor to nicotinamide adenine dinucleotide (NAD), a key player in the cellular production of energy. NAD oxidized form ($NAD^+$) participates in a host of metabolic pathways and is involved in other important processes, such as DNA repair. $NAD^+$ levels naturally decline as people and animals age, and this loss has been proposed as contributing to the underlying physiology of aging. Clinical studies have shown that NR can significantly increase levels of $NAD^+$ and some of its associated metabolites in both whole blood and peripheral blood mononuclear cells. NR is converted into $NAD^+$ through two distinct pathways. The first pathway utilizes the NR kinase, NRK1, to produce nicotinamide mononucleotide (NMN), which is then converted into $NAD^+$. The second pathway cleaves NR into nicotinamide (Nam) and a ribose, by exploiting two independently acting enzymes uridine hydrolase 1 (URH1) and purine nucleoside phosphorylase (PNP1).

Wild type *Thermothelomyces heterothallica* (*Th. heterothallica*) C1 (recently renamed from *Myceliophthora thermophila*, which in turn was renamed from *Chrysosporium lucknowense*) is a thermotolerant ascomycetous filamentous fungus producing high levels of cellulases, which made it attractive for production of these and other enzymes on a commercial scale.

For example, U.S. Pat. Nos. 8,268,585 and 8,871,493 to the Applicant of the present invention disclose a transformation system in the field of filamentous fungal hosts for expressing and secreting heterologous proteins or polypeptides. Also disclosed is a process for producing large amounts of polypeptides or proteins in an economical manner. The system comprises a transformed or transfected fungal strain of the genus *Chrysosporium*, more particularly of *Chrysosporium lucknowense* and mutants or derivatives thereof. Also disclosed are transformants containing *Chrysosporium* coding sequences, as well expressing-regulating sequences of *Chrysosporium* genes.

Wild type C1 was deposited in accordance with the Budapest Treaty with the number VKM F-3500 D, deposit date Aug. 29, 1996. High Cellulase (HC) and Low Cellulase (LC) strains have also been deposited, as described, for example, in U.S. Pat. No. 8,268,585.

Recently, the Applicant of the present has shown that filamentous fungi, particularly *Th. heterothallica* is highly suitable for the production of secondary metabolites. International (PCT) Application Publication No. WO 2020/161682 discloses that *Th. heterothallica* is capable of producing cannabinoids and precursors thereof, particularly of producing cannabigerolic acid (CBGA) and/or cannabigerovarinic acid (CBGVA) and products thereof, including tetrahydrocannabinolic acid (THCA), cannabidiolic acid (CBDA) and cannabidivarinic acid (CBDVA), and use thereof for producing said precursors and cannabinoids.

U.S. Pat. No. 8,114,626 discloses fungal strain, particularly *Saccharomyces* strain deficient in nicotinamide riboside import and salvage and use thereof for producing nicotinamide riboside. Methods for producing nicotinamide riboside and a nicotinamide riboside-supplemented food product using the strain of the invention are also provided.

WO 2018/211028 discloses microbial production of nicotinamide riboside and/or nicotinamide mononucleotide using a genetically modified fungus.

There remains a need for a system for producing high amounts of nicotinamide riboside for use in the pharmaceutical industry in an efficient and cost-effective way.

SUMMARY OF THE INVENTION

The present invention provides genetically modified ascomycetous filamentous fungi capable of producing nicotinamide riboside (NR) and precursors thereof. In particular, the present invention provides *Thermothelomyces heterothallica* strain C1 as an exemplary ascomycetous filamentous fungus genetically modified to enhance the production of nicotinamide riboside. The fungi described herein have been modified to increase the flux of the NR metabolic pathway.

The yeast *Saccharomyces* is currently the major candidate for the production of nicotinamide riboside in microorganisms. Surprisingly, the present invention shows that *Th. heterothallica*, exemplifying ascomycetous filamentous fungi, can be genetically modified to significantly increase the outcome of the endogenous pathways naturally producing NR, while blocking natural NR catabolism. The present invention shows that combination of overexpressing enzymes involved in the NR biosynthesis pathway and optionally the blocking of catabolism and/or cellular uptake of NR significantly increases the production of NR. Advantageously, a large portion of the NR is secreted and accumulated in the growth medium, enabling simple recovery and purification procedures. Moreover, the genetically modified ascomycetous filamentous fungus according to the invention significantly increases the ratio of NR to other metabolites, such as nicotinic acid ribose and nicotinic acid, which further simplifies the purification procedure.

The exemplary *Th. heterothallica* C1 system of the present invention was engineered for production of NR by overexpressing five genes encoding enzymes involved in conversion of quinolinate intermediate to NR (BNA6, NMA1, QNS1, ISN1, and SDT1) and by deleting four genes encoding enzymes that catabolize NR (NRK1, PNP1, and URH1) or that transport excreted NR back into the cells (NRT1). The genetically modified fungi described herein produced 10-20 times more NR compared to their parent strains. Without wishing to be bound by any specific theory or mechanism of action, diverting the resources of the fungus by methods of metabolic engineering increases the potential of this strain to become a more efficient host for production of NR compared to, for example, *S. cerevisiae*.

Furthermore, several *Th. heterothallica* C1 strains developed by the Applicant of the present invention are less sensitive to feedback repression by glucose and other fermentable sugars present in the growth medium as carbon source than conventional yeast strains and also most other ascomycetous filamentous fungal hosts, and consequently can tolerate higher feeding rate of the carbon source, leading to high yields production by these fungi.

In addition, some of the *Th. heterothallica* C1 strains developed by the Applicant of the present invention can be grown in liquid cultures with significantly reduced medium viscosity in fermenters, compared to most other ascomycetous filamentous fungal species. The low viscosity cultures of *Th. heterothallica* C1 are comparable to that of *S. cerevisiae* and other yeast species. The low viscosity may be attributed to the morphological change of the strain from having long and highly interlaced hyphae in the parental strain(s) to short and less interlaced hyphae in the developed strain(s). Low medium viscosity is highly advantageous in large scale industrial production.

According to an aspect of the present invention there is provided a genetically modified ascomycetous filamentous fungus for producing nicotinamide riboside or a precursor thereof, the genetically modified filamentous fungus comprises at least one cell comprising at least one exogenous polynucleotide selected from the group consisting of (i) an exogenous polynucleotide encoding Nicotinate-nucleotide pyrophosphorylase (BNA6); (ii) an exogenous polynucleotide encoding Nicotinamide Mononucleotide Adenylyltransferase (NMA1); (iii) an exogenous polynucleotide encoding glutamine (Q) dependent Nad$^+$ synthetase (QNS1); (iv) an exogenous polynucleotide encoding Inosine 5'-monophosphate (IMP)-specific 5'-nucleotidase (ISN1); and (v) an exogenous polynucleotide encoding pyrimidine nucleotidase (SDT1).

According to some embodiments, the NR precursor is nicotinamide adenine dinucleotide (NAD) or nicotinamide mononucleotide (NMN).

According to some embodiments, the genetically modified ascomycetous filamentous fungus comprises at least one cell comprising a plurality of exogenous polynucleotides encoding for at least two different proteins selected from the group consisting of BNA6, NMA1, QNS1, ISN1, and SDT1. According to certain embodiments, the genetically modified ascomycetous filamentous fungus comprises at least one cell comprising a plurality of exogenous polynucleotides encoding for at least three different proteins selected from the group consisting of BNA6, NMA1, QNS1, ISN1, and SDT1. According to certain embodiments, the genetically modified ascomycetous filamentous fungus comprises at least one cell comprising a plurality of exogenous polynucleotides encoding for at least four different proteins selected from the group consisting of BNA6, NMA1, QNS1, ISN1, and SDT1. According to specific embodiments, the genetically modified ascomycetous filamentous fungus comprises at least one cell comprising a plurality of exogenous polynucleotides encoding for BNA6, NMA1, QNS1, ISN1, and SDT1.

According to some embodiments, the polynucleotide encodes an enzyme that is endogenous to the genetically modified ascomycetous filamentous fungus.

According to some embodiments, the polynucleotide is endogenous to the genetically modified ascomycetous filamentous fungus. According to other embodiments, the polynucleotide is heterologous to the genetically modified ascomycetous filamentous fungus.

According to certain exemplary embodiments, the polynucleotides of the present invention are designed based on the amino acid sequence of the enzyme to be produced employing a codon usage of a filamentous fungus.

According to some embodiments, the BNA6 protein comprises an amino acid sequence having at least 75%, or at least 80%, or at least 85%, or at least 90%, or at least 95%, or at least 99%, or 100% identity to the amino acid sequence of *Thermothelomyces heterothallica* BNA6. According to certain embodiments, the *Thermothelomyces heterothallica* BNA6 comprises the amino acids of SEQ ID NO: 1.

According to some embodiments, the exogenous polynucleotide encoding BNA6 comprises a nucleotide sequence having at least 60%, 65%, 70%, 75%, 80%, 85%, 90%, 95%, 98%, or 100% identity to the nucleotide sequence of *Thermothelomyces heterothallica* bna6. According to some embodiments, the *Thermothelomyces heterothallica* bna6 comprises the nucleotide sequence of SEQ ID NO: 2.

According to some embodiments, the NMA1 protein comprises an amino acid sequence having at least 75%, or at least 80%, or at least 85%, or at least 90%, or at least 95%, or at least 99%, or 100% identity to the amino acid sequence of *Thermothelomyces heterothallica* NMA1. According to certain embodiments, the *Thermothelomyces heterothallica* NMA1 comprises the amino acids of SEQ ID NO: 3.

According to some embodiments, the exogenous polynucleotide encoding NMA1 comprises a nucleotide sequence having at least 60%, 65%, 70%, 75%, 80%, 85%, 90%, 95%, 98%, or 100% identity to the nucleotide sequence of *Thermothelomyces heterothallica* nma1. According to some embodiments, the *Thermothelomyces heterothallica* nma1 comprises the nucleotide sequence of SEQ ID NO: 4.

According to some embodiments, the QNS1 protein comprises an amino acid sequence having at least 75%, or at least 80%, or at least 85%, or at least 90%, or at least 95%, or at least 99%, or 100% identity to the amino acid sequence of *Thermothelomyces heterothallica* QNS1. According to certain embodiment, the *Thermothelomyces heterothallica* QNS1 comprises the amino acids of SEQ ID NO: 5.

According to some embodiments, the exogenous polynucleotide encoding QNS1 comprises a nucleotide sequence having at least 60%, 65%, 70%, 75%, 80%, 85%, 90%, 95%, 98%, or 100% identity to the nucleotide sequence of *Thermothelomyces heterothallica* qns1 . According to some embodiments, the *Thermothelomyces heterothallica* qns1 comprises the nucleotide sequence of SEQ ID NO: 6.

According to some embodiments, the ISN1 protein comprises an amino acid sequence having at least 75%, or at least 80%, or at least 85%, or at least 90%, or at least 95%, or at least 99%, or 100% identity to the amino acid sequence of *Thermothelomyces heterothallica* ISN1. According to certain embodiments, the *Thermothelomyces heterothallica* ISN1 comprises the amino acids of SEQ ID NO: 7.

According to some embodiments, the exogenous polynucleotide encoding ISN1 comprises a nucleotide sequence having at least 60%, 65%, 70%, 75%, 80%, 85%, 90%, 95%, 98%, or 100% identity to the nucleotide sequence of *Thermothelomyces heterothallica* isn1. According to some embodiments, the *Thermothelomyces heterothallica* isn1 comprises the polynucleotide SEQ ID NO: 8.

According to some embodiments, the SDT1 protein comprises an amino acid sequence having at least 75%, or at least 80%, or at least 85%, or at least 90%, or at least 95%, or at least 99%, or 100% identity to the amino acid sequence of *Thermothelomyces heterothallica* SDT1. According to certain embodiments, the *Thermothelomyces heterothallica* SDT1 comprises the amino acids of SEQ ID NO: 9.

According to some embodiments, the exogenous polynucleotide encoding SDT1 comprises a nucleotide sequence having at least 60%, 65%, 70%, 75%, 80%, 85%, 90%, 95%, 98%, or 100% identity to the nucleotide sequence of *Thermothelomyces heterothallica* sdt1. According to some embodiments, the *Thermothelomyces heterothallica* sdt1 comprises the nucleotide sequence of SEQ ID NO: 10.

According to some embodiments, the genetically modified ascomycetous filamentous fungus expresses elevated amounts of at least one protein selected from the group consisting of BNA6, NMA1, QNS1, ISN1, and SDT1 compared to the non-modified strain. Each possibility represents a separate embodiment of the present invention.

According to some embodiments, the genetically modified ascomycetous filamentous fungus further comprises at least one cell having reduced expression and/or activity of at least one protein or enzyme that catabolize NR, modify NR or transport NR into the cells' cytoplasm.

According to some embodiments, the genetically modified ascomycetous filamentous fungus comprises at least one cell having reduced expression and/or activity of at least one protein or enzyme selected from the group consisting of Nicotinamide riboside kinase 1 (NRK1), Uridine hydrolase 1 (URH1), Purine nucleoside phosphorylase (PNP1), and Nicotinamide riboside transporter 1 (NRT1). According to certain embodiments, the genetically modified ascomycetous filamentous fungus comprises at least one cell having reduced expression and/or activity of at least two different proteins or enzymes selected from the group consisting of NRK1, URH1, PNP1, and NRT1. According to certain embodiments, the genetically modified ascomycetous filamentous fungus comprises at least one cell having reduced expression and/or activity of at least three different proteins or enzymes selected from the group consisting of NRK1, URH1, PNP1, and NRT1. According to certain embodiments, the genetically modified ascomycetous filamentous fungus comprises at least one cell having reduced expression and/or activity of NRK1, URH1, PNP1, and NRT1. According to some embodiments, the genetically modified ascomycetous filamentous fungus expresses reduced amounts of at least one protein selected from the group consisting of NRK1, URH1, PNP1, and NRT1, compared to the non-modified strain. Each possibility represents a separate embodiment of the invention.

According to some embodiments, the genetically modified ascomycetous filamentous fungus comprises at least one deleted or disrupted gene selected from the group consisting of nrk1, urh1, pnp1, and nrt1. Each possibility represents a separate embodiment of the invention.

According to certain embodiments, the genetically modified ascomycetous filamentous fungus comprises at least one cell comprising at least one exogenous polynucleotide encoding a protein selected from the group consisting of BNA6, NMA1, QNS1, ISN1, and SDT1 and reduced expression and/or activity of at least one protein or enzyme selected from the group consisting NRK1, URH1, PNP1, and NRT1.

According to some embodiments, the genetically modified ascomycetous filamentous fungus is capable of producing an elevated amount of NR, compared to the non-modified fungus.

According to some embodiments, the genetically modified ascomycetous filamentous fungus is capable of producing higher NR amount compared to the produced amount of nicotinic acid ribose (NAR). According to certain embodiments, the genetically modified ascomycetous filamentous fungus is capable of producing at least twice the amount of NR compared to NAR.

According to some embodiments, the genetically modified ascomycetous filamentous fungus is capable of producing higher NR amount compared to the produced amount of nicotinic acid (NA). According to certain embodiments, the genetically modified ascomycetous filamentous fungus is capable of producing at least twice the amount of NR compared to nicotinic acid.

According to some embodiments, the genetically modified ascomycetous filamentous fungus produces nicotinamide ribose in an increased amount compared to the amount produced in a corresponding unmodified ascomycetous filamentous fungus cultured under similar conditions. According to certain embodiments, the genetically modified ascomycetous filamentous fungus is capable of producing at least 5 times more NR compared to its parent strain. According to certain embodiments, the genetically modified ascomycetous filamentous fungus is capable of producing at least 10 times more NR compared to its parent strain.

According to some embodiments, the genetically modified ascomycetous filamentous fungus is capable of increasing the amount of secreted nicotinamide ribose in the growth medium by at least 2, 5, or 10 compared to a non-genetically modified ascomycetous filamentous fungus.

According to some embodiments, the genetically modified ascomycetous filamentous fungus is capable of producing at least 10 mg NR/L growth medium. According to some embodiments, the genetically modified ascomycetous filamentous fungus is capable of producing at least 15 mg NR/L growth medium. According to certain embodiments, at least 70%, 80%, or 90% of the produced NR is secreted NR.

The polynucleotides encoding each of the proteins or enzymes may form part of one or more DNA constructs and/or expression vectors. According to certain embodiments, each of the polynucleotide forms part of a separate expression DNA construct/vector. According to other embodiments, part or all the polynucleotides are present within the same DNA construct/expression vector.

According to some embodiments, the at least one exogenous polynucleotide is a

DNA construct or an expression vector further comprising at least one regulatory element operable in said ascomycetous filamentous fungus. According to certain embodiments, the regulatory element is selected from the group consisting of a regulatory element endogenous to said fungus and a regulatory element heterologous to said fungus.

According to some embodiments, the ascomycetous filamentous fungus is of a genus within the group *Pezizomycotina*.

According to some embodiments, the ascomycetous filamentous fungus is of a genus selected from the group consisting of *Thermothelomyces, Myceliophthora, Trichoderma, Aspergillus, Penicillium, Rasamsonia, Chrysosporium, Corynascus, Fusarium, Neurospora,* and *Talaromyces*.

According to some embodiments, the ascomycetous filamentous fungus is of a species selected from the group consisting of *Thermothelomyces heterothallica* (also denoted *Myceliophthora thermophila*), *Myceliophthora lutea, Aspergillus nidulans, Aspergillus funiculosus Aspergillus niger, Aspergillus oryzae, Trichoderma reesei, Trichoderma harzianum, Trichoderma longibrachiatum, Trichoderma viride, Rasamsonia emersonii. Penicillium chrysogenum, Penicillium verrucosum, Sporotrichum thermophile, Corynascus fumimontanus, Corynascus thermophilus, Chrysosporium lucknowense, Fusarium graminearum, Fusarium venenatum, Neurospora crassa,* and *Talaromyces piniphilus.*

According to some embodiments, the ascomycetous filamentous fungus is a *Thermothelomyces heterothallica* strain comprising rDNA sequence having at least 95%, or at least 96%, or at least 97%, or at least 98%, or at least 99% or 100% identity to the nucleic acid sequence set forth in SEQ ID NO: 15.

According to some embodiments, the ascomycetous filamentous fungus is *Thermothelomyces heterothallica* C1. According to certain embodiments, the *Thermothelomyces heterothallica* C1 is of strain UV18-25, deposit No. VKM F-3631 D and derivatives thereof.

According to an additional aspect, the present invention provides a method for producing a fungus capable of producing nicotinamide riboside or a precursor thereof, the method comprising transforming at least one cell of the fungus with at least one exogenous polynucleotide selected from the group consisting of (i) an exogenous polynucleotide encoding BNA6; (ii) an exogenous polynucleotide encoding NMA1; (iii) an exogenous polynucleotide encoding QNS1; (iv) an exogenous polynucleotide encoding ISN1; and (v) an exogenous polynucleotide encoding SDT1. Each possibility represents a separate embodiment of the invention.

According to some embodiments, the NR precursor is nicotinamide adenine dinucleotide (NAD) or nicotinamide mononucleotide (NMN).

According to some embodiments, the method comprises transforming at least one cell of the fungus with at least two, at least three, at least four or five exogenous polynucleotides encoding for different proteins selected from the group consisting of BNA6, NMA1, QNS1, ISN1, and SDT1.

According to some embodiments, the method further comprises engineering the fungus to inhibit the expression and/or activity of NRK1, URH1, PNP1, or NRT1 in the at least one cell. According to certain embodiments, the method further comprises engineering the fungus to inhibit the expression and/or activity of at least two different proteins selected from the group consisting of NRK1, URH1, PNP1, and NRT1 in the at least one cell. According to certain embodiments, the method further comprises engineering the fungus to inhibit the expression and/or activity of at least three different proteins selected from the group consisting of NRK1, URH1, PNP1, and NRT1 in the at least one cell. According to specific exemplary embodiments, the method further comprises engineering the fungus to inhibit the expression and/or activity of NRK1, URH1, PNP1, and NRT1 in the at least one cell.

According to some embodiments, inhibiting the expression of a protein or enzyme comprising deleting or disrupting the endogenous gene encoding for the protein or enzyme.

According to some embodiments, the method further comprises modulating the expression and/or activity of at least one additional endogenous enzyme of the nicotinamide riboside pathway.

According to some embodiments, the genetically modified fungus produces the nicotinamide riboside in an elevated amount compared to the amount produced by a corresponding unmodified fungus not transformed with the at least one polynucleotide.

According to some embodiments, the ascomycetous filamentous fungus is of a genus within *Pezizomycotina.*

According to some embodiments, the ascomycetous filamentous fungus is of a genus selected from the group consisting of *Thermothelomyces, Myceliophthora, Trichoderma, Aspergillus, Penicillium, Rasamsonia, Chrysosporium, Corynascus, Fusarium, Neurospora,* and *Talaromyces.*

According to some embodiments, the ascomycetous filamentous fungus is of a species selected from the group consisting of *Thermothelomyces heterothallica* or (*Myceliophthora thermophila*), *Myceliophthora lutea, Aspergillus nidulans, Aspergillus funiculosus, Aspergillus niger, Aspergillus oryzae, Trichoderma reesei, Trichoderma harzianum, Trichoderma longibrachiatum, Trichoderma viride, Rasamsonia emersonii, Penicillium chrysogenum, Penicillium verrucosum, Sporotrichum thermophile, Corynascus fumimontanus, Corynascus thermophilus, Chrysosporium lucknowense Fusarium graminearum, Fusarium venenatum, Neurospora crassa* and *Talaromyces piniphilus.*

According to some embodiments, the ascomycetous filamentous fungus is a *Thermothelomyces heterothallica* strain comprising rDNA sequence having at least 95%, or at least 96%, or at least 97%, or at least 98%, or at least 99% or 100% identity to the nucleic acid sequence set forth in SEQ ID NO: 15.

According to some embodiments, the ascomycetous filamentous fungus is *Thermothelomyces heterothallica* C1. According to certain embodiments, the *Thermothelomyces heterothallica* C1 is of strain UV18-25, deposit No. VKM F-3631 D or a derivative thereof.

According to a further aspect, the present invention provides a method of producing at least one nicotinamide riboside or a precursor thereof, the method comprising culturing the genetically modified fungus as described herein in a suitable medium; and recovering the at least one nicotinamide riboside product.

According to some embodiments, the recovering step comprises recovering the NR from the growth medium, from the fungal mass or both.

According to some embodiments, the NR is recovered from the growth medium. According to certain embodiment, at least 50%, 60%, 70%, 80%, 90% or 95% of the NR is secreted NR.

According to some embodiments, the medium comprises a carbon source selected from the group consisting of glucose, sucrose, xylose, arabinose, galactose, fructose, lactose, cellobiose, glycerol and any combination thereof. Each possibility represents a separate embodiment of the invention.

According to certain embodiments, culturing of the genetically modified fungus in a suitable medium provides for synthesis of nicotinamide riboside in an increased amount compared to the amount produced in a corresponding unmodified fungus cultured under similar conditions.

According to certain embodiments, the corresponding unmodified fungus is of the same species of the genetically modified fungus. According to some embodiments, the corresponding fungus is isogenic to the genetically modified fungus.

It is to be understood explicitly that the scope of the present invention encompasses homologs, analogs, variants and derivatives, including shorter and longer polypeptides, proteins and polynucleotides, as well as polypeptide, protein and polynucleotide analogs with one or more amino acid or nucleic acid substitution, as well as amino acid or nucleic acid derivatives, non-natural amino or nucleic acids and synthetic amino or nucleic acids as are known in the art, with the stipulation that these variants and modifications must preserve the activity of protein or enzymes described herein. Specifically, any active fragments of the active polypeptide or protein as well as extensions, conjugates and mixtures are disclosed according to the principles of the present invention.

It is to be understood that any combination of each of the aspects and the embodiments disclosed herein is explicitly encompassed within the disclosure of the present invention.

Other objects, features and advantages of the present invention will become clear from the following description and drawings.

BRIEF DESCRIPTION OF THE FIGURES

FIG. 3A. Extracellular metabolite concentration in cell culture medium of different strains as indicated. FIG. 3B. Intracellular metabolites detected following cold methanol extraction of harvested cells. FIG. 3C. Extra- and intracellular metabolites detected following cold methanol extraction of samples containing cells and culture medium. Metabolite concentrations are presented for different engineered C1 strains as indicated and detailed in Table 2.

FIG. 4A. Extra- and intracellular compounds (mg/L) found in cold methanol extracted cultivation samples containing the fungi and culture medium. Presented are the strains derived from M1889 (detailed in Table 2). FIG. 4B. Extracellular NR concentration (mg/L) in culture medium of different samples (corresponding to FIG. 4A samples). FIG. 4C. Extracellular compounds (mg/L) found in cold methanol extracted cultivation samples containing the fungi and culture medium. Presented are the strains derived from M1892. FIG. 4D. Extracellular NR concentration (mg/L) in culture medium of different samples (corresponding to FIG. 4C samples).

FIG. 6A. mChD042 and mChD045; Δnrk1:SDT1 Δnrt1:BNA6 Δpnp1:NMA1. FIG. 6B. mChD044 and mChD047; Δnrk1:SDT1 Δnrt1:BNA6 Δurh1:ISN1, QNS1. FIG. 6C. mChD071 and mChD073; Δnrk1:SDT1 Δnrt1:BNA6 Δurh1:ISN1, QNS1, Δpnp1:NMA1.

FIG. 10A. Concentrations of extracellular NR (mg/L), protein (mg/L) and biomass (g/L) in bioreactor cultivation with strain mcChD042-3-1. FIG. 10B—Extracellular compounds (mg/L). FIG. 10C—Combination of extra- and intracellular compounds (mg/L).

DETAILED DESCRIPTION OF THE INVENTION

Figure 1:
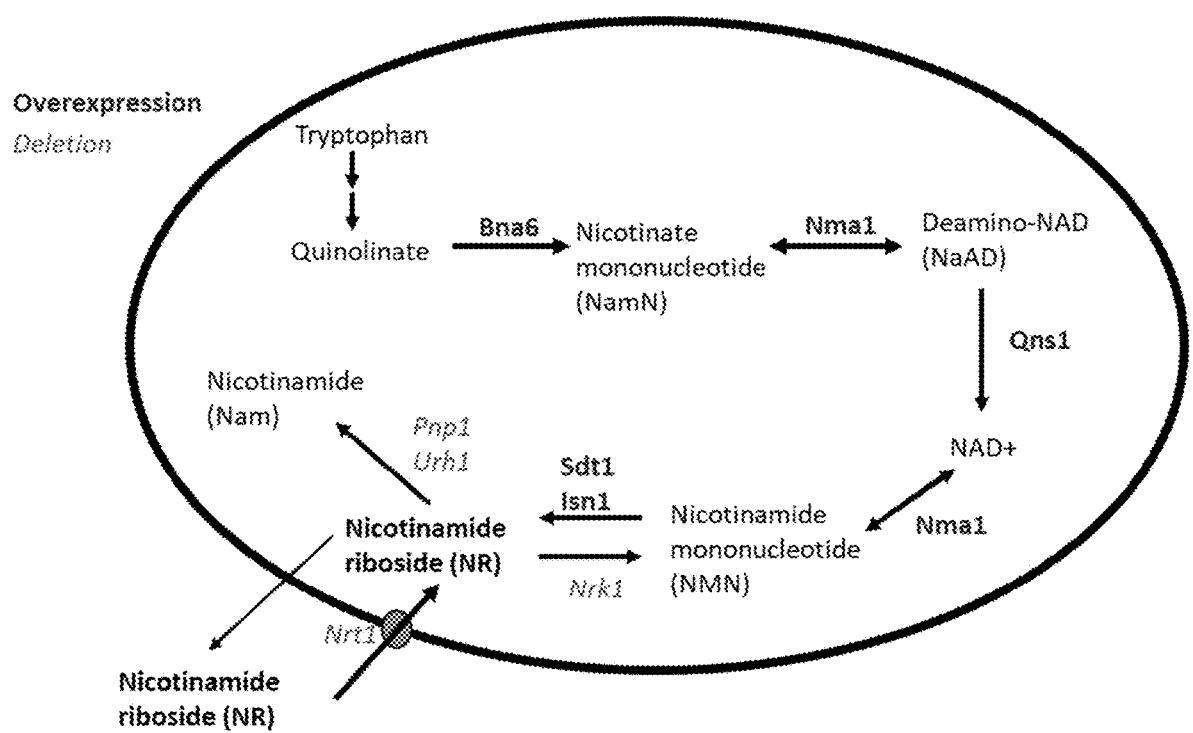
FIG. 1. Enzymatic reactions towards NR formation. The genes marked in bold gray are overexpressed and the ones in light gray and italics are deleted in the final strain.

The present invention provides alternative, highly efficient system for producing nicotinamide riboside and precursors thereof. The system of the invention is based in part on the filamentous fungus *Thermothelomyces heterothallica* C1 and particular strains thereof, which have been previously developed as a natural biological factory for protein as well as secondary metabolite production. These strains show high growth rate while keeping low culture viscosity, and are thus highly suitable for continuous growth in fermentation cultures at volumes as high as 100,000-150,000 liters or greater. The present invention in some embodiments provides genetically modified fungi engineered for production of NR by deleting four genes encoding enzymes that catabolize NR (NRK1, PNP1, URH1) or transport of excreted NR back into the cells (NRT1), and by overexpressing five genes encoding enzymes of the nicotinamide riboside pathway (BNA6, NMA1, QNA1, ISN1, SDT1).

Definitions

Ascomycetous filamentous fungi as defined herein refer to any fungal strain belonging to the group *Pezizomycotina*. The *Pezizomycotina* comprises, but is not limited to the following groups:
  *Sordariales*, including genera:
    *Thermothelomyces* (including species: *heterothallica* and *thermophila*),
    *Myceliophthora* (including the species *lutea* and unnamed species),
    *Corynascus* (including the species *fumimontanus*),
    *Neurospora* (including the species *crassa*);
  *Hypocreales*, including genera:
    *Fusarium* (including the species *graminearum* and *venenatum*),
    *Trichoderma* (including the species *reesei, harzianum, longibrachiatum* and *viride*);
  *Onygenales*, including genera:
    *Chrysosporium* (including the species *lucknowense*);
  *Eurotiales*, including genera:
    *Rasamsonia* (including the species *emersonii*),
    *Penicillium* (including the species *verrucosum*),
    *Aspergillus* (including the species *funiculosus, nidulans, niger* and *oryzae*)

*Talaromyces* (including the species *piniphilus* (formerly *Penicillium funiculosum*).

It is to be understood that the above list is not conclusive, and is meant to provide an incomplete list of industrially relevant filamentous ascomycetous fungal species.

While there may be filamentous ascomycetous species outside *Pezizomycotina*, that group does not contain *Saccharomycotina*, which contains most commonly known non-filamentous industrially relevant genera, such as *Saccharomyces, Komagataella* (including formerly *Pichia pastoris*), *Kluyveromyces* or *Taphrinomycotina*, which contains some other commonly known non-filamentous industrially relevant genera, such as *Schizosaccharomyces*.

All taxonomical categories above are defined according to the NCBI Taxonomy browser (ncbi.nlm.nih.gov/taxonomy) as of the date of the patent application.

It must be appreciated that fungal taxonomy is in constant move, and the naming and the hierarchical position of taxa may change in the future. However, a skilled person in the art will be able to unambiguously determine if a particular fungal strain belongs to the group as defined above.

According to certain embodiments, the filamentous fungus genus is selected from the group consisting of *Myceliophthora, Thermothelomyces, Aspergillus, Penicillium, Trichoderma, Rasamsonia, Chrysosporium, Corynascus, Fusarium, Neurospora, Talaromyces* and the like. According to some embodiments, the fungus is selected from the group consisting of *Myceliophthora thermophila, Thermothelomyces thermophila* (formerly *M. thermophila*), *Thermothelomyces heterothallica* (formerly *M. thermophila* and *heterothallica*), *Myceliophthora lutea, Aspergillus nidulans, Aspergillus funiculosus Aspergillus niger, Aspergillus oryzae, Penicillium chrysogenum, Penicillium verrucosum, Trichoderma reesei, Trichoderma harzianum, Trichoderma longibrachiatum, Trichoderma viride, Chrysosporium lucknowense, Rasamsonia emersonii, Sporotrichum thermophile, Corynascus fumimontanus, Corynascus thermophilus, Fusarium graminearum, Fusarium venenatum, Neurospora crassa,* and *Talaromyces piniphilus*.

In particular, the present invention provides *Thermothelomyces heterothallica* strain C1 as model for an ascomycetous filamentous fungus, capable of producing nicotinamide riboside.

The terms "*Thermothelomyces*" and its species "*Thermothelomyces heterothallica* and *thermophila*" are used herein in the broadest scope as is known in the art. Description of the genus and its species can be found, for example, in Marin-Felix Y (2015. Mycologica 107(3): 619-632 doi.org/10.3852/14-228) and van den Brink J et al. (2012, Fungal Diversity 52(1):197-207). As used herein "C1" or "*Thermothelomyces heterothallica* C1" or *Th. heterothallica* C1, or C1 all refer to *Thermothelomyces heterothallica* strain C1.

It is noted that the above authors (Marin-Felix et al., 2015) proposed splitting of the genus *Myceliophthora* based on differences in optimal growth temperature, morphology of the conidiospore, and details of the sexual reproduction cycle. According to the proposed criteria C1 clearly belongs to the newly established genus *Thermothelomyces*, which contain former thermotolerant *Myceliophthora* species rather than to the genus *Myceliophthora*, which remains to include the non-thermotolerant species. As C1 can form ascospores with some other *Thermothelomyces* (formerly *Myceliophthora*) strains with opposite mating type, C1 is best classified as *Th. heterothallica* strain C1, rather than *Th. thermophila* C1.

It must also be appreciated that the fungal taxonomy was also in constant change in the past, so the current names listed above may be preceded by a variety of older names beyond *Myceliophthora thermophila* (van Oorschot, 1977. Persoonia 9(3):403), which are now considered synonyms. For example, *Thermothelomyces heterothallica* (Marin-Felix et al., 2015. Mycologica, 3:619-63), is synonymized with *Corynascus heterotchallicus, Thielavia heterothallica, Chrysosporium lucknowense* and *thermophile* as well as *Sporotrichium thermophile* (Alpinis 1963. Nova Hedwigia 5:74).

It is further to be explicitly understood that the present invention encompasses any strain containing a ribosomal DNA (rDNA) sequence that shows 99% homology or more to SEQ ID NO: 15, and all those strains are considered to be conspecific with *Thermothelomyces heterothallica*.

*Th. heterothallica* strain C1 (as *Chrysosporium lucknowense* strain C1) and mutants derived therefrom were deposited in accordance with the Budapest Treaty with the number VKM F-3500 D, deposit date Aug. 29, 1996.

Particularly, the term *Th. heterothallica* strain C1 encompasses genetically modified sub-strains derived from the wild type strain, which have been mutated, using random or directed approaches, for example, using UV mutagenesis, or by deleting one or more endogenous genes. For example, the C1 strain may refer to a wild type strain modified to delete one or more genes encoding an endogenous protease and/or one or more genes encoding an endogenous chitinase. For example, C1 strains which are encompassed by the present invention include strain UV18-25, deposit No. VKM F-3631 D; strain NG7C-19, deposit No. VKM F-3633 D; and strain UV13-6, deposit No. VKM F-3632 D. Further C1 strain that may be used according to the teachings of the present invention include HC strain UV18-100f deposit No. CBS141147; HC strain UV18-100f deposit No. CBS141143; LC strain W1L#100I deposit No. CBS141153; and LC strain W1L#100I deposit No. CBS141149 and derivatives thereof.

It is to be explicitly understood that the teachings of the present invention encompass mutants, derivatives, progeny, and clones of the *Th. heterothallica* C1 strains, as long as these derivatives, progeny, and clones, when genetically modified according to the teachings of the present invention are capable of producing at least one nicotinamide riboside product according to the teachings of the invention.

It is to be explicitly understood that the term "derivative" with reference to fungal line encompasses any fungal parent line with modifications positively affecting product yield, efficiency, or efficacy, or affecting any trait improving the fungal derivative as a tool to produce the nicotinamide riboside. As used herein, the term "progeny" refers to an unmodified descendant from the parent fungal line, such as cell from cell.

Computational models of metabolic networks have been shown to be an effective tool in studying and engineering microbial metabolism for production of valuable chemicals. Due to the fast and ongoing development of the computational tools, the accuracy of such models is increased. The inventors of the present invention have used proprietary data to establish genome-scale metabolic model for *Th. heterothallica* C1. Simulations of the model were performed to identify metabolic targets to be engineered to improve NR production. Based on the model simulations, primary targets to be up- or down-regulation in order to increase the efficacy of the metabolic fluxes towards formation of the precursors of NR were searched and identified. Many of the precursors are involved in several competing metabolic reactions and therefore, engineering of relevant metabolic branching points may enhance the flux towards NR.

According to an aspect of the present invention there is provided a genetically modified filamentous fungus for producing nicotinamide riboside or a precursor thereof, the genetically modified filamentous fungus comprises at least one cell comprising at least one exogenous polynucleotide selected from the group consisting of (i) an exogenous polynucleotide encoding BNA6; (ii) an exogenous polynucleotide encoding NMA1; (iii) an exogenous polynucleotide encoding QNS1; (iv) an exogenous polynucleotide encoding ISN1; and (v) an exogenous polynucleotide encoding SDT1.

According to some embodiments, the NR precursor is NAD. According to some embodiments, the NR precursor is NMN.

According to some embodiments, the ascomycetous filamentous fungus comprises at least one cell having reduced or abolished expression and/or activity of at least one protein or enzyme that catabolize NR, modify NR or transport NR into the cells' cytoplasm. According to certain embodiments, the ascomycetous filamentous fungus comprises at least one cell having reduced or abolished expression and/or activity at least two, at least three or at least four proteins or enzymes that catabolize NR, modify NR or transport NR into the cells' cytoplasm.

According to some embodiments, the ascomycetous filamentous fungus comprises at least two exogenous polynucleotides encoding for an enzyme selected from the group consisting of BNA6, NMA1, QNS1, ISN1, and SDT1, said fungus comprises at least one cell having reduced or abolished expression and/or activity of at least two proteins or enzymes that catabolize NR, modify NR or transport NR into the cells' cytoplasm. According to some embodiments, the ascomycetous filamentous fungus comprises at least three exogenous polynucleotides encoding for an enzyme selected from the group consisting of BNA6, NMA1, QNS1, ISN1, and SDT1, said fungus comprises at least one cell having reduced or abolished expression and/or activity of at least three proteins or enzymes that catabolize NR, modify NR or transport NR into the cells' cytoplasm.

According to some embodiments, the ascomycetous filamentous fungus comprises at least one exogenous polynucleotide, the polynucleotide encoding for SDT1, said fungus comprises at least one cell having reduced or abolished expression and/or activity of NRK1. According to additional embodiments, the ascomycetous filamentous fungus comprises at least one exogenous polynucleotide, the polynucleotide encoding for BNA6, said fungus comprises at least one cell having reduced or abolished expression and/or activity of NRT1. According to exemplary embodiments, the ascomycetous filamentous fungus comprises at least two exogenous polynucleotides, the polynucleotides encoding for STD1 and BNA6, said fungus comprises at least one cell having reduced or abolished expression and/or activity of NRK1 and NRT1.

According to some embodiments, the genetically modified filamentous fungus comprises at least one cell comprising at least one exogenous polynucleotide encoding for BNA6. According to some embodiments, the genetically modified filamentous fungus comprises at least one cell comprising at least one exogenous polynucleotide encoding for NMA1. According to some embodiments, the genetically modified filamentous fungus comprises at least one cell comprising at least one exogenous polynucleotide encoding for QNS1. According to some embodiments, the genetically modified filamentous fungus comprises at least one cell comprising at least one exogenous polynucleotide encoding for ISN1. According to some embodiments, the genetically modified filamentous fungus comprises at least one cell comprising at least one exogenous polynucleotide encoding for SDT1.

According to some embodiments, the genetically modified filamentous fungus does not express NRK1. According to some embodiments, the genetically modified filamentous fungus does not express URH1. According to some embodiments, the genetically modified filamentous fungus does not express PNP1. According to some embodiments, the genetically modified filamentous fungus does not express NRT1.

According to specific embodiments, the ascomycetous filamentous fungus comprises at least one cell comprising three exogenous polynucleotides encoding for SDT1, BNA6, and NMA1, said fungus comprises at least one cell having reduced or abolished expression and/or activity of NRK1, NRT1 and PNP1.

According to an aspect of the present invention there is provided a genetically modified ascomycetous filamentous fungus for producing nicotinamide riboside, wherein the genetically modified filamentous fungus comprises at least one cell comprising exogenous polynucleotides encoding for BNA6, NMA1, QNS1, ISN1, and SDT1; said genetically modified ascomycetous filamentous fungus do not express or express reduced amount of NRK1, URH1, PNP1, and NRT1.

The bna6 gene encodes for Nicotinate-nucleotide pyrophosphorylase (BNA6 protein), catalyzing the reaction: $CO_2$+ diphosphate+nicotinate β-D-ribonucleotide=5-phospho-α-D-ribose 1-diphosphate+2 $H^+$+quinolinate. The *Thermothelomyces heterothallica* BNA6 amino acid sequence is set forth in SEQ ID NO: 1 (AEO54644.1). The genomic nucleotide sequence set forth in SEQ ID NO: 2 (MY-CTH_2297423). According to certain embodiments, the mRNA coding sequence is set forth in SEQ ID NO: 16.

According to some embodiments, the BNA6 comprises an amino acid sequence having at least 75%, 80%, 85%, 86%, 87%, 88%, 89%, 90%, 91%, 92%, 93%, 94%, 95%, 96%, 97%, 98%, 99%, or 100% identity to SEQ ID NO: 1.

According to some embodiments, BNA6 is encoded by a nucleic acid sequence having at least 65%, 70%, 75%, 80%, 85%, 90%, 95%, 98%, or 100% identity to SEQ ID NO: 16.

The nma1 gene encodes for Nicotinamide Mononucleotide Adenylyltransferase (NMA1 protein), catalyzes the transfer of the adenylyl moiety of ATP to nicotinamide mononucleotide to form NAD, involved in pathways of NAD biosynthesis, including the de novo, NAD(+) salvage, and nicotinamide riboside salvage pathways. The human homolog of nma1 is nmnat. Yeast nma1 has a paralog, nma2, that arose from the whole genome duplication. The *Thermothelomyces heterothallica* NMA1 amino acid sequence is set forth in SEQ ID NO. 3 (AEO58772.1). The genomic nucleotide sequence is set forth in SEQ ID NO: 4 (MY-CTH_2306323). According to certain embodiments, the mRNA coding sequence is set forth in SEQ ID NO: 17.

According to some embodiments, the NMA1 protein comprises an amino acid sequence having at least 75%, 80%, 85%, 86%, 87%, 88%, 89%, 90%, 91%, 92%, 93%, 94%, 95%, 96%, 97%, 98%, 99%, or 100% identity to SEQ ID NO: 3.

According to some embodiments, NMA1 is encoded by a nucleic acid sequence having at least 65%, 70%, 75%, 80%, 85%, 90%, 95%, 98%, or 100% identity to SEQ ID NO: 17.

The qns1 gene encodes for glutamine (Q) dependent Nad+ Synthetase (QNS1 protein), which is essential for the formation of NAD(+) from nicotinic acid adenine dinucleotide. The *Thermothelomyces heterothallica* QNS1 amino acid sequence is set forth in SEQ ID NO: 5 (AEO56119.1). The genomic nucleotide sequence is set forth in SEQ ID NO: 6 (MYCTH_79619). According to certain embodiments, the mRNA coding sequence is set forth in SEQ ID NO: 18.

According to some embodiments, the QNS1 protein comprises an amino acid sequence having at least 75%, 80%, 85%, 86%, 87%, 88%, 89%, 90%, 91%, 92%, 93%, 94%, 95%, 96%, 97%, 98%, 99%, or 100% identity to SEQ ID NO: 5.

According to some embodiments, QNS1 is encoded by a nucleic acid sequence having at least 65%, 70%, 75%, 80%, 85%, 90%, 95%, 98%, or 100% identity to SEQ ID NO: 18.

The isn1 gene encodes for Inosine 5'-monophosphate (IMP)-specific 5'-nucleotidase (ISN1 protein), which catalyzes the breakdown of IMP to inosine. The ISN1 is responsible for production of nicotinamide riboside. The *Thermothelomyces heterothallica* ISN1 amino acid sequence is set forth in SEQ ID NO: 7 (AEO54982.1). The Genomic nucleotide sequence is set forth in SEQ ID NO: 8 (MYCTH_2137468). According to certain embodiments, the mRNA coding sequence is set forth in SEQ ID NO: 19.

According to some embodiments, the ISN1 comprises an amino acid sequence having at least 75%, 80%, 85%, 86%, 87%, 88%, 89%, 90%, 91%, 92%, 93%, 94%, 95%, 96%, 97%, 98%, 99%, or 100% identity to SEQ ID NO: 7.

According to some embodiments, ISN1 is encoded by a nucleic acid sequence having at least 65%, 70%, 75%, 80%, 85%, 90%, 95%, 98%, or 100% identity to SEQ ID NO: 19.

The sdt1 gene encodes for Pyrimidine nucleotidase (SDT1 protein) and responsible for production of nicotinamide riboside. The *Thermothelomyces heterothallica* SDT1 amino acid sequence is set forth in SEQ ID NO: 9 (AEO55395.1). The genomic nucleotide sequence is set forth in SEQ ID NO: 10 (MYCTH_2050929). According to certain embodiments, the mRNA coding sequence is set forth in SEQ ID NO: 20.

According to some embodiments, the SDT1 comprises an amino acid sequence having at least 75%, 80%, 85%, 86%, 87%, 88%, 89%, 90%, 91%, 92%, 93%, 94%, 95%, 96%, 97%, 98%, 99%, or 100% identity to SEQ ID NO: 9.

According to some embodiments, SDT1 is encoded by a nucleic acid sequence having at least 65%, 70%, 75%, 80%, 85%, 90%, 95%, 98%, or 100% identity to SEQ ID NO: 20.

The nrk1 gene encodes for Nicotinamide Riboside Kinase 1 (NRK1 protein). It catalyzes the phosphorylation of nicotinamide riboside (NR) to form nicotinamide mononucleotide (NMN). The *Thermothelomyces heterothallica* sdt1 nucleotide sequence (MYCTH_2311889) including 1 kb flanks is set forth in SEQ ID NO: 11.

The urh1 gene encodes for Uridine nucleosidase (URH1 protein). It cleaves N-glycosidic bonds in nucleosides and involved in the nicotinamide riboside salvage pathway. The *Thermothelomyces heterothallica* urh1 nucleotide sequence (MYCTH_2295930) including 1 kb flanks is set forth in SEQ ID NO: 12.

The pnp1 gene encodes for Purine nucleoside phosphorylase (PNP1 protein). It specifically metabolizes inosine and guanosine nucleosides and involved in the nicotinamide riboside salvage pathway. The *Thermothelomyces heterothallica* pnp1 nucleotide sequence (MYCTH_2306426) including 1 kb flanks is set forth in SEQ ID NO: 13.

The term "transporter protein" as used herein refers to an enzyme capable of catalyzing the transport of nicotinamide riboside for importing nicotinamide riboside from the periplasm to the cytoplasm. The enzyme in *S. cerevisiae* is known as NRT1. The nrt1 gene encodes for Nicotinamide Riboside Transporter (NRT1 protein). The *Thermothelomyces heterothallica* nrt1 nucleotide sequence (MYCTH_2310258) including 1 kb flanks is set forth in SEQ ID NO: 14.

The present invention encompasses amino acid sequences that are substantially homologous to amino acids sequences based on any one of the sequences identified in this application. The terms "sequence identity" and "sequence homology" are considered synonymous in this specification.

There are many established algorithms available to align two amino acid sequences. Typically, one sequence acts as a reference sequence, to which test sequences may be compared. The sequence comparison algorithm calculates the percentage sequence identity for the test sequence(s) relative to the reference sequence, based on the designated program parameters. Alignment of amino acid sequences for comparison may be conducted, for example, by computer implemented algorithms (e.g. GAP, BESTFIT, FASTA or TFASTA), or BLAST and BLAST 2.0 algorithms.

In a comparison, the identity may exist over a region of the sequences that is at least 10 amino acid residues in length (e.g. at least 15, 20, 30, 40, 50, 75, 100, 150, 200, 250, 300, 350, 400, 450, 500, 550, 600, 650 or 685 amino acid residues in length, e.g. up to the entire length of the reference sequence). Each possibility represents a separate embodiment of the invention.

The term "exogenous" as used herein refers to a polynucleotide which is not naturally expressed within the fungus (e.g., heterologous polynucleotide from a different species) or to an endogenous nucleic acid of which overexpression in the fungus is desired. The exogenous polynucleotide may be introduced into the fungus in a stable or transient manner, so as to produce a ribonucleic acid (RNA) molecule and/or a polypeptide molecule. The term "endogenous" as used herein refers to a polynucleotide or polypeptide which is naturally present and/or naturally expressed within a fungus, particularly *Th. Heterothallica*, e.g., the genetic modified fungus comprises an additional copy of the sequence.

The term "heterologous" as used herein includes a sequence that was inserted to the fungi and is not naturally found in the fungi.

The term "overexpression" as used herein refers to an elevated level of gene product (whether nucleic acid or protein), or any metabolite produced as a result of the catalytic activity of a certain overexpressed gene product or a combination of gene products as compared with the expression of the same in the parental strain.

The terms "DNA construct", "expression vector", "expression construct" and "expression cassette" are used to refer to an artificially assembled or isolated nucleic acid molecule which includes a nucleic acid sequence encoding a protein of interest and which is assembled such that the protein of interest is functionally expressed in a target host cell. An expression vector typically comprises appropriate regulatory sequences operably linked to the nucleic acid sequence encoding the protein of interest. An expression vector may further include a nucleic acid sequence encoding a selection marker.

The terms "polynucleotide", "nucleic acid sequence", and "nucleotide sequence" are used herein to refer to polymers of deoxyribonucleotides (DNA), ribonucleotides (RNA), and modified forms thereof in the form of a separate fragment or as a component of a larger construct. A nucleic acid sequence may be a coding sequence, i.e., a sequence that encodes for an end product in the cell, such as a protein. According to certain embodiments of the invention, the protein is an enzyme. According to certain exemplary embodiments, the encoded enzymes include, but are not limited to, BNA6, NMA1, QNS1, SDT1, and ISN1. A nucleic acid sequence may also be a regulatory sequence, such as, for example, a promoter, or a terminator.

The terms "protein" is used herein to refer to a polymer of amino acid residues. The term "protein" usually indicates an amino acid sequence consisting of more than 50 amino acid residues.

A sequence (such as, nucleic acid sequence and amino acid sequence) that is "homologous" to a reference sequence refers herein to percent identity between the sequences, where the percent identity is at least 70%, at least 75%, preferably at least 80%, at least 85%, at least 90%, at least 95%, at least 98% at least 99% or at least 99.5%. Each possibility represents a separate embodiment of the present invention. Homologous nucleic acid sequences include variations related to codon usage and degeneration of the genetic code.

Nucleic acid sequences encoding the polypeptides of the present invention may be optimized for expression. Examples of such sequence modifications include, but are not limited to, an altered G/C content to more closely approach that typically found in filamentous fungi.

The phrase "codon optimization" refers to the selection of appropriate DNA nucleotides for use within a structural gene or fragment thereof that approaches codon usage within the organism of interest, and/or to a process of modifying a nucleic acid sequence for enhanced expression in the host cells of interest by replacing at least one codon (e.g., one or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Therefore, an optimized gene or nucleic acid sequence refers to a gene in which the nucleotide sequence of a native or naturally occurring gene has been modified in order to utilize statistically-preferred or statistically-favored codons within the organism.

Sequence identity may be determined using a nucleotide/amino acid sequence comparison algorithm, as known in the art.

The term "coding sequence" is used herein to refer to a sequence of nucleotide starting with a start codon (ATG) containing any number of codons excluding stop codons, and a stop codon (TAA, TGA, TAA), which code for a functional polypeptide.

Any coding sequence, or amino acid sequence listed herein also encompasses truncated sequences, which are missing 1, 2, 3, 4, 5, 10, 15, 20, 25, 50, or more codons or amino acids from any part of the sequence. Truncated versions of coding sequences or amino sequences can be identified using nucleotide/amino acid sequence comparison algorithm, as known in the art.

Any coding sequence, or amino acid sequence listed herein also encompasses fused sequences, which contain besides the coding sequence provided herein, or a truncation of that sequence as defined above, other sequences. The fused sequences can be sequences as disclosed herein and other sequences. Fused coding sequences or amino sequences can be identified using nucleotide/amino acid sequence comparison algorithm, as known in the art.

DNA sequences are assembled to expression cassettes, selection cassettes and further to DNA constructs and/or expression vectors by conventional molecular biological approaches utilizing restriction endonucleases and ligases, Gibson assembly or yeast recombination. Also, the above can be synthesized by DNA synthesis service providers. As known in the art, several different techniques can achieve the same result.

DNA sequences are assembled to expression cassettes joining a 5' regulatory regions (promoters), a coding sequence and a 3' regulatory regions (terminators) as described hereinbelow and as are known in the art. Any combination of these three sequences can form a functional expression cassette.

The list of terminators includes, but are not limited to that of *Th. heterothallica* genes encoding for uncharacterized protein G2QF75 (XP_003664349); polyubiquitin homologue (G2QHM8, XP_003664133); uncharacterized protein (G2QIA5, XP_003664731); beta-glucosidase (G2QD93, XP_003662704); elongation factor 1-alpha (G2Q129, XP_003660173); chitinase (G2QDD4, XP_003663544) phosphoglycerate kinase (PGK) (Uniprot G2QLD8), glyceraldehyde 3-phosphate dehydrogenase (GPD) (G2QPQ8), phosphofructokinase (PFK) (G2Q605); or triose phosphate isomerase (TPI) (G2QBRO); actin (ACT) (G2Q7Q5); cbh1 (GenBank AX284115) or β-glucosidase 1 bgl1 (XM_003662656). Exogenous terminators include that of *Aspergillus nidulans* gpdA terminator.

5' regulatory regions (promoters) are practically defined as a stretch of up to 2000 base pairs preceding the start codon of the coding sequence of the gene they regulate, provided that the preceding region is non-coding.

3' regulatory regions (terminators) are practically defined as a stretch of up to 300 base pairs downstream from the end codon of the coding sequence of the gene, provided that the subsequent region is non-coding.

DNA sequences are also assembled to selection marker cassettes, which are expression cassettes where the coding sequence codes for a gene that provides a selective advantage when present in a transformed strain. Such advantage can be utilization of a new carbon or nitrogen source, a resistance to a toxic substance, etc. More specifically, the selection marker used in the expression cassette of the present invention is amdS, which confers to the transformed fungi the ability to use acetamide as sole nitrogen source, where an *Aspergillus nidulans* gpdA promoter drives an *Aspergillus nidulans* amdS gene, and the transcription of which is terminated by its natural *Aspergillus nidulans* amdS terminator. Hygromycin resistance gene is also used as a selection marker.

DNA constructs used for targeted transformation are composed of (a) a suitable vector that allows the maintenance of the DNA construct in a particular host, (b) zero, one or more expression cassettes in any direction, (c) a selection marker cassette in any direction and (d) sequences that are identical to select stretches of the target genomic DNA (also called as targeting arms). These components are placed so, that the two targeting arms encompass any expression cassettes and the selection marker cassette, so that when homologous recombination happens between the targeting arms and the two identical regions in the genomic DNA, the sequence between the targeting arms of the DNA constructs gets inserted into the chromosome, and replaces the sequence originally present on the chromosome. Using this principle, genes can be knocked out from, or inserted into the genome. By placing a sequence downstream of the selection marker cassette, which is identical to the sequence just upstream of the selection marker cassette, it is possible to recycle the marker as known in the art.

The term "regulatory sequences" refer to DNA sequences which control the expression (transcription) of coding sequences, such as promoters, enhancers and terminators.

The term "promoter" is directed to a regulatory DNA sequence which controls or directs the transcription of another DNA sequence in vivo or in vitro. Usually, the promoter is located in the 5' region (that is, precedes, located upstream) of the transcribed sequence. Promoters may be derived in their entirety from a native source, or be composed of different elements derived from different promoters found in nature, or even comprise synthetic nucleotide segments. Promoters can be constitutive (i.e. promoter activation is not regulated by an inducing agent and hence rate of transcription is constant), or inducible (i.e., promoter activation is regulated by an inducing agent or environmental condition). Promoters may also restrict transcription to a certain developmental stage or to a certain morphologically distinct part of the organism. In most cases the exact boundaries of regulatory sequences have not been completely defined, and in some cases, cannot be completely defined, and thus DNA sequences of some variation may have identical promoter activity.

The term "terminator" is directed to another regulatory DNA sequence which regulates transcription termination. A terminator sequence is operably linked to the 3' terminus of the nucleic acid sequence to be transcribed.

The terms "C1 promoter" and "C1 terminator" indicate promoter and terminator sequences suitable for use in C1, i.e., capable of directing gene expression in C1.

However, as known to the skilled artisan, the choice of promoters and terminators may not be critical, and similar results can be obtained with a variety of promoters and terminators providing similar or identical gene expression.

The term "operably linked" means that a selected nucleic acid sequence is in proximity with a regulatory element (promoter, enhancer and/or terminator) to allow the regulatory element to regulate expression of the selected nucleic acid sequence.

The present invention discloses the production of nicotinamide riboside using genetically modified strains of *Th. heterothallica* C1. As described hereinabove, filamentous fungi of other species sharing endogenous similar pathways of precursor production can be also used.

According to certain embodiments, the polynucleotides of the present invention are designed based on the amino acid sequence of the enzyme to be produced employing a codon usage of a filamentous fungus. According to certain embodiments, the filamentous fungus belongs to the group Pezizomycotina. According to some embodiments, the filamentous fungus belongs to a group selected from the group consisting of *Sordariales, Hypocreales Onygenales*, and *Eurotiales* including genera and species as described in the "definition" section hereinabove. According to certain exemplary embodiments, the fungus is *Th. heterothallica*. According to these embodiments, the polynucleotides of the present invention are polynucleotides identified in *Th. heterothallica* or homologs thereto. According to certain currently exemplary embodiments, the fungus is *Th. heterothallica* C1.

According to certain exemplary embodiments, the *Th. heterothallica* C1 strain is a derivative of strain UV18-25.

According to certain embodiments, the exogenous polynucleotide is endogenous to the fungus, particularly to *Th. heterothallica* C1. According to certain embodiments, the exogenous polynucleotide is heterologous to the fungus, particularly to *Th. heterothallica* C1.

The polynucleotides encoding each of the enzymes may form part of one or more DNA constructs and/or expression vectors. According to certain embodiments, each of the polynucleotide forms part of a separate DNA construct/vector. According to other embodiments, part or all the polynucleotides are present within the same DNA construct/expression vector. This means that genes may be introduced one by one, or several of them may also be introduced to the transformed fungi at one time.

The DNA constructs or expression vector or plurality of same each comprises regulatory elements controlling the transcription of the polynucleotides within the at least one fungus cell. The regulatory element can be a regulatory element endogenous to the fungus, particularly to *Th. heterothallica* C1 or exogenous to the fungus.

According to certain embodiments, the regulatory element is selected from the group consisting of a 5' regulatory element (collectively referred to as promoter), and 3' regulatory element (collectively referred to as terminator), even though these nucleotide sequences may contain additional regulatory elements not classified as promoter or terminator sequences in the strict sense.

According to certain embodiments, the DNA construct or expression vector comprises at least one promoter operably linked to at least one polynucleotide containing a coding sequence, operably linked to at least one terminator. According to certain embodiments, the promoter is endogenous promoter of the fungus, particularly to *Th. heterothallica*. According to additional or alternative embodiments, the promoter is heterologous to the fungus, particularly to *Th. heterothallica*. According to certain embodiments, the terminator is endogenous terminator of the fungus, particularly to *Th. heterothallica*. According to additional or alternative embodiments, the terminator is heterologous to the fungus, particularly to *Th. heterothallica*.

According to certain exemplary embodiments, the DNA constructs contain synthetic regulatory elements called as "synthetic expression system" (SES) essentially as described in International (PCT) Application Publication No. WO 2017/144777.

According to certain embodiments, the one or more polynucleotides is stably integrated into at least one chromosomal locus of the at least one cell of the genetically modified fungus. According to certain embodiments, the one or more polynucleotides is/are stably integrated into one or more defined sites on the fungal chromosomes. According to certain embodiments, the one or more polynucleotides is/are stably integrated into random sites of the chromosome. According to certain embodiments, the polynucleotides may be incorporated in targeted or random fashion as 1, 2, or more copies to 1, 2 or more chromosomal loci.

According to certain alternative embodiments, the one or more polynucleotides is transiently expressed using extrachromosomal expression vectors as is known to a person skilled in the art.

According to certain exemplary embodiments the *Th. heterothallica* ku70 homologous gene is knocked out by preferentially eliminating the full coding sequence of the ku70 gene as known in the art. The inactivation of the ku70 gene enhances the percentage of targeted transformations as known in the art.

According to certain embodiments, culturing of the genetically modified fungus in a suitable medium provides for synthesis of nicotinamide riboside product, and/or derivatives thereof in an increased amount compared to the amount produced in a corresponding unmodified fungus cultured under similar conditions.

According to certain embodiments, the corresponding unmodified fungus is of the same species of the genetically modified fungus. According to some embodiments, the corresponding fungus is isogenic to the genetically modified fungus.

According to certain exemplary embodiments, the present invention provides a genetically modified Th. heterothallica C1 fungus that enables producing nicotinamide riboside. According to these embodiments, such genetically modified Th. heterothallica C1 fungus comprises at least one cell comprising at least one polynucleotide selected from the group consisting of (i) an exogenous polynucleotide encoding Nicotinate-nucleotide pyrophosphorylase (BNA6); (ii) an exogenous polynucleotide encoding Nicotinamide Mononucleotide Adenylyltransferase (NMA1); (iii) an exogenous polynucleotide encoding glutamine (Q) dependent Nad$^+$ synthetase (QNS1); (iv) an exogenous polynucleotide encoding Inosine 5'-monophosphate (IMP)-specific 5'-nucleotidase (ISN1); and (v) an exogenous polynucleotide encoding pyrimidine nucleotidase (SDT1).

According to certain embodiments, a suitable medium for culturing the genetically modified fungi comprises a carbon source selected from the group consisting of glucose, sucrose, xylose, arabinose, galactose, fructose, lactose, cellobiose, and glycerol. According to some embodiments, the carbon source is provided from waste of ethanol production or other bioproduction from starch, sugar beet and sugar cane such as molasses comprising fermentable sugars, starch, lignocellulosic biomass comprising polymeric carbohydrates such as cellulose and hemicellulose.

According to certain currently exemplary embodiments, the fungus is Th. heterothallica C1. According to certain embodiments, the strain of Th. heterothallica C1 is selected from the group consisting of strain UV18-25, deposit No. VKM F-3631 D; strain NG7C-19, deposit No. VKM F-3633 D; and strain UV13-6, deposit no. VKM F-3632 D. Additional strains that may be used are HC strain UV18-100f deposit No. CBS141147; HC strain UV18-100f deposit No. CBS141143; LC strain W1L#100I deposit No. CBS141153; and LC strain W1L#100I deposit No. CBS141149 and derivatives thereof. Each possibility represents a separate embodiment of the present invention.

According to another aspect, the present invention provides a method for producing a fungus capable of producing nicotinamide riboside, the method comprising transforming at least one cell of the fungus with at least one polynucleotide selected from the group consisting of (i) an exogenous polynucleotide encoding Nicotinate-nucleotide pyrophosphorylase (BNA6); (ii) an exogenous polynucleotide encoding Nicotinamide Mononucleotide Adenylyltransferase (NMA1); (iii) an exogenous polynucleotide encoding glutamine (Q) dependent Nad$^+$ synthetase (QNS1); (iv) an exogenous polynucleotide encoding Inosine 5'-monophosphate (IMP)-specific 5'-nucleotidase (ISN1); and (v) an exogenous polynucleotide encoding pyrimidine nucleotidase (SDT1).

According to some embodiments, the method further comprises deleting, inhibiting, or reducing the expression of an enzyme or protein selected from the group consisting of Nicotinamide riboside kinase 1 (NRK1), Uridine hydrolase 1 (URH1), Purine nucleoside phosphorylase (PNP1), and Nicotinamide riboside transporter 1 (NRT1).

The terms "reduced expression" or "inhibited expression" of a protein or enzyme as described herein are used herein interchangeably and include, but are not limited to, deleting or disrupting the gene that encodes for the protein or enzyme.

The terms "reduced activity" or "inhibited activity" of a protein or enzyme as described herein are used herein interchangeably and include, but are not limited to, post-translational modifications resulting in reduced or abolished activity of the protein or enzyme.

According to certain embodiments, the genetically modified fungus produces nicotinamide riboside in an elevated amount compared to the amount produced by a corresponding fungus not transformed with the polynucleotides.

Any method as is known in the art for transforming filamentous fungi with at least one polynucleotide can be used according to the teachings of the present invention.

The fungus and the polynucleotides are as described hereinabove.

According to yet another aspect, the present invention provides a method of producing nicotinamide riboside, the method comprising culturing the genetically modified fungus, particularly Th. heterothallica C1 fungi of the present invention in a suitable medium; and recovering the produced products.

According to certain embodiments, the medium comprises a carbon source selected from the group consisting of glucose, sucrose, xylose, arabinose, galactose, fructose, lactose, cellobiose, and glycerol. According to certain embodiments the carbon source is waste obtained from ethanol production or other bioproduction from starch, sugar beet and sugar cane such as molasses comprising fermentable sugars, starch, lignocellulosic biomass comprising polymeric carbohydrates such as cellulose and hemicellulose.

According to some embodiment, the nicotinamide ribose is purified from the fungi growth medium.

According to other embodiments, the nicotinamide riboside is extracted from the fungal mass. Any method as is known in the art for extracting metabolites from vegetative tissues can be used.

According to some embodiments, the genetically modified ascomycetous filamentous fungus produces nicotinamide ribose in an increased amount compared to the amount produced in a corresponding unmodified ascomycetous filamentous fungus cultured under similar conditions. According to certain embodiments, the genetically modified ascomycetous filamentous fungus is capable of producing at least 2, 3, 4, 5, 6, 7, 8, 9, 10, 11, 12, 13, 14, or 15 times more NR compared to its parent strain. Each possibility represents a separate embodiment of the invention. According to certain embodiments, the genetically modified ascomycetous filamentous fungus is capable of producing at least 10 times more NR compared to its parent strain.

According to some embodiments, the genetically modified ascomycetous filamentous fungus is capable of increasing the amount of secreted nicotinamide ribose in the growth medium by at least 2, 3, 4, 5, 6, 7, 8, 9, or 10 compared to a non-genetically modified ascomycetous filamentous fungus. Each possibility represents a separate embodiment of the invention.

According to some embodiments, the genetically modified ascomycetous filamentous fungus is capable of producing at least 10 mg NR/L growth medium. According to some embodiments, the genetically modified ascomycetous filamentous fungus is capable of producing at least 15 mg NR/L growth medium. According to certain embodiments, at least 70%, 80%, or 90% of the produced NR is secreted NR.

According to a further aspect, the present invention provides nicotinamide and/or precursors thereof produced by the genetically modified fungus, particularly the genetically modified *Th. heterothallica* C1 of the present invention. The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Methods

Production Medium:

| Compound | Final conc | g per litre | g per 500 ml |
|---|---|---|---|
| $(NH_4)_2SO_4$ | 35 mM | 4.62 | 2.31 |
| NaCl | 7 mM | 0.41 | 0.20 |
| $KH_2PO_4$ | 55 mM | 7.48 | 3.74 |
| CAS amino acids | 0.1% | 1.00 | 0.50 |
| Uracil | 10 mM | 1.12 | 0.56 |
| DDIW | | to ~980 ml | to ~490 ml |

Set pH to 6.5.
Sterilise by autoclaving.
After sterilisation add:

| Compound | Final conc | per litre | per 500 ml |
|---|---|---|---|
| 50% Glucose | 0.5% | 10 ml | 5 ml |
| 1M $MgSO_4$ | 2 mM | 2 ml | 1 ml |
| 1000× MYT Trace elements | 1× | 1 ml | 500 µl |
| 1M Uridine (stock −20 C.) | 10 mM | 10 ml | 5 ml |

User of M3 - Production medium; just before use add to the a mount needed:

| | | |
|---|---|---|
| 200× Pen/Strep stock (−20 C.) | 1× | 5 ml per litre medium |
| Biotin stock, 200 ug/ml (−20 C.) | 4 µg/l | 20 µl per litre medium |

*1000× trace element solution contains 174 mM EDTA, 76 mM $ZnSO_4 \cdot 7H_2O$, 178 mM $HB_3O_3$, 25 mM $MnSO_4 \cdot H_2O$, 18 mM $FeSO_4 \cdot 7H_2O$, 7.1 mM $CoCl_2 \cdot 6H_2O$, 6.4 mM $CuSO_4 \cdot 5H_2O$, 6.2 mM $Na_2MoO_4 \cdot 2H_2O$.

Metabolite extraction protocols:

Excreted metabolites

Remove ~300 µl aliquot from the cultivation, remove cells by centrifugation and take the supernatant for analysis. Store at +4° C. up to one day, or at −80° C. for longer periods.

Intracellular Metabolites

Divide 50% methanol containing 13C-NAM as an internal standard in 5 ml aliquots and cool down to −80° C.

Filter a 3-5 ml aliquot of cell culture through a nylon membrane filter (Whatman, 0.45 µm pore size, 7404-004). Wash 3×5 ml DDIW.

Scrape the cells from the membrane, transfer into cold 50% methanol and incubate at −80° C. for 1 h.

Vortex and centrifuge at 7800 rpm in 15 ml Greiner tubes for 10 min to remove cell debris. Take 4 ml supernatant for analysis. Store at −80° C. up to 1 week.

Extra- and Intracellular Metabolites

Divide methanol—DDIW (2.5:1.5) solution containing 13C-NAM as an internal standard in 4 ml aliquots into 15 ml greiner tubes and cool down to −80° C.

Transfer 1 ml of cell culture into 4 ml cold methanol-DDIW (final concentration 50% methanol) and vortex. Incubate at −80° C. for 1 h.

Vortex and centrifuge at 7800 rpm in 15 ml Greiner tubes for 10 min to remove cell debris. Take 4 ml supernatant for analysis. Store at −80° C. up to 1 week.

Example 1

Identification of NR Biosynthetic Genes in *Thermothelomyces heterothallica* C1 Genome The genes to be deleted or over-expressed in the NR pathway in C1 were identified from C1 genome based on homology to the corresponding genes in *Saccharomyces cerevisiae*. *S. cerevisiae* pathway related to NR and other NAD metabolites is described e.g. in Evans et al. (2010, BMC Chem Biol 10:2). The closest homologues of the *S. cerevisiae* BNA6, QNS1, ISN1, URH1, NRK1, NMA1, NMA2, SDT1, PNP1 and NRT1 were identified in C1 using a bidirectional blast search. The *S. cerevisiae* protein and genome sequence data used in the search was obtained from SGD database, and in-house/Dyadic genome data was used for C1. A blast search of the amino acid sequences corresponding to the *S. cerevisiae* bna6, qns1, isn1, urh1 , and nrk1 genes showed a single homologue for each of the genes/proteins in the translated genome sequence of C1. This was confirmed by a blast search of the detected C1 counterpart sequences against the *S. cerevisiae* proteome sequence, which gave the original yeast query sequences as the best hits in the search. The blast search of the amino acid sequences corresponding to NMA1 and NMA2 gave the same protein in C1 as the best hit. The result is expected since nma2 is a duplication of the nma1 gene in *S. cerevisiae* genome. When *S. cerevisiae* sdt1/Sdt1p sequence was blasted against the translated C1 genome, homology to a single protein was detected. When the sequence of the homologue was used as query in a blast search against *S. cerevisiae* proteome, homology to two proteins, Sdt1p and Phm8p (genes sdt1 and pmh8) were detected. Homology of the C1 protein to Sdt1p was slightly higher than to Pmh8p. pmh8 gene is a paralog of sdt1 gene as a result of a gene duplication in *S. cerevisiae* genome. Similarly, when the amino acid sequence corresponding to *S. cerevisiae* Pnp1p was blasted against the translated C1 genome, a single homologue in C1 was found. When this C1 sequence was blasted back against *S. cerevisiae* proteome, Meu1p and Pnp1p (meu1 and pnp1 genes) were found as the best homologues. The homology to Meu1p was higher than that to Pnp1p. meu1 gene encodes an enzyme that degrades NR in the same manner as pnp1. When the closest homologue of *S. cerevisiae* nrt1 in C1, was blasted back against *S. cerevisiae* proteome, three proteins Dal4p, Fur4p and Fui1p (genes dal4, fur4, fui1) were detected to have a higher homology to the C1 protein as compared to the Nrt1p. When *S. cerevisiae* dal4, fur4 and fui1 were blasted against C1 genome same gene was detected. These results may indicate that there is only one gene in C1 representing all these four *S. cerevisiae* genes.

Example 2

Engineering of *Thermothelomyces heterothallica* C1 for Nicotinamide Ribose Production To engineer the C1 to produce elevated amounts of nicotinamide ribose selected enzymatic steps of the native NR biosynthetic pathway were enhanced and genes responsible for NR catabolism or uptake of excreted NR were knocked out. The engineering included several consecutive steps aiming at a strain, which has four deletions in genes encoding enzymes responsible for NR utilization (NRK1, PNP1, URH1) or transport of excreted NR (NRT1) back into the cells, and additional copies of five genes encoding enzymes for conversion of quinolinate intermediate to NR (SDT1, BNA6, NMA1, QNS1, ISN1) (see FIG. 1). A synthetic expression system (SES) to strengthen enzyme activities specific for NR biosynthesis was used.

Figure 2:
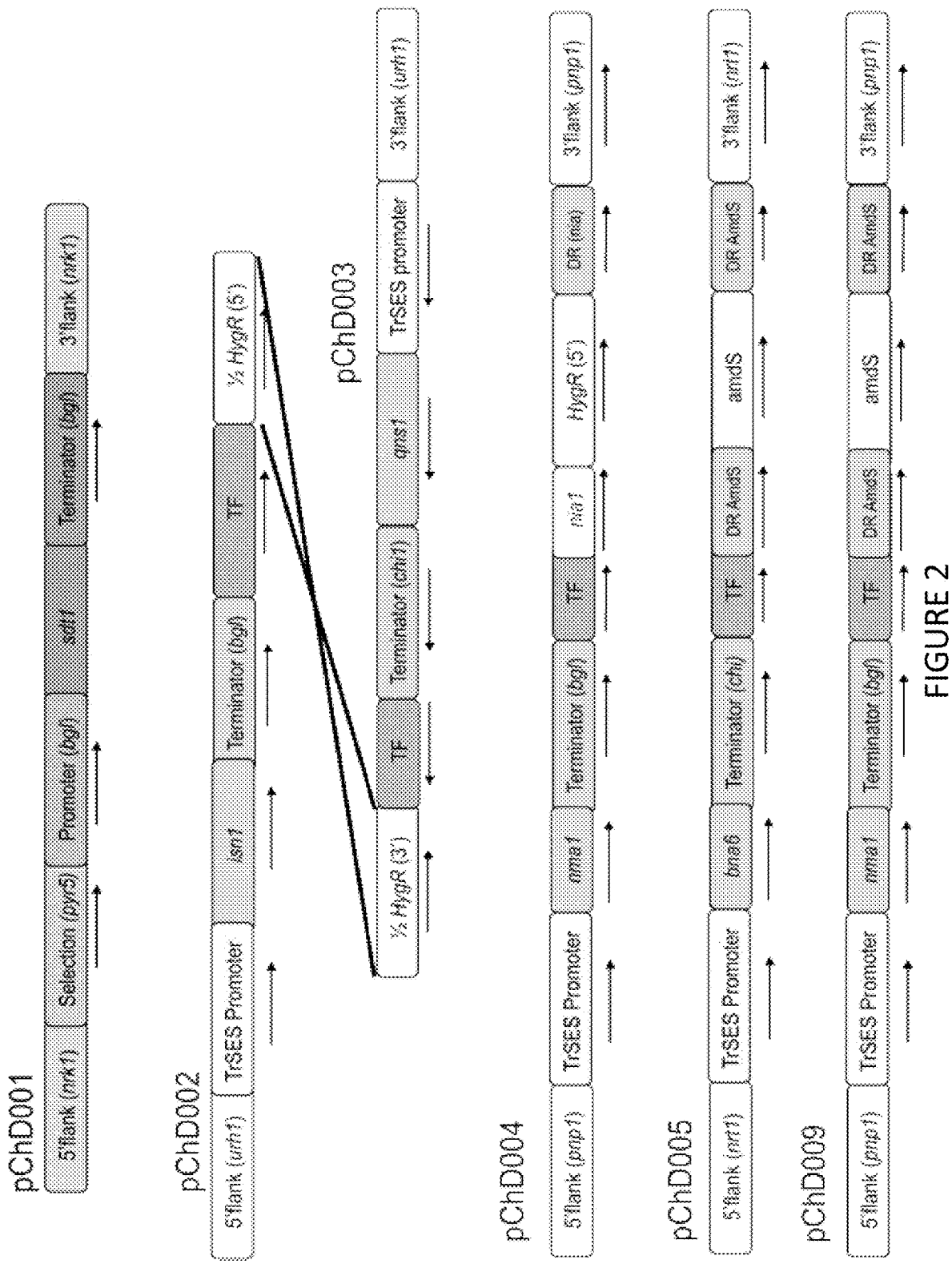
FIG. 2. A schematic representation of the plasmids constructed in this work. The marker gene nia1 in pChD004 and amdS in pChD005 and pChD00 are placed between repeated sequences (DR), which enable excision of the marker from the chromosome in the presence of counter selective agents, potassium nitrate or fluoroacetamide, respectively, and isolation of a strain free of the corresponding marker.

Two different C1 strains, a high cellulase strain M1889 and a low cellulase strain M1892, were used as the transformation hosts. Identical procedures were used to engineer the two hosts. Plasmids used for C1 engineering are described in Table 1 and FIG. 2. Hygromycin resistance, pyr5, amdS and nia1 markers were used in transformations. C1protoplasts were transformed using linearized plasmids and transformed colonies were selected on agar plates containing acetamide, sodium nitrate or hygromycin as the selective agent as appropriate. The presence of transformed DNA in the target loci was analyzed by PCR using three sets of primers specific for 5' end, 3' end, or the deleted region. Initially four transformation lines were carried out simultaneously with both host strains. Sequential transformations were carried out to construct the basic NR producing strain. The strains constructed are listed in Table 2.

TABLE 1

List of plasmids

| Plasmid name | Deletion target | Genes overexpressed | Selection marker |
| --- | --- | --- | --- |
| pMYT344 | nia1 | — | amdS |
| pChD001 | nrk1 | sdt1 | Pyr5 |
| pChD002 | urh1 | isn1 | ½ HygR* |
| pChD003 | urh1 | qns1 | ½ HygR* |
| pChD004 | pnp1 | nma1 | Nia1 HygR |
| pChD005 | nrt1 | bna6 | amdS |
| pChD009 | pnp1 | nma1 | amdS |

*pChD002 and pChD003 split marker

TABLE 2

Engineered C1 strains

| Strain name | Genes deleted | Genes overexpressed | Selection markers |
| --- | --- | --- | --- |
| M1889 (Δpyr5, Δku70B) derived strains: | | | |
| mChD001 | nrk1 | SDT1 | Pyr5 |
| mChD003 | nrt1 | BNA6 | amdS |
| mChD008 | nrk1, nrt1 | SDT1, BNA6 | amdS |
| mChD009 | nrk1, nia1 | SDT1 | Pyr5, amdS |
| mChD032 | nrk1, nia1 | SDT1 | Pyr5 |
| mChD037 | nrk1, nia1, nrt1 | SDT1, BNA6 | Pyr5, amdS |
| mChD042 | nrk1, nrt1, pnp1 | SDT1, BNA6, NMA1 | Pyr5, amdS Nia1, HygR |
| mChD044 | nrk1, nia1, nrt1, urh1 | SDT1, BNA6, ISN1, QNS1 | Pyr5, amdS, HygR |
| mChD071 | nrk1, nia1, nrt1, urh1, pnp1 | SDT1, BNA6, ISN1, QNS1, NMA1 | Pyr5, amdS, HygR, Nia1 |
| mChD074 | nrk1, nia1, nrt1 | SDT1, BNA6 | Pyr5 |
| mChD076 | nrk1, nial, nrt1, urh1 | SDT, BNA6, ISN1, QNS1 | Pyr5 HygR |
| mChD079, mChD080 | nrk1, nrt1, pnp1 | SDT1, BNA6, NMA1 | Pyr5, Nia1, HygR |
| mChD083 | nrk1, nia1, nrt1, urh1, pnp1 | SDT1, BNA6, ISN1, QNS1, NMA1 | Pyr5, HygR, Nia1 |
| mChD084 | nrk1, nia1, nrt1, urh1, pnp1 | SDT1, BNA6, ISN1, QNS1, NMA1 | Pyr5, amdS, HygR |
| M1892 (Δpyr5, Δku70B) derived strains: | | | |
| mChD004 | nrk1 | SDT1 | Pyr5 |
| mChD006 | nrt1 | BNA6 | amdS |
| mChD011 | nrk1, nrt1 | SDT1, BNA6 | amdS |
| mChD012 | nrk1, nia1 | SDT1 | Pyr5, amdS |
| mChD033 | nrk1, nia1 | SDT1 | Pyr5 |
| mChD041 | nrk1, nia1, nrt1 | SDT1, BNA6 | Pyr5, amdS |
| mChD045 | nrk1, nrt1, pnp1 | SDT1, BNA6, NMA1 | Pyr5, amdS Nia1, HygR |
| mChD047 | nrk1, nia1, nrt1, urh1 | SDT1, BNA6, ISN1, QNS1 | Pyr5, amdS, HygR |
| mChD073 | nrk1, nia1, nrt1, urh1, pnp1 | SDT1, BNA6, ISN1,QNS1, NMA1 | Pyr5, amdS, HygR, Nia1 |
| mChD075 | nrk1, nia1, nrt1 | SDT1, BNA6 | Pyr5 |
| mChD077 | nrk1, nia1, nrt1, urh1 | SDT1, BNA6, ISN1,QNS1 | Pyr5 HygR |
| mChD082 | nrk1, nrt1, pnp1 | SDT1, BNA6, NMA1 | Pyr5, Nia1, HygR |

The effects of the genetic modifications on the production of NR were assessed by quantification of NR and selected metabolic pathway intermediates by analyzing samples of cells and cell culture medium.

Example 3

Analysis of NAD$^+$ Metabolome

A quantitative UPLC-MS/MS method for analysis of NR and 10 other intermediates from extra- and intracellular C1 samples was set up. The method is based on an article by Evans et al. (BMC Chemical Biology 2010 10:2).

All extracellular samples were reconstituted in 50% mobile phase B (20 mM ammonium acetate in 80% acetonitrile, pH 9.9) before analysis. Intracellular samples were analyzed directly after extraction. The appropriate dilutions of the samples were done when necessary.

Analysis was performed on an Acquity UHPLC system, Waters (Milford, MA, USA) and Waters Xevo TQ-S MS (Manchester, UK) using an ACQUITY UPLC BEH Amide Column, 130 Å, 1.7 μm, 2.1 mm×100 mm (Waters), kept at 30° C. Injection volume was 2 μl. Separation was performed using gradient elution with 50 mM ammonium acetate in water, pH 9.9 (A) and 20 mM ammonium acetate in 80% acetonitrile, pH 9.9 (B) at a flow rate of 0.5 ml/min. Gradient program was following: 0 min 80% B, 3.0 min 65% B, 3.1 min 80% B and equilibrium time between runs was 2.0 min.

Mass spectrometry was performed in positive polarity using the capillary voltage of 1.3 kV. Desolvation temperature was 500° C., and source temperature was 150° C. The cone gas flow was 150 1/h (nitrogen), desolvation gas was 1000 1/h (nitrogen), and collision gas was 0.15 ml/min.

Analytes were detected using multiple reaction monitoring (MRM) using auto dwell time function. Analytes were quantified by internal standard method. Nicotinamide-13C6 (Sigma-Aldrich) was used as internal standard. For other details of the method, see Table 3. The targeted UPLC-MS/MS method for NAD+ metabolites analysis, including the sample preparation protocols, was successfully set up and used for analysis.

TABLE 3

Precursor and product ions used for MRM, retention times, cone voltage and collision energy used for the analyzed compounds and the internal standards.

| Analyte | Abr | Precursor ion, m/z | Product ion, m/z | RT, min | Cone, V | CE, eV |
|---|---|---|---|---|---|---|
| Nicotinamide | NAM | 123 | 80 | 0.56 | 35 | 20 |
| Nicotinamide-13C6 (Internal Std) | NAM-C13 | 129 | 86 | 0.56 | 35 | 20 |
| Nicotinic acid | NA | 124 | 80 | 0.54 | 35 | 20 |
| Nicotinamide Riboside | NR | 255 | 123 | 1.32 | 12 | 14 |
| Nicotinic acid riboside | NAR | 256 | 124 | 0.81 | 14 | 13 |
| Nicotinamide mononucleotide | NMN | 335 | 123 | 1.18 | 12 | 16 |
| Nicotinate mononucleotide | NAMN | 336 | 124 | 1.04 | 12 | 18 |
| Nicotinic acid adenine dinucleotide | NAAD | 665 | 428 | 0.8 | 26 | 26 |
| NAD+, free acid | NAD | 664 | 428 | 0.94 | 26 | 26 |
| NADH, disodium salt | NADH | 666 | 649 | 0.67 | 20 | 26 |
| NADP, disodium salt | NADP | 744 | 604 | 1.19 | 18 | 26 |
| NADHP, tertasodium salt | NADHP | 746 | 729 | 0.97 | 20 | 30 |

Linearity, recovery, limit of detection (LOD) and limit of quantitation (LOQ) were determined. The calibration curves showed good linearity in the studied range from 0.002 µg/ml to 10 µg/ml with correlation coefficient $R^2$ greater than 0.99. The recoveries were good (>92%) for all studied compounds with the exception of NADH which recovery was 73.5%. Limit of detection (LOD) of the method was determined as lowest concentration of the spiked components that could be reliable differentiated from the background level (S/N>3), the limits of quantitation (LOQ) were determined as ratio S/N>10. All results are summarized in Table 4.

The stability of the metabolites was studied at 4° C. in cell culture medium. The spiked samples were analyzed on day 1, day 3 and day 7 (data not shown). Most of the compounds were stable for three days. The most notable exception was NADH, which did not give reliable results due to the poor stability.

Example 4

NR Production by the Engineered Strains

Production of NR and Related Metabolites in 24-Well Plate Cultivations

Figure 3A:
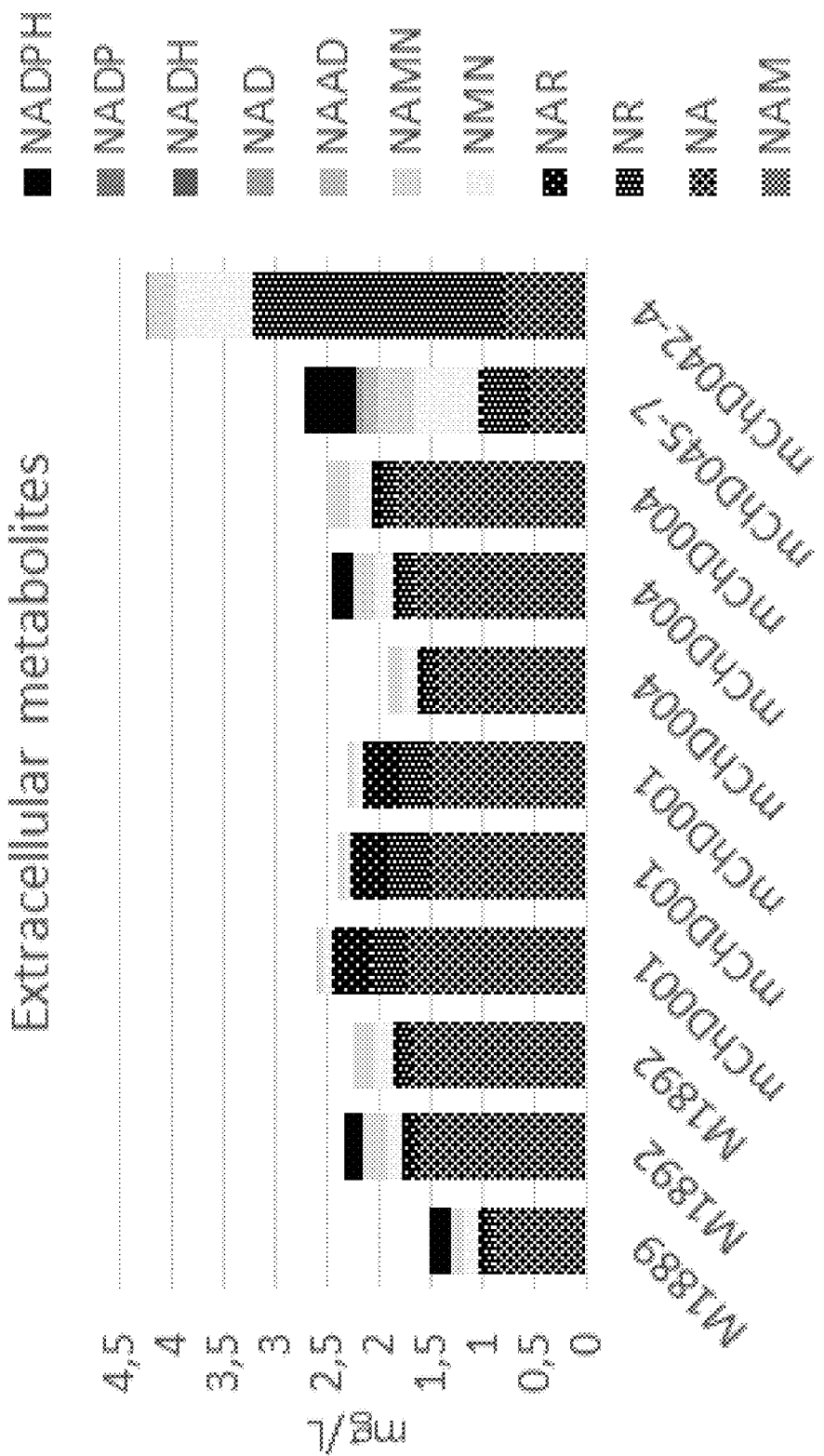
FIGS. 3A-3C.
Figure 3B:
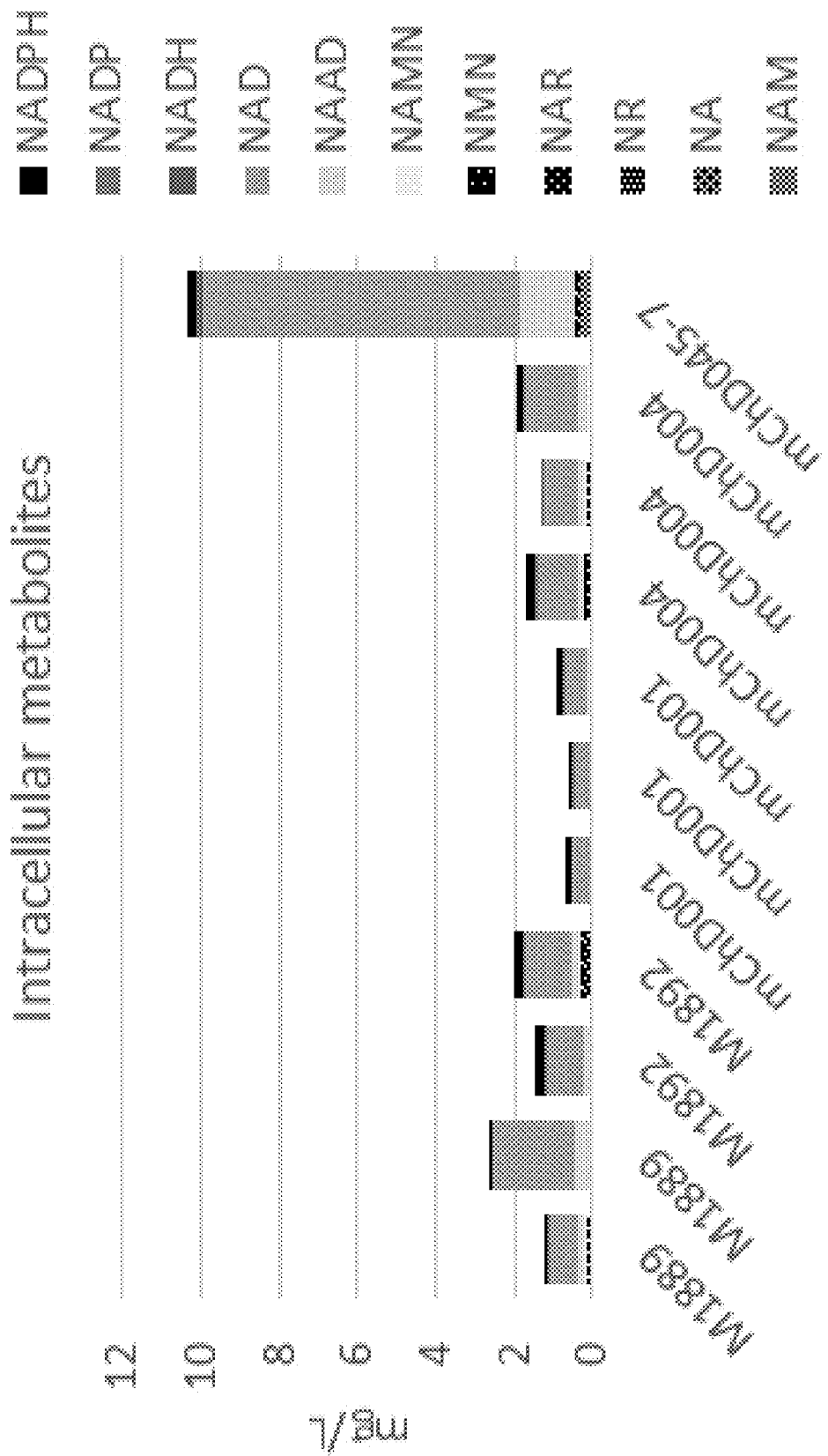
Figure 3C:
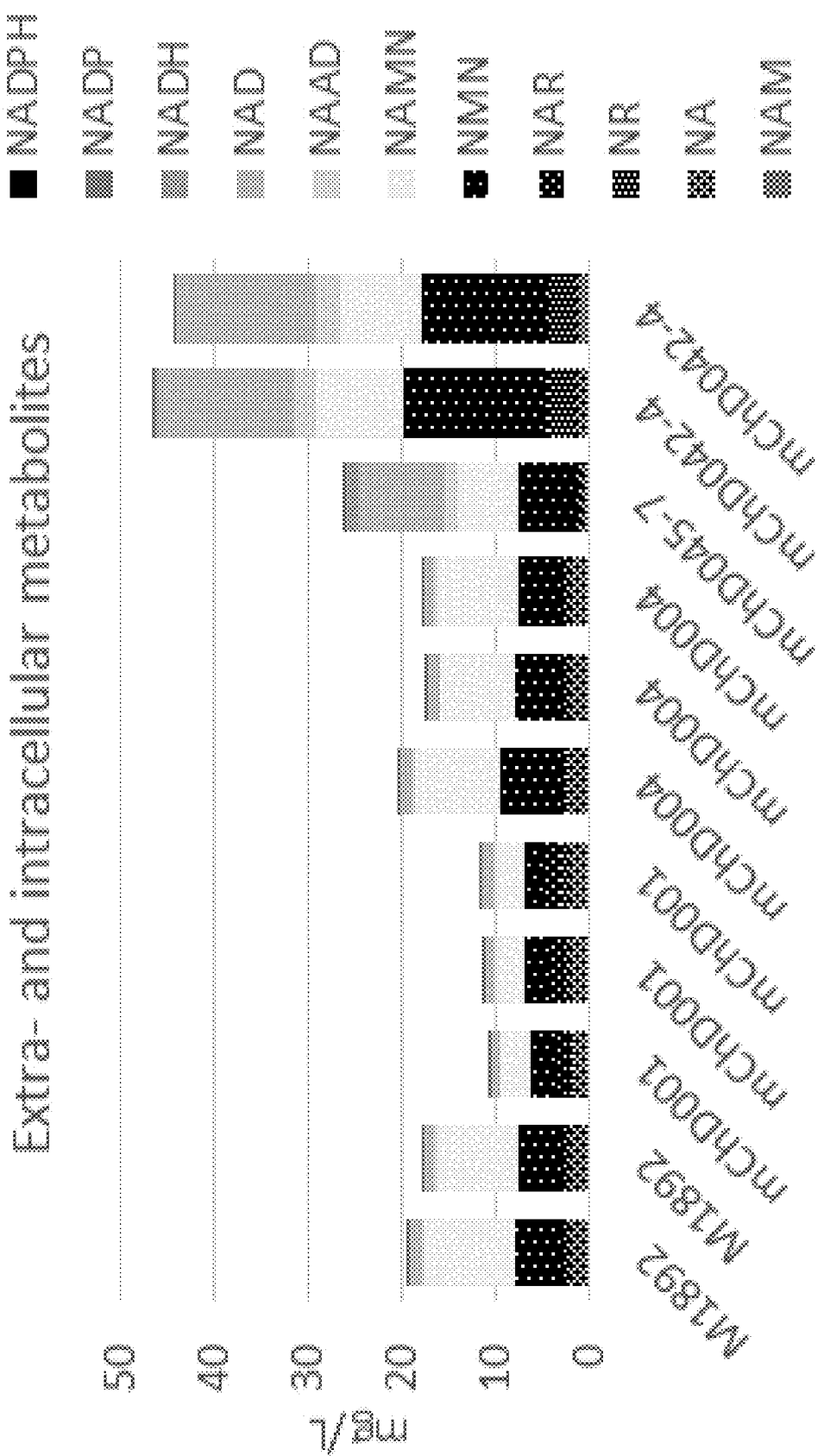
Figure 4A:
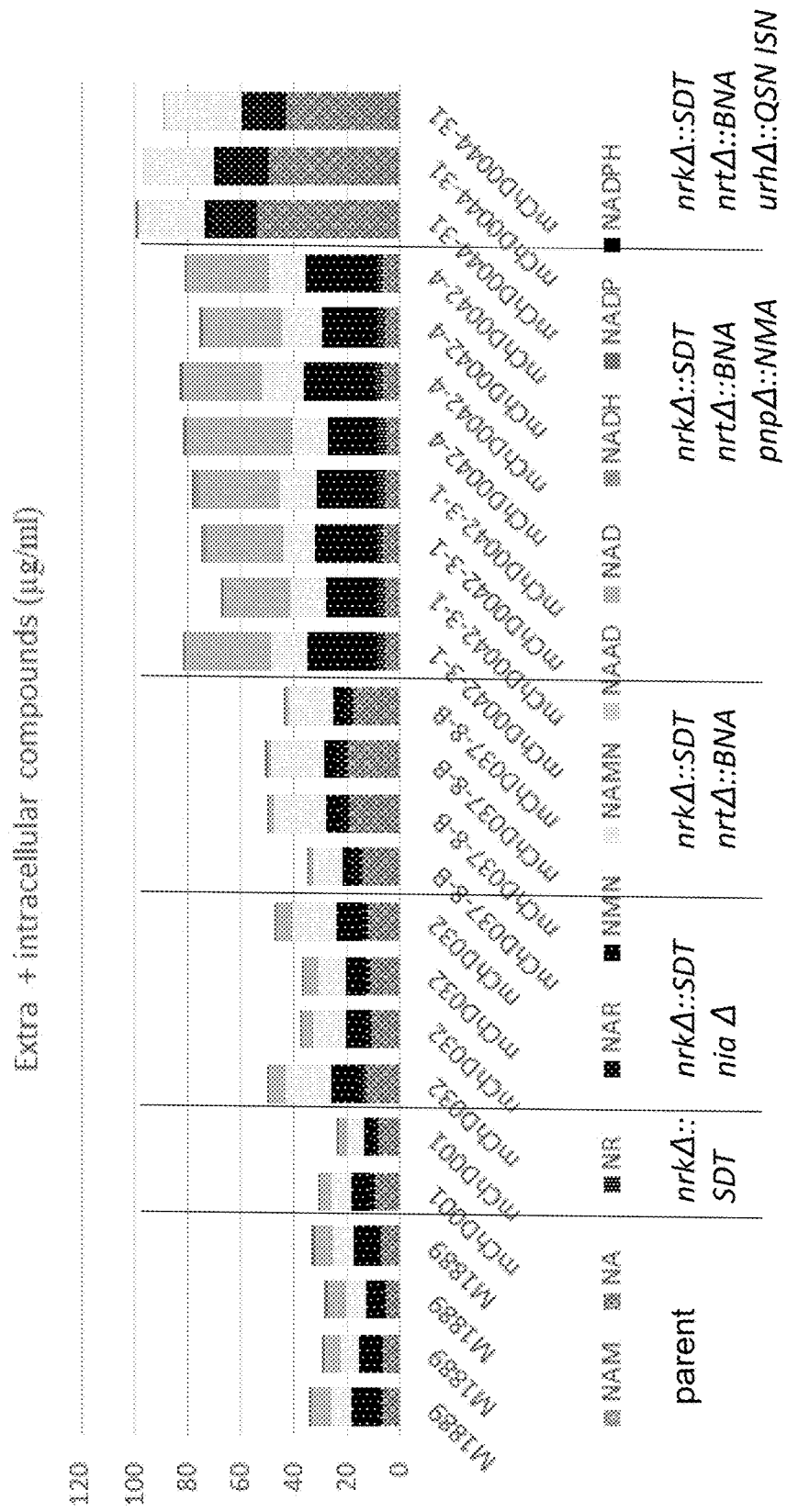
FIGS. 4A-4D.
Figure 4B:
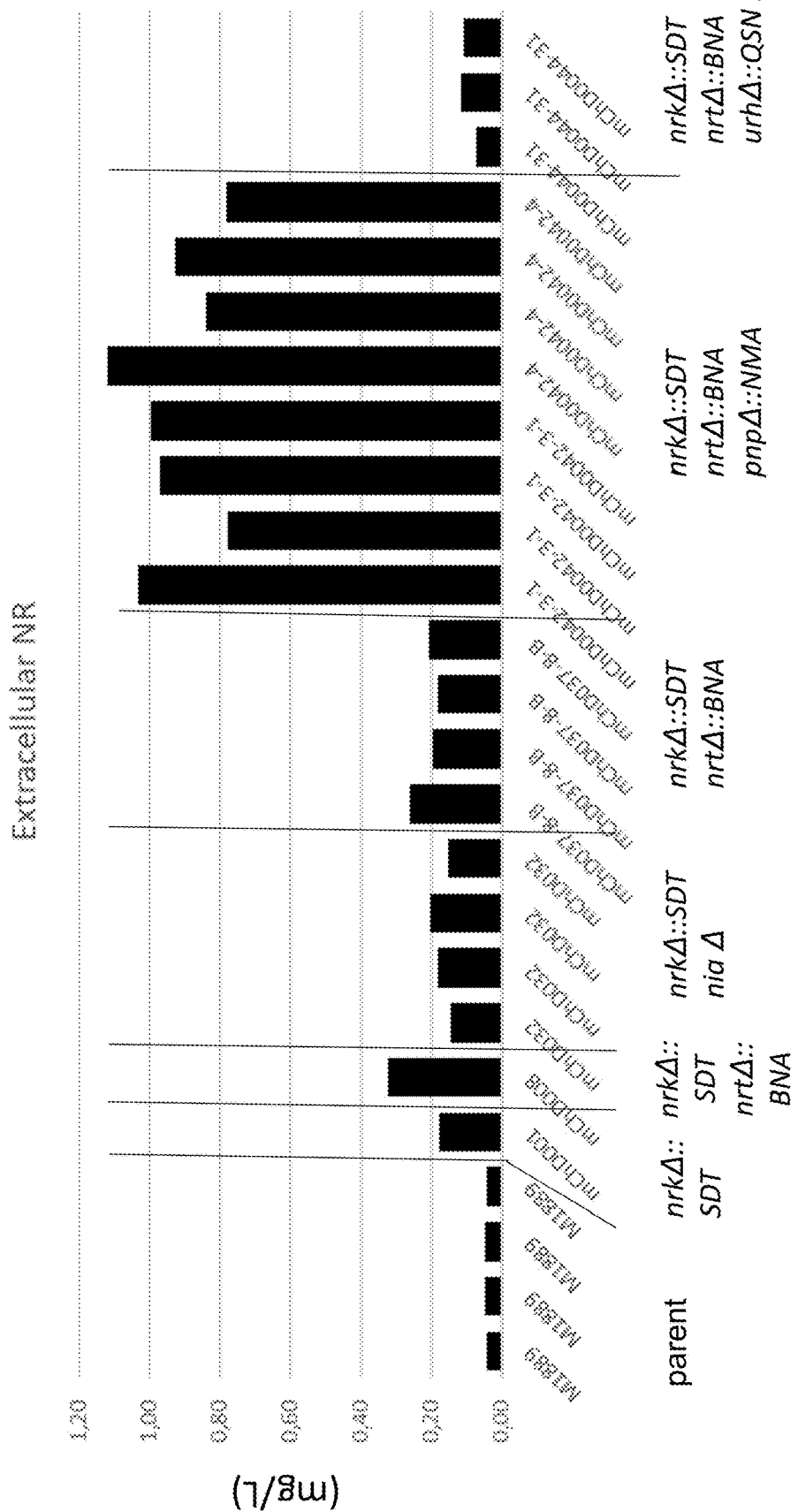
Figure 4C:
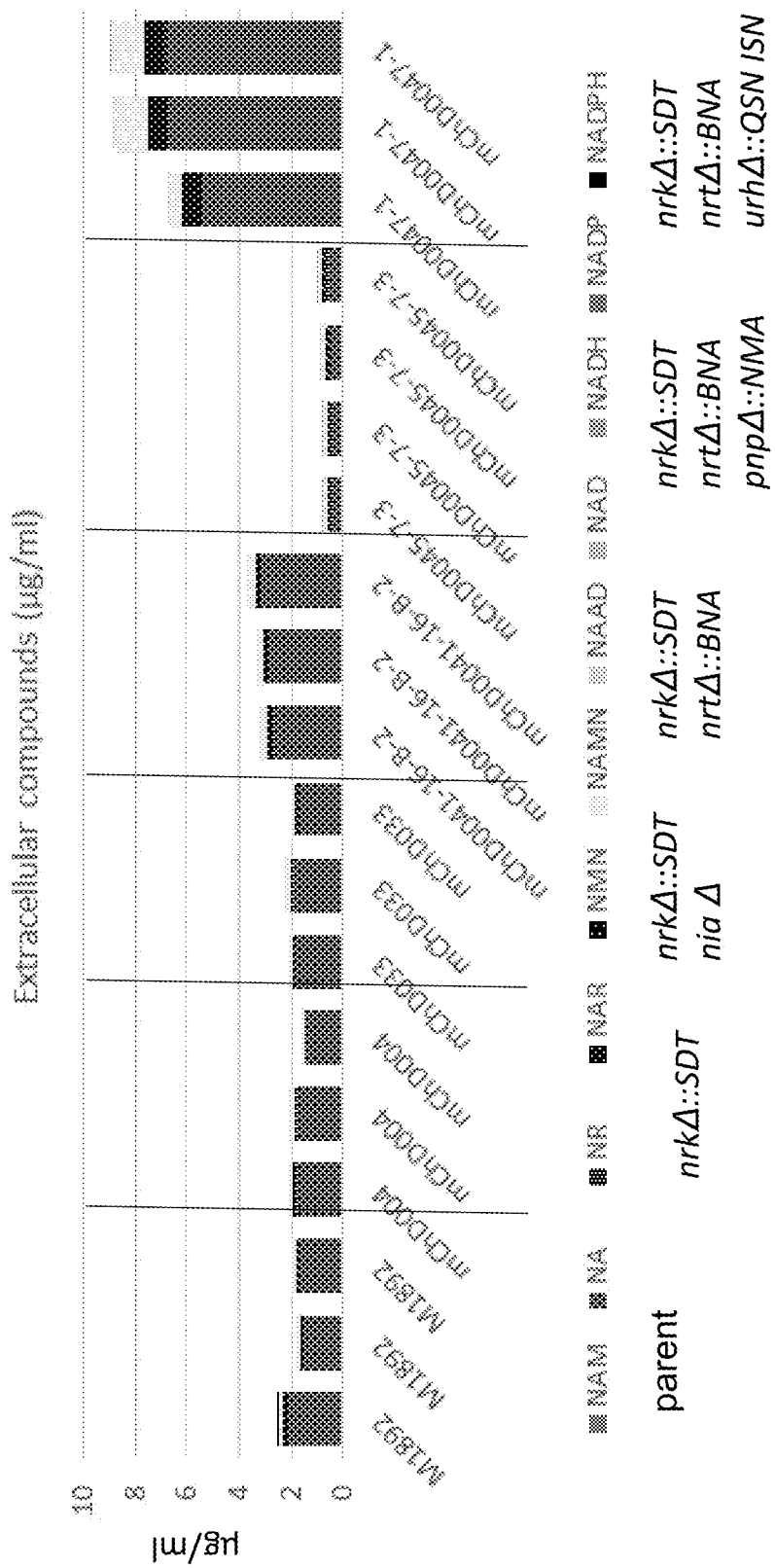
Figure 4D:
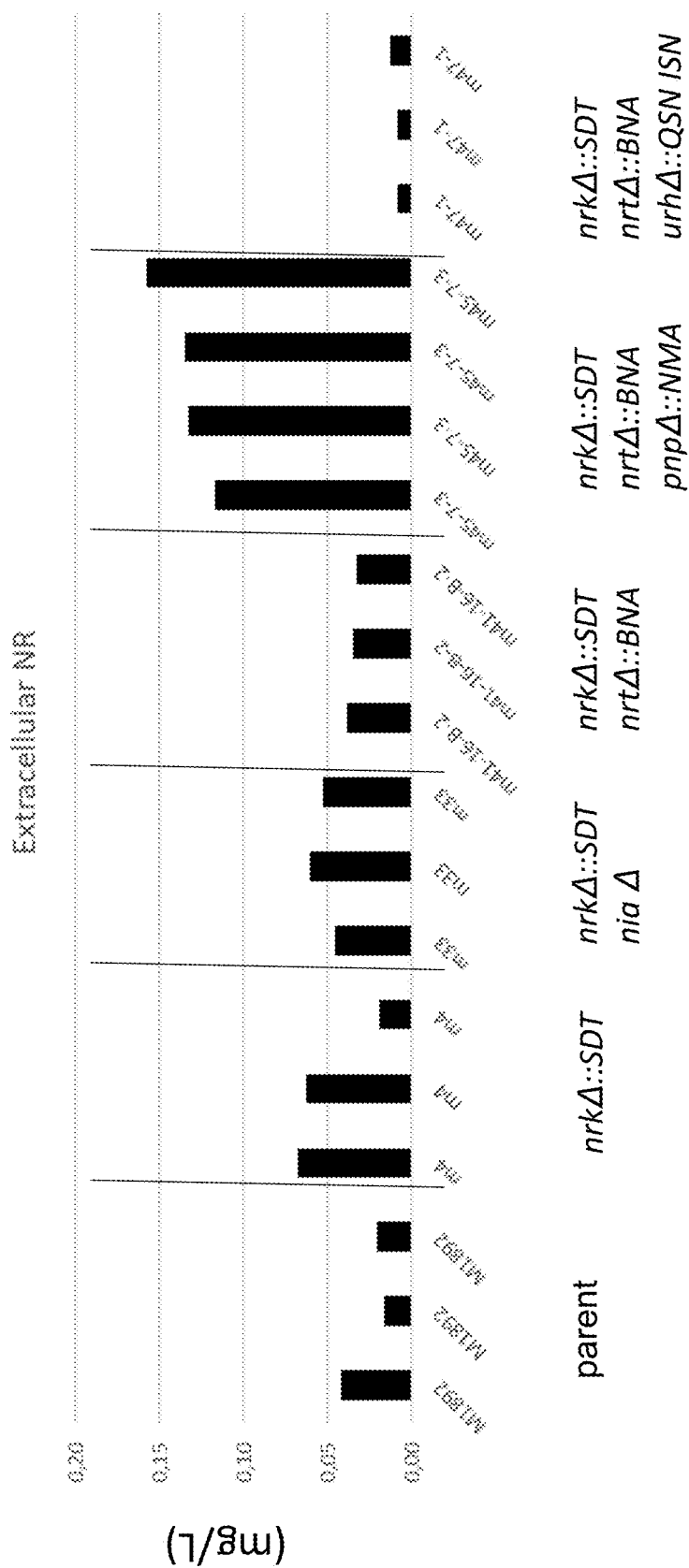

For determination of NR production, the different strains were grown in 3.5 ml liquid production medium in 24-well plates at 35° C. for three days with 800 rpm in a humidity-controlled shaker. NR and related metabolites were quantified from samples containing cell culture medium, cells harvested by filtration, or cells and culture medium together. Metabolites were released from cells using hot ethanol or cold methanol. The latter method appeared more suitable since some of the metabolites are unstable at high temperatures (data not shown). There were clear differences between excreted and intracellular metabolites (FIGS. 3A-3C).

Small amounts of NR were detected in the non-modified parental strains M1889 and M1892. NR, NA and NAR were predominately excreted into the culture medium (FIG. 3A). Engineered strains (mChDx) produced increased amounts of NR. NAD is the predominant intracellular compound (FIG. 3B). Samples containing a combination of culture medium and cells show all the metabolites (FIG. 3C). NR measurement from culture medium appears convenient and sufficient for comparing different strains for their ability to produce the desired compound. However, the consequences of the genetic modifications are not fully revealed by analyzing extracellular metabolites only, since many of the NR pre-

TABLE 4

Linearity, recovery, limit of detection and limit of quantitation of the method.

| Analyte | Abr | Linearity range, µg/ml | $R^2$ | Recovery % | LOD, µg/ml | LOQ, µg/ml |
|---|---|---|---|---|---|---|
| Nicotinamide | NAM | 0.005-10.00 | 0.9994 | 103.7 | 0.002 | 0.01 |
| Nicotinic acid | NA | 0.005-10.00 | 0.9998 | 101.4 | 0.02 | 0.1 |
| Nicotinamide Riboside | NR | 0.005-0.5 | 0.9973 | 100.4 | 0.001 | 0.005 |
| Nicotinic acid riboside | NAR | 0.005-0.2 | 0.9983 | 100.8 | 0.0005 | 0.001 |
| Nicotinamide mononucleotide | NMN | 0.01-5.00 | 0.9994 | 102.7 | 0.0005 | 0.002 |
| Nicotinate mononucleotide | NAMN | 0.01-2.00 | 0.9983 | 107.0 | 0.0005 | 0.001 |
| Nicotinic acid adenine dinucleotide | NAAD | 0.005-10.00 | 0.9997 | 100.4 | 0.01 | 0.05 |
| NAD+, free acid | NAD | 0.002-10.00 | 0.9997 | 104.4 | 0.002 | 0.01 |
| NADH, disodium salt | NADH | 0.1-10.00 | 0.9998 | 73.5 | 0.01 | 0.05 |
| NADP, disodium salt | NADP | 0.01-10.0 | 0.9970 | 92.9 | 0.0005 | 0.002 |
| NADPH, tertasodium salt | NADPH | 0.01-2.0 | 0.9975 | 99.9 | 0.01 | 0.05 | cursors are not excreted into the culture medium. Therefore, quantification of both extra- and intracellular compounds provides additional understanding of the NR pathway activities of the modified strains.

FIG. 4. illustrates the NR-related metabolites in a comprehensive set of modified strains. A major improvement of NR production was observed in mChD042-strains and mChD045-strains in which the pnp1 gene was deleted along with NMA1 overexpression (FIGS. 4B and 4D). The M1889-derived strains produced more NR than the M1892 derived strains. The mChD042-strains excreted clearly more NR, NAD, NMN than their predecessors. In contrast, the mChD044- and mChD047-strains in which the urh1 gene was deleted along with the QNS1 and ISN1 overexpression, increased amounts of NA and NAR were produced (FIGS. 4A and 4C), while NR production was not increased (FIGS. 4B and 4D).

Figure 5A:
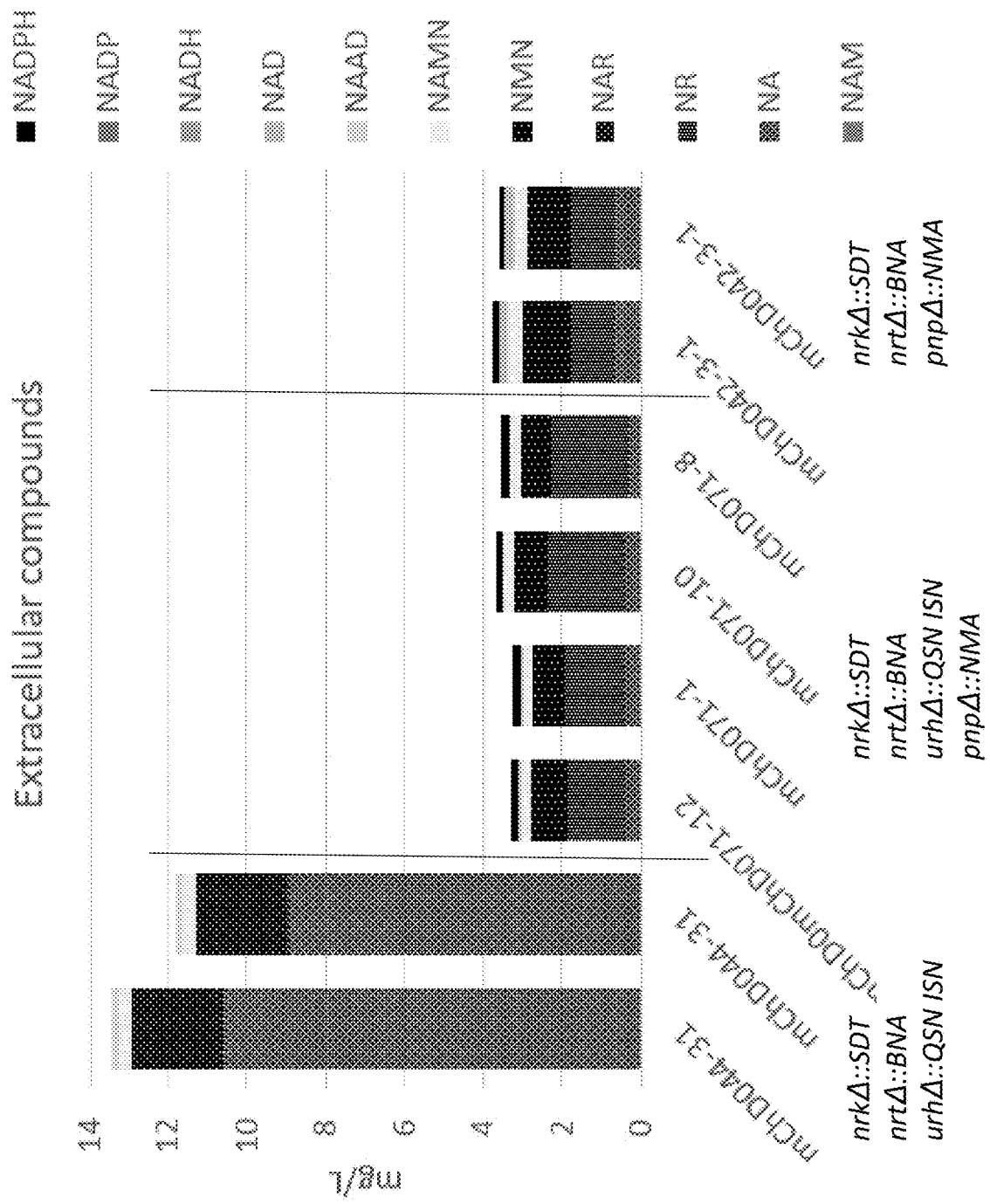
FIGS. 5A-5B. Extracellular metabolite concentrations (mg/L) produced by M1889 derived (FIG. 5A) or M1892 derived (FIG. 5B) modified strains. The relevant genetic modifications are shown below the graphs.
Figure 5B:
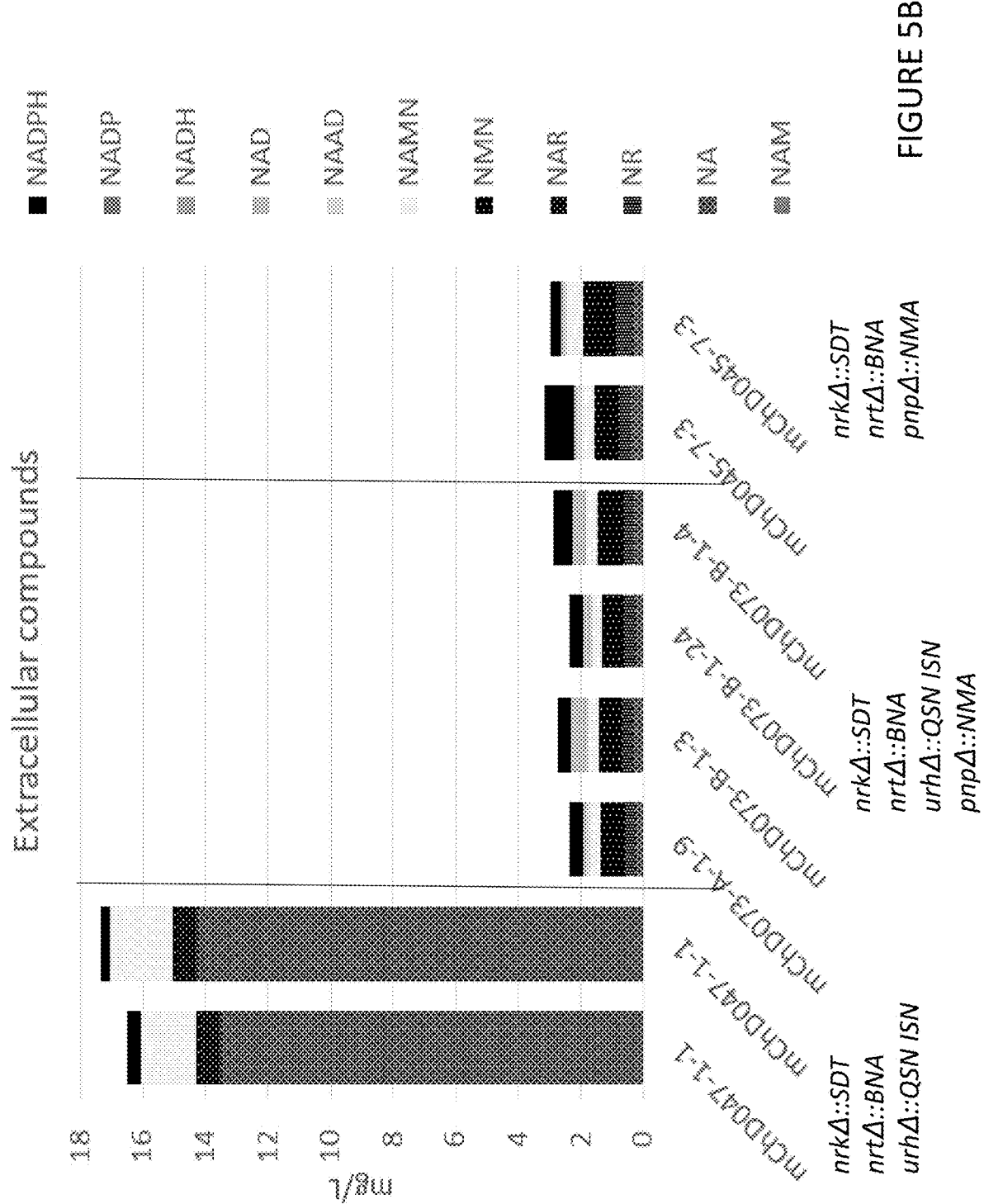
Figure 6A:
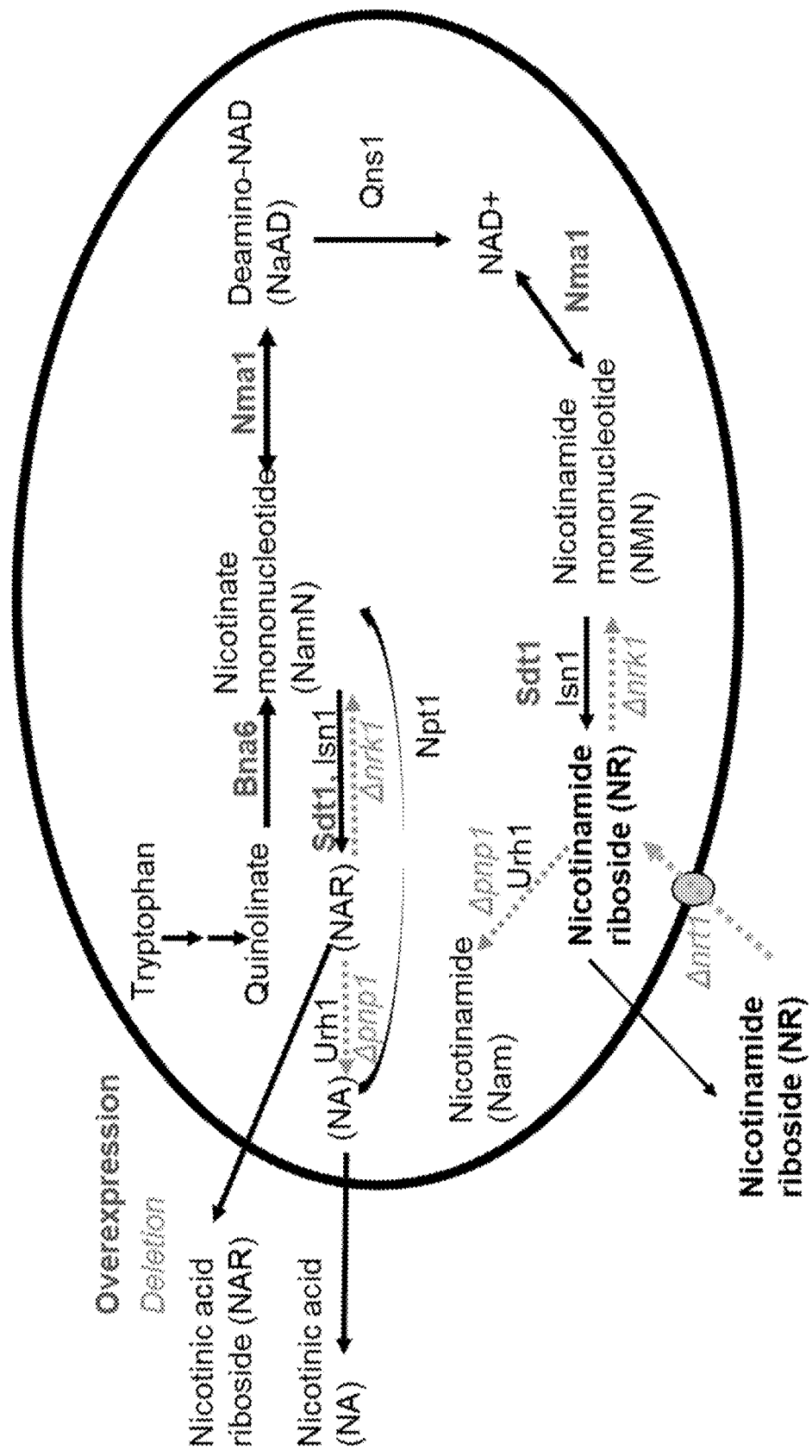
FIGS. 6A-6C NR biosynthesis modifications in selected strains.
Figure 6B:
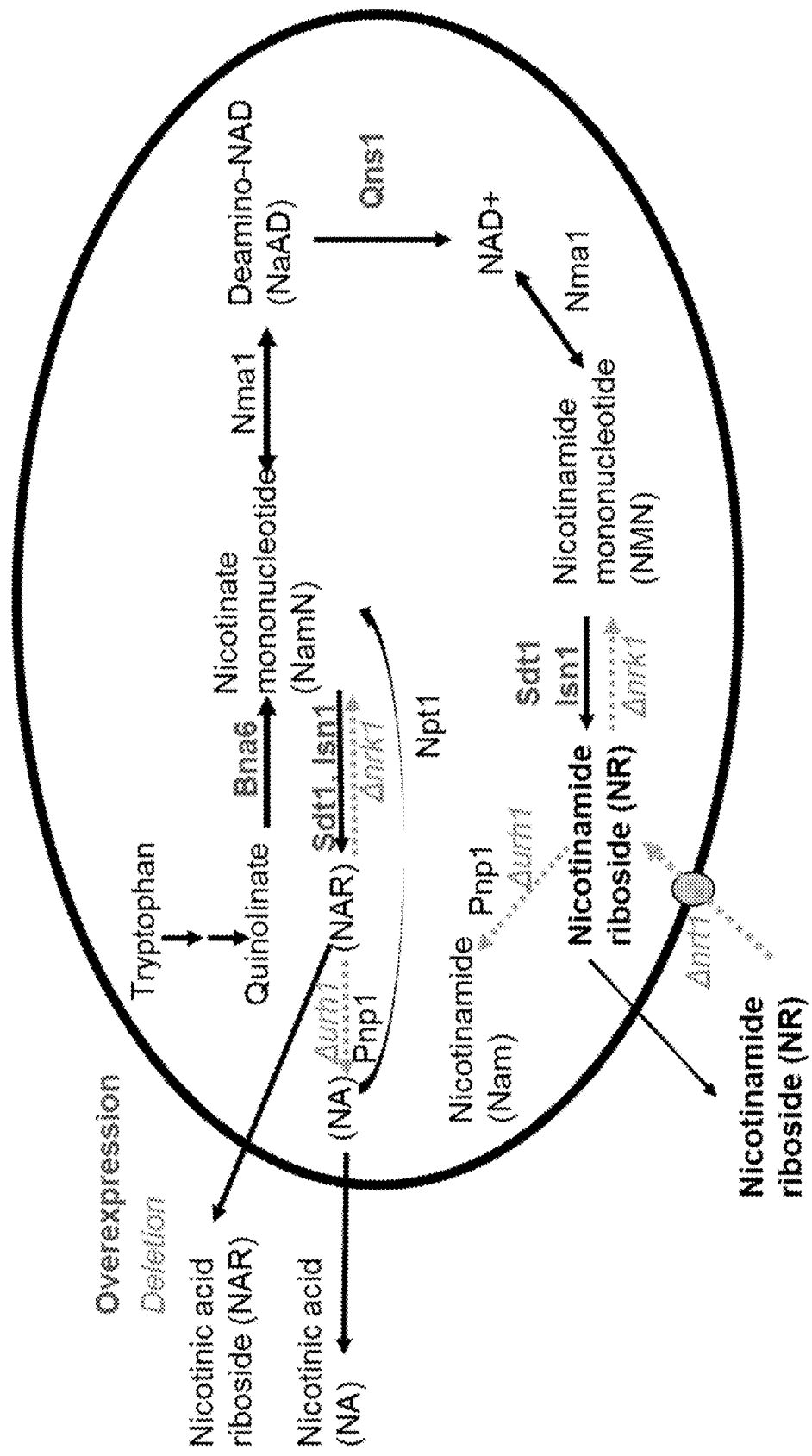
Figure 6C:
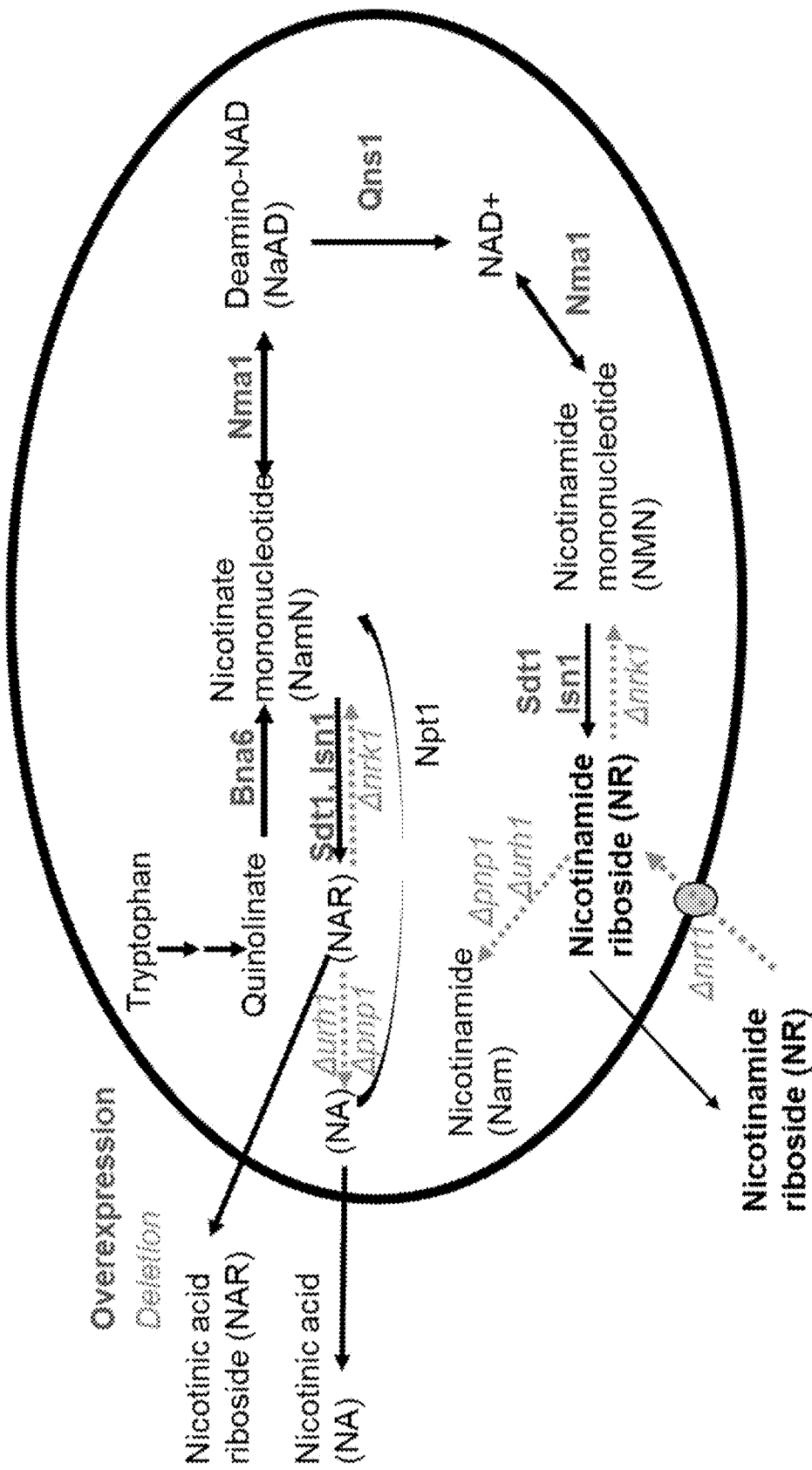

The strains mChD071 and mChD073 containing all the planned modifications, deletion of nrk1, pnp1, urh1 and nrt1 genes and overexpressing SDT1, BNA6, NMA1, QNS1 and ISN1, were analyzed for excreted NR related metabolites along with their predecessors mChD042, mChD044, mChD045 and mChD047, which lacked the final modifications (FIG. 5). The corresponding modifications in NR biosynthetic pathway are shown in FIG. 6. The M1889 derived strain mChD071 produced more NR and less NAR, a by-product, than any other strain including the previous best strain mChD042-3-1. M1889-derived strains mChD083 and mChD084 contain the same pathway modifications as mChD071 as verified by PCR, but they have different markers (see table 2).

Deletion of the pnp1 gene rather than NMA1 overexpression was crucial for increasing NR production and decreasing NA production. mChD044-1 was transformed with pChD004 in order to delete pnp1. The resulted colonies also included colonies in which pnp1 was intact. In these colonies the concentrations of excreted metabolites resembled that of mChD044-1 (FIG. 5 and data not shown).

Example 5

Automated Cultivations and Production of NR in 96-Well Plates

The suitability of a Screening Robot system for this invention was tested. The system, which is a custom set-up by Beckman-Coulter, is able to handle several 96-well format deep-well plates simultaneously. Inoculation, cultivation, centrifugation, supernatant removal and sample storage at +4° C. can be all automatically performed. Also, an automated colony picking from Petri dishes to 96-well format prior screening enhances the screening efficiency. This all allows a throughput of more than a thousand mutants per week.

The screening test was performed for four strains. Transformation host strain M1889 (high cellulose strain) and its daughter strain mChD001 (Δnrk1:SDT1, pyr5), and the transformation host strain M1892 (low cellulose strain) and its daughter strain mChD004 (Δnrk1; SDT1, pyr5) were used. The main goals were to test whether all of the steps work technically with C1 and that NR production improvement is detectable in mother-daughter strains when doing all of the work with robot.

Figure 7:
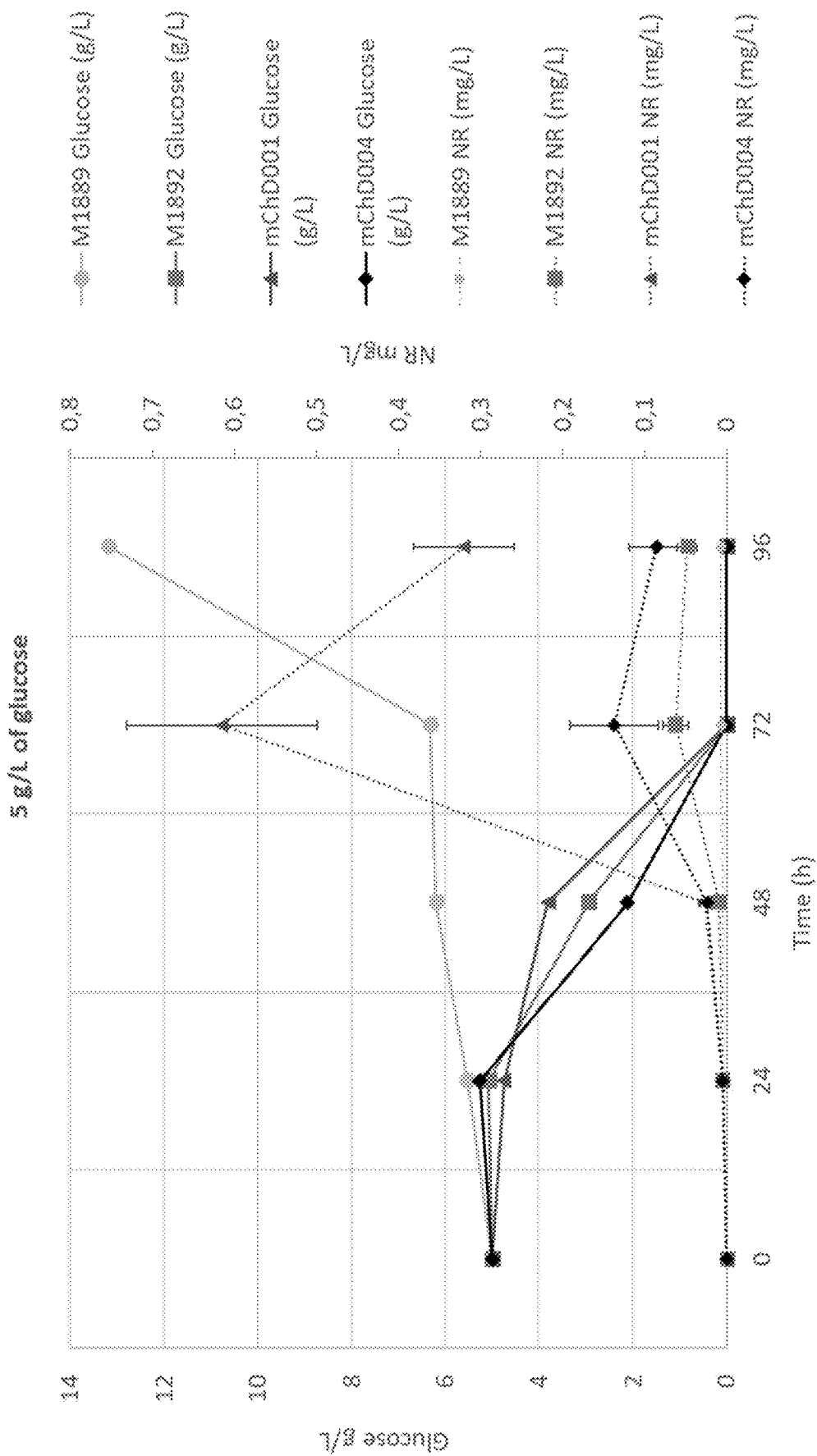
FIG. 7. Glucose consumption and NR production during 96 hours at +35° C. of strains M1889, M1892, mChD001 and mChD004 in 5 g/L starting glucose production medium. Increased glucose concentrations at 96 h are due to evaporation and decreased NR concentrations at 96 h due to degradation.
Figure 8:
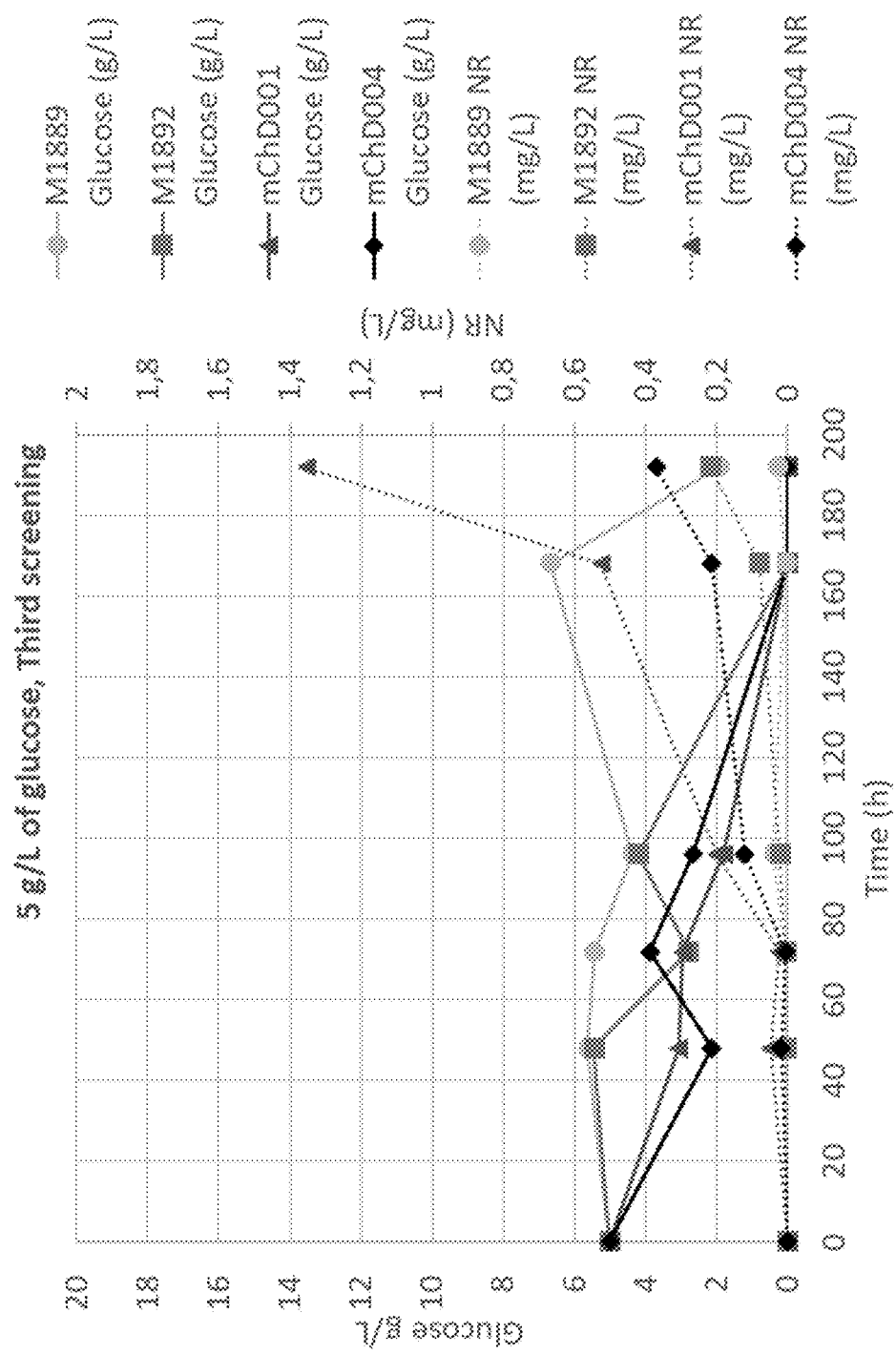
FIG. 8. Glucose consumption and NR production during 192 hours (first 48 h at +35° C., then +20° C.) of strains M1889, M1892, mChD001 and mChD004 in 5 g/L starting glucose production medium. Values are the lowest glucose and highest NR amounts measured per strain per time-point.

The screening was done as described herein. Colonies were picked from Petri dishes to agar-filled 96-well format plates with a Qpix colony picker and incubated at +35° C. After visible colonies were formed, the wells were washed with a washing buffer, which rinsed off the formed spores from the mycelium. The resulting spore suspension was then used to inoculate 1 mL of production medium (20 or 5 g/L of glucose) in 96-well format deep-well plates. Next, three incubation temperature strategies were tested in order to assess the required time and temperature for optimal screening results. Incubation at +20° C. for 3 days did not result in spore germination and growth. Incubation at +35° C. for 4 days resulted in spore germination, growth and NR production (up to 0.6 mg/L with mChD001 at 72 h; see FIG. 7). A combination of these two incubation temperatures (growth phase of 2 days at +35° C. followed by a production phase of 6 days at +20° C.) resulted in spore germination, growth and NR production (up to 1.3 mg/L with mChD001 at 192 h; see FIG. 8). After the incubation, cells were centrifuged down and supernatant was collected. It was either stored at +4° C. and analyzed the following night, or stored at −20° C. for 1-3 days, thawed and analyzed for NR and other metabolites.

Although the decreased incubation temperature in the production phase resulted in higher NR production, it did not change the screening result itself. Modified daughter strains produced more NR than the mother strains, and the strain order based on NR production stayed the same between and during the different incubation strategies. These results show that by utilizing a Screening Robot set-up one is able to choose the best producers for upscale tests and for further modifications.

Example 6

NR Production of Fungi Grown in Biolector

Biolector Pro by m2p-labs is a microbioreactor device. It hosts one 48-well format flower-shaped-deep-well plate at a time in a humid, shaken, temperature-controlled and oxygen-rich environment. Each of the wells can be monitored for several cultivation parameters through optical chemical sensors or clear well bottom. This enables the online measurement of, for example, dissolved oxygen, pH, biomass and riboflavin or other fluorescent compounds. One proof-of-concept Biolector Pro cultivation was conducted in order to assess its usability for screening. Biolector Pro can be used as an additional step between the Screening Robot and actual bench-top bioreactors.

Biolector Pro was tested for the following strains. Transformation host strain M1889 (high cellulose strain) and its daughter strains mChD001 (Δnrk1; SDT1, pyr5), mChD037-8-B (Δnrk1:SDT1, Δnrt1; BNA6, amdS, Δnia1), mChD042-3-1 (Δnrk1:SDT1, Δnrt1; BNA6, Δpnp1:NMA1, Nia1, HygR, amdS), mChD044-31 (Δnrk1:SDT1, Δnrt1; BNA6, Δurh1:ISN1, QNS1, HygR, amdS, Δnia1) and mChD079 (Δnrk1:SDT1, Δnrt1; BNA6, Δpnp1:NMA1, Nia1, HygR). Transformation host strain M1892 (low cellulose strain) and its daughter strains mChD004 (Δnrk1; SDT1, pyr5), mChD041-16-b-2 (Δnrk1:SDT1, Δnrt1; BNA6, amdS, Δnia1), mChD045-7-3 (Δnrk1:SDT1, Δnrt1; BNA6, Δpnp1:NMA1, Nia1, HygR, amdS), mChD047-1-1 (Δnrk1:SDT1, Δnrt1; BNA6, Δurh1:ISN1, QNS1, HygR, amdS, Δnia1) and mChD082 (Δnrk1:SDT1, Δnrt1; BNA6, Δpnp1:NMA1, Nia1, HygR).

Each of the twelve strains were cultivated in four parallels in 1 mL of production medium at +35° C., 800 rpm and head-space oxygen 35% for 72 hours. Half of the samples were removed at 48 hours. Biomass and riboflavin were measured online at 10-minute intervals and samples (48 and 72 h) were analyzed for NR and other metabolites both from the supernatant and by cold-methanol extraction (cells+supernatant analysis).

Figure 9A:
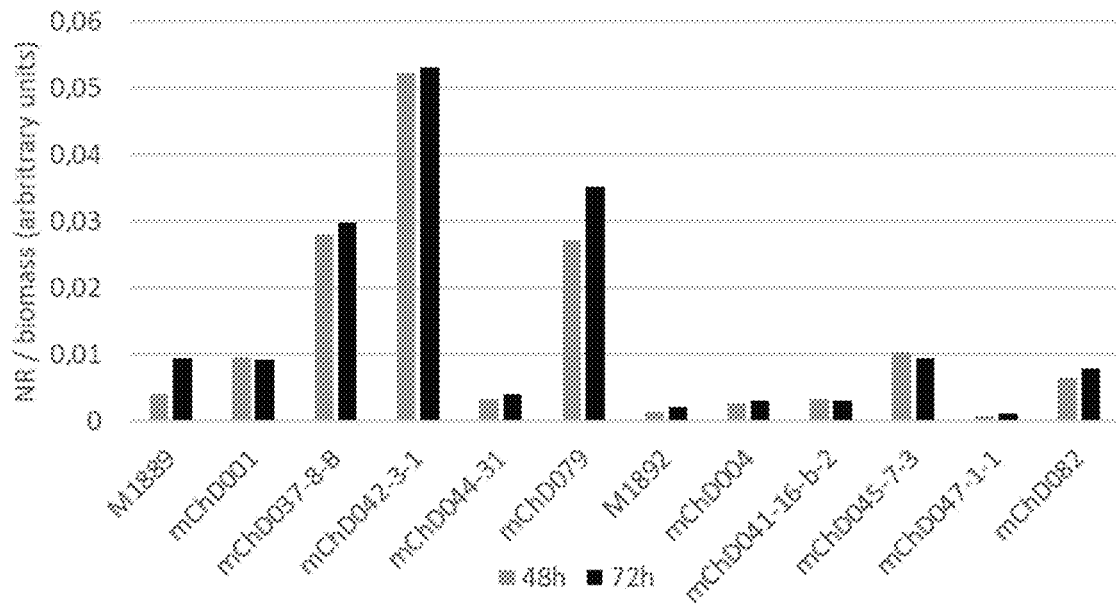
FIGS. 9A-9B. Biomass-normalized Biolector Pro cultivation results. Both supernatant (FIG. 9A) and cell+supernatant (FIG. 9B) results are shown for each of the strains at two time points (48 and 72 h).
Figure 9B:
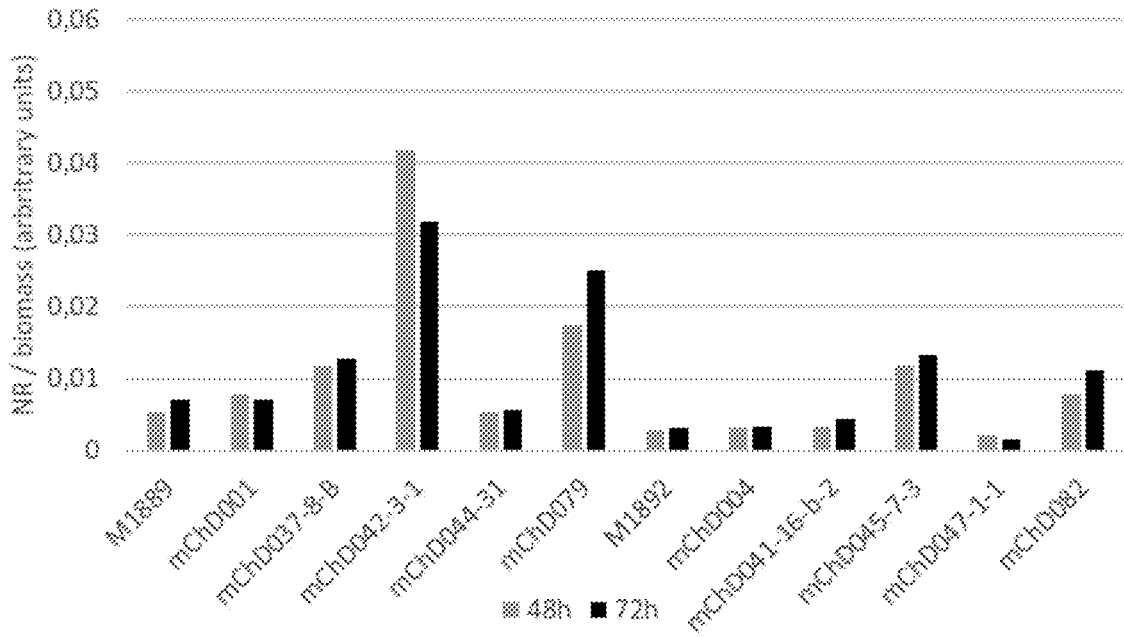

FIG. 9 shows the amount of NR normalized to biomass at 48 and 72 h. M1889-family strains produced more NR and a clear production improvement trend can be seen between mother and great-granddaughter strains. By normalizing the NR production to biomass, it is evident that a unit of modified cells produce more NR. Amount of up to 3.5 mg/L (strain mChD042-3-1) of NR was present in the supernatant at 72 h. Biolector Pro suits for screening C1 strains and it gives a great benefit of online biomass detection although its throughput is not as high as Screening Robot's.

Example 7

NR Production Bioreactor Cultivation

To optimize and evaluate the NR producing strains in bioreactors, strain mChD42-3-1 (Δnrk1:SDT1 Δnrt:BNA6 Δpnp1:NMA1) was cultivated in a 1 L bioreactor using conditions that are typical C1 protein production conditions.

The inoculum grew in shake flasks more slowly than expected and therefore the initial biomass in bioreactor was relatively low at the early stages of the cultivation. The cultivation temperature was 38° C. and pH 6.8. The culture was grown in batch mode for the first 24 hours, where after glucose, mineral salts and vitamins were fed into the reactor.

Samples were collected for the determination of biomass, secreted proteins and NR-related metabolites at 23, 47, 71, 95 and 165 h.

Figure 10A:
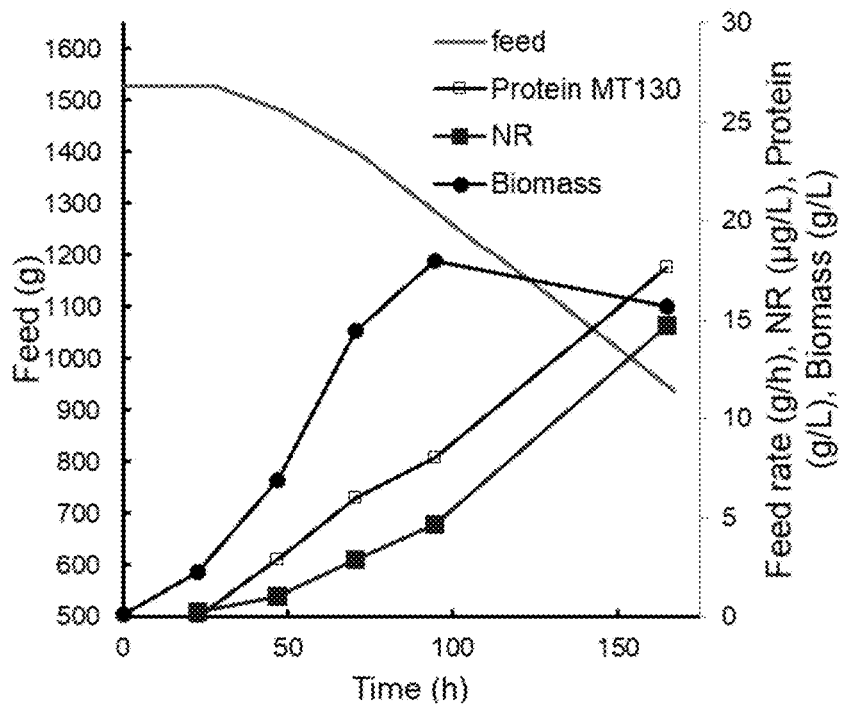
FIGS. 10A-10C.
Figure 10B:
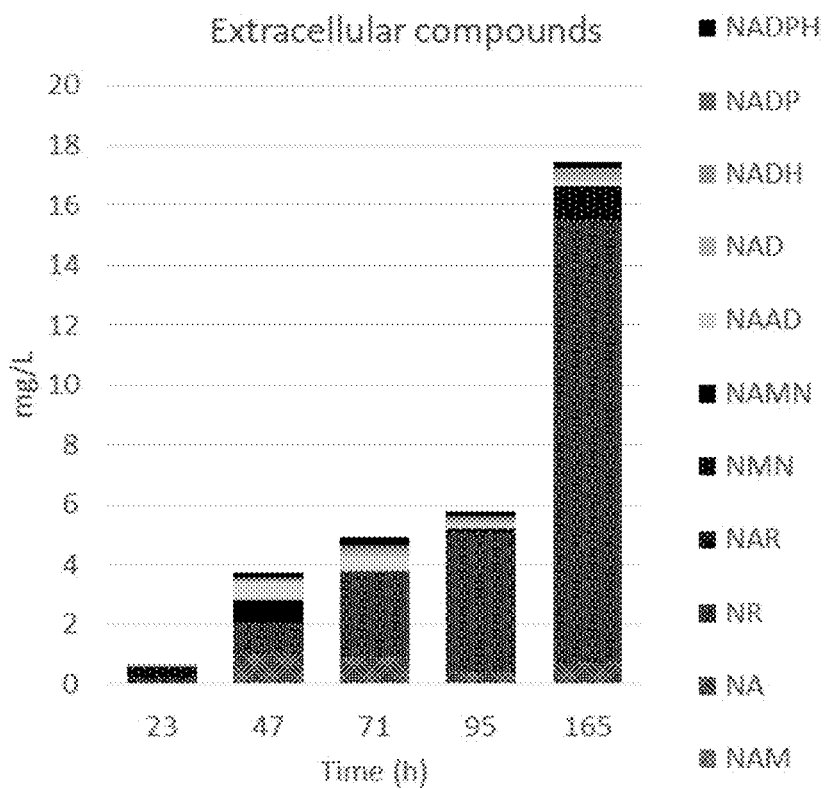
Figure 10C:
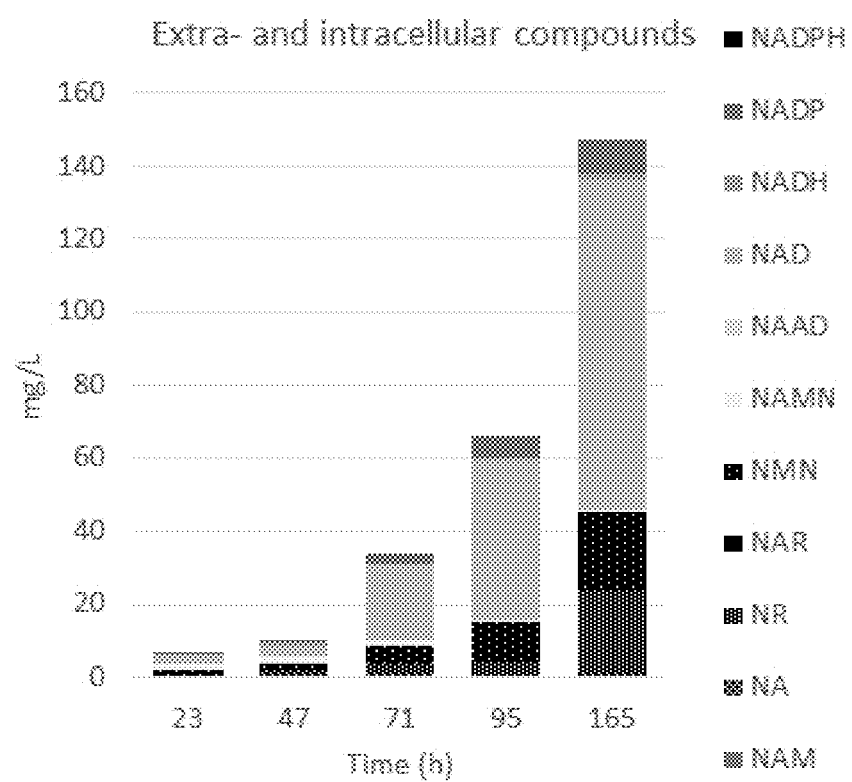

Excreted NR concentration was 15 mg/L, and total NR concentration was 22 mg/L at the end of the cultivation 165 h. The culture parameters are as follows:

Batch phase: 1 L reactor (Q)–initial volume 800 ml;
T=38° C.;
pH=6.8; pH control=NH$_4$OH (12.5%);
aeration=0.6 slpm;
Agitation=500-1250 rpm–cascade control;
Dissolved oxygen tension –>30% during first 8 h, then >25% cascade control needed–adjust manually;
Antifoam=J647–manual addition ca. 6 ml, 1 ml each evening
Feed: 503 g/L glucose containing 1× mineral salts for feeding, plus biotin and thiamine Biomass and secreted protein concentrations at 165 h were 15 g/L and 17 g/L, respectively (FIG. 10A). NR concentration increased throughout the cultivation and it was the most abundant NR-related metabolite found in the culture medium from 71 h onwards (FIG. 10A-10B). In comparison, NAD was the most abundant metabolite inside the cells (FIG. 10C). NAD and NMN are the two immediate precursors of NR biosynthesis. Based on this fact it is contemplated that a significant proportion of NAD and NMN may be converted to NR if strain development is continued.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A genetically modified ascomycetous filamentous fungus for producing nicotinamide riboside or a precursor thereof, the genetically modified filamentous fungus comprising at least one cell comprising three exogenous polynucleotides encoding for SDT1, BNA6, and NMA1, said fungus cell having deleted or disrupted NRK1, NRT1 and PNP1 genes.

2. The genetically modified ascomycetous filamentous fungus of claim 1, wherein BNA6 comprises an amino acid sequence having at least 75%, or at least 85%, or at least 90%, or at least 95%, or at least 99%, or 100% identity to the amino acid sequence of *Thermothelomyces heterothallica* BNA6.

3. The genetically modified ascomycetous filamentous fungus of claim 1, wherein the NMA1 comprises an amino acid sequence having at least 75%, or at least 85%, or at least 90%, or at least 95%, or at least 99%, or 100% identity to the amino acid sequence of *Thermothelomyces heterothallica* NMA1.

4. The genetically modified ascomycetous filamentous fungus of claim 1, said genetically modified ascomycetous filamentous fungus further comprises a an exogenous polynucleotides encoding QNS1 or ISN1.

5. The genetically modified ascomycetous filamentous fungus of claim 4, wherein the ISN1 comprises an amino acid sequence having at least 75 %, or at least 85 %, or at least 90 %, or at least 95 %, or at least 99 %, or 100 % identity to the amino acid sequence of *Thermothelomyces heterothallica* ISN1.

6. The genetically modified ascomycetous filamentous fungus of claim 1, wherein the SDT1 comprises an amino acid sequence having at least 75%, or at least 85%, or at least 90%, or at least 95%, or at least 99%, or 100% identity to the amino acid sequence of *Thermothelomyces heterothallica* SDT1.

7. The genetically modified ascomycetous filamentous fungus of claim 4, wherein the QNS1 comprises an amino acid sequence having at least 75 %, or at least 85 %, or at least 90 %, or at least 95 %, or at least 99 %, or 100 % identity to the amino acid sequence of *Thermothelomyces heterothallica* QNS 1.

8. The genetically modified ascomycetous filamentous fungus of claim 1, said genetically modified ascomycetous filamentous fungus comprises at least one cell having a deleted or disrupted Uridine hydrolase 1 (URH1) gene.

9. The genetically modified ascomycetous filamentous fungus of claim 1, comprising at least one cell having a plurality of exogenous polynucleotides encoding for each of SDT1, QNS1, ISN1, BNA6, and NMA1, said fungus comprises at least one cell having deleted or disrupted PNP1, URH1, NRT1 and NRK1 genes.

10. The genetically modified ascomycetous filamentous fungus of claim 1, wherein said genetically modified ascomycetous filamentous fungus produces nicotinamide ribose in an increased amount compared to the amount produced in a corresponding unmodified ascomycetous filamentous fungus cultured under similar conditions.

11. The genetically modified ascomycetous filamentous fungus of claim 1, wherein the ascomycetous filamentous fungus is of a genus within the subdivision *Pezizomycotina*.

12. The genetically modified ascomycetous filamentous fungus of claim 11 wherein the ascomycetous filamentous fungus is *Thermothelomyces heterothallica* C1.

13. The genetically modified ascomycetous filamentous fungus of claim 1, wherein the NR precursor is nicotinamide adenine dinucleotide (NAD) or nicotinamide mononucleotide (NMN).

14. A method of producing at least one nicotinamide riboside, the method comprising culturing the genetically modified fungus of claim 1 in a suitable medium; and
   recovering the produced at least one nicotinamide riboside product.

* * * * *